(12) United States Patent
Dhar et al.

(10) Patent No.: US 9,115,054 B2
(45) Date of Patent: Aug. 25, 2015

(54) TETRAHYDRONAPHTHALENYL COMPOUNDS USEFUL AS S1P1 AGONISTS

(71) Applicant: Bristol-Myers Squibb Company, Princeton, NJ (US)

(72) Inventors: T. G. Murali Dhar, Newtown, PA (US); Hai-Yun Xiao, Belle Mead, NJ (US); Alaric J. Dyckman, Lawrenceville, NJ (US); Eric J. Chan, New Brunswick, NJ (US); Marta Dabros, Lawrenceville, NJ (US); Daniel Richard Roberts, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/185,164

(22) Filed: Feb. 20, 2014

(65) Prior Publication Data

US 2014/0235591 A1    Aug. 21, 2014

Related U.S. Application Data

(60) Provisional application No. 61/767,531, filed on Feb. 21, 2013.

(51) Int. Cl.
*C07C 215/42* (2006.01)
*C07F 9/117* (2006.01)

(52) U.S. Cl.
CPC .............. *C07C 215/42* (2013.01); *C07F 9/117* (2013.01); *C07B 2200/07* (2013.01); *C07C 2101/08* (2013.01); *C07C 2102/10* (2013.01)

(58) Field of Classification Search
None
See application file for complete search history.

(56) References Cited

U.S. PATENT DOCUMENTS

| | | | |
|---|---|---|---|
| 6,069,143 | A | 5/2000 | Ali et al. |
| 7,309,721 | B2 | 12/2007 | Budhu et al. |
| 7,351,725 | B2 | 4/2008 | Doherty et al. |
| 7,479,504 | B2 | 1/2009 | Bugianesi et al. |
| 7,678,820 | B2 | 3/2010 | Harada et al. |
| 7,687,491 | B2 | 3/2010 | Nishi et al. |
| 8,354,398 | B2 | 1/2013 | Watterson et al. |
| 8,389,509 | B2 | 3/2013 | Dyckman et al. |
| 8,399,451 | B2 | 3/2013 | Gilmore et al. |
| 8,404,672 | B2 | 3/2013 | Pitts et al. |
| 8,629,282 | B2 | 1/2014 | Cherney et al. |
| 2005/0070506 | A1 | 3/2005 | Doherty et al. |
| 2006/0199853 | A1 | 9/2006 | Mioskowski et al. |
| 2008/0200535 | A1 | 8/2008 | Ohmori et al. |
| 2009/0029947 | A1 | 1/2009 | Wallace et al. |
| 2009/0247627 | A1 | 10/2009 | Trapp et al. |
| 2012/0214767 | A1 | 8/2012 | Dhar et al. |
| 2013/0045964 | A1 | 2/2013 | Cherney et al. |
| 2013/0158001 | A1 | 6/2013 | Das et al. |
| 2013/0190361 | A1 | 7/2013 | Das et al. |

FOREIGN PATENT DOCUMENTS

| | | |
|---|---|---|
| CN | 102260177 | 11/2011 |
| WO | WO 03/062248 | 7/2003 |
| WO | WO 03/062252 | 7/2003 |
| WO | WO 03/073986 | 9/2003 |
| WO | WO 03/105771 | 12/2003 |
| WO | WO 2005/000833 | 1/2005 |
| WO | WO 2005/058848 | 6/2005 |
| WO | WO 2005/082089 | 9/2005 |
| WO | WO 2006/047195 | 5/2006 |
| WO | WO 2006/088944 | 8/2006 |
| WO | WO 2006/094347 | 9/2006 |
| WO | WO 2006/100633 | 9/2006 |
| WO | WO 2006/131336 | 12/2006 |
| WO | WO 2007/024922 | 3/2007 |
| WO | WO 2007/081857 | 7/2007 |
| WO | WO 2007/088450 | 8/2007 |
| WO | WO 2007/089715 | 8/2007 |
| WO | WO 2007/109330 | 9/2007 |

(Continued)

OTHER PUBLICATIONS

Hale et al., "A Rational Utilization of High-Throughput Screening Affords Selective, Orally Bioavailable 1-Benzyl-3-carboxyazetidine Sphingosine-1-phosphate-1 Receptor Agonists," J. Med. Chem., 47, pp. 6662-6665 (2004).

Search Report and Written Opinion for PCT/US2014/017534, dated May 20, 2014.

Fix-Stenzel, S.R., et al., "A stereoselective and scalable synthesis of a conformationally constrained S1P$_1$ agonist," Tetrahedron Letters 50 (2009), pp. 4081-4083.

Oliveira, Caio O., et al., "Stereoselective Arylation of Substituted Cyclopentenes by Substrate-Directable Heck-Matsuda Reactions: A Concise Total Synthesis of the Sphingosine 1-Phosphate Receptor (S1P$_1$) Agonist VPc01091," J. Org. Chem. (2012), vol. 77, pp. 8182-8190.

(Continued)

*Primary Examiner* — James D Anderson
(74) *Attorney, Agent, or Firm* — Gary D. Greenblatt

(57) ABSTRACT

Disclosed are compounds of Formula (I)

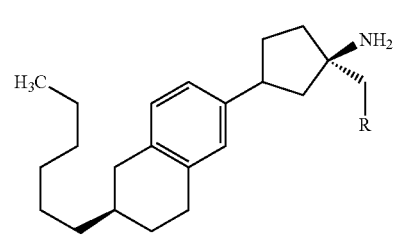

(I)

and/or a salt thereof; wherein R is —OH or —OP(O)(OH)$_2$. Also disclosed are methods of using such compounds as selective agonists for G protein-coupled receptor S1P$_1$, and pharmaceutical compositions comprising such compounds. These compounds are useful in treating, preventing, or slowing the progression of diseases or disorders in a variety of therapeutic areas, such as autoimmune diseases and vascular disease.

20 Claims, 9 Drawing Sheets

(56) References Cited

FOREIGN PATENT DOCUMENTS

| WO | WO 2007/111864 | 10/2007 |
|----|----------------|---------|
| WO | WO 2008/029370 | 3/2008 |
| WO | WO 2008/074820 | 6/2008 |
| WO | WO 2008/092785 | 8/2008 |
| WO | WO 2008/114157 | 9/2008 |
| WO | WO 2009/043889 | 4/2009 |
| WO | WO 2009/057079 | 5/2009 |
| WO | WO 2009/080728 | 7/2009 |
| WO | WO 2010/042998 | 4/2010 |
| WO | WO 2010/069949 | 6/2010 |
| WO | WO 2010/072352 | 7/2010 |
| WO | WO 2010/081692 | 7/2010 |
| WO | WO 2010/093616 | 8/2010 |
| WO | WO 2011/147311 | 12/2011 |
| WO | WO 2012/158550 | 11/2012 |
| WO | WO 2014/018891 | 1/2014 |

OTHER PUBLICATIONS

Wallace, G.A., et al., "Scalable Synthesis and Isolation of the Four Stereoisomers of Methyl 1-Amino-3-(4-bromophenyl)cyclopentanecarboxylate, Useful Intermediates for the Synthesis of S1P1 Receptor Agonists," J. Org. Chem. (2009), vol. 74, pp. 4886-4889.

Zhu, R., et al., "Asymmetric Synthesis of Conformationally Constrained Fingolimod Analogues—Discovery of an Orally Active Sphingosine 1-Phosphate Receptor Type-1 Agonist and Receptor Type-3 Antagonist," J. Med. Chem. (2007), vol. 50, pp. 6428-6435.

TETRAHYDRONAPHTHALENYL COMPOUNDS USEFUL AS S1P1 AGONISTS

The present invention generally relates to bicyclic compounds useful as $S1P_1$ agonists. Provided herein are bicyclic compounds, compositions comprising such compounds, and methods of their use. The invention further pertains to pharmaceutical compositions comprising at least one compound according to the invention that are useful for the treatment of conditions related to $S1P_1$ modulation, such as autoimmune diseases and vascular disease.

Sphingosine-1-phosphate (S1P) is a zwitterionic lysophospholipid metabolite of sphingosine (Sph), which in turn is derived from enzymatic cleavage of ceramides. Enzymatic phosphorylation of Sph by two kinases (SphK1 and SphK2) leads to the production of S1P largely from erythrocytes, but also from a radiation resistant source, possibly the lymphatic endothelium (Pappu, R. et al., *Science*, 316:295-298 (2007)). Originally thought to operate solely as an intracellular signaling molecule, S1P was subsequently identified as a high affinity ligand for five members of the endothelial differentiation gene (EDG) class of G-protein coupled receptors (GPCRs) named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively) (Chun, J. et al., *Pharmacological Rev.*, 62:579-587 (2010)). The interaction of S1P with the S1P receptors plays a fundamental physiological role in a large number of processes including cell proliferation, cell morphology, tumor cell invasion, angiogenesis, tumorigenesis, cytoskeletal rearrangement, vascular development, and lymphocyte trafficking (Olivera, A. et al., *Adv. Exp. Med. Biol.*, 716:123-142 (2011)). S1P receptors are therefore good targets for a wide variety of therapeutic applications such as tumor growth inhibition, vascular disease, and autoimmune diseases.

Among the five S1P receptors, $S1P_1$ has a widespread distribution. It is the predominant family member expressed on lymphocytes and plays an important role in lymphocyte trafficking. S1P interaction with its receptor $S1P_1$ is required for the egress of immune cells from the lymphoid organs (such as thymus and lymph nodes) into the lymphatic vessels. Downregulation of the $S1P_1$ receptor (which can be accomplished through treatment with agonists of $S1P_1$ via receptor internalization) disrupts lymphocyte migration and homing to various tissues. This results in sequestration of the lymphocytes in lymph organs thereby decreasing the number of circulating lymphocytes that are capable of migration to the affected tissues. The development of an $S1P_1$ receptor modulating agent that suppresses lymphocyte migration to the target sites associated with autoimmune and aberrant inflammatory processes could be efficacious in a number of autoimmune and inflammatory disease states.

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109,330, WO 07/116,866, WO 08/023,783 (U.S. Patent Publication No. 2008/0200535), WO 08/029,370, WO 08/074,820, WO 08/079,382, WO 08/114,157, WO 09/043,889, WO 09/057,079, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$. Further, there still remains a need for compounds useful as $S1P_1$ agonists that have selectivity over $S1P_3$ and also have minimal or no undesirable pulmonary effects.

Applicants have found potent compounds that have activity as $S1P_1$ agonists. Further, applicants have found compounds that have activity as $S1P_1$ agonists and are selective over $S1P_3$. Further still, applicants have found compounds that have activity as $S1P_1$ agonists, are selective over $S1P_3$, and have minimal or no undesirable pulmonary effects. These compounds are provided to be useful as pharmaceuticals with desirable stability, bioavailability, therapeutic index, and toxicity values that are important to their drugability.

SUMMARY OF THE INVENTION

The present invention provides bicyclic compounds, which are useful as modulators of $S1P_1$ activity, including salts and prodrugs thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of G protein-coupled receptor $S1P_1$, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment or prophylaxis of $S1P_1$ receptor-related conditions, such as autoimmune and vascular diseases.

The compounds of Formula (I) and compositions comprising the compounds of Formula (I) may be used in treating, preventing, or curing various $S1P_1$ related conditions. Pharmaceutical compositions comprising these compounds are useful in treating, preventing, or slowing the progression of diseases or disorders in a variety of therapeutic areas, such as autoimmune and vascular diseases.

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION

Figure 1:
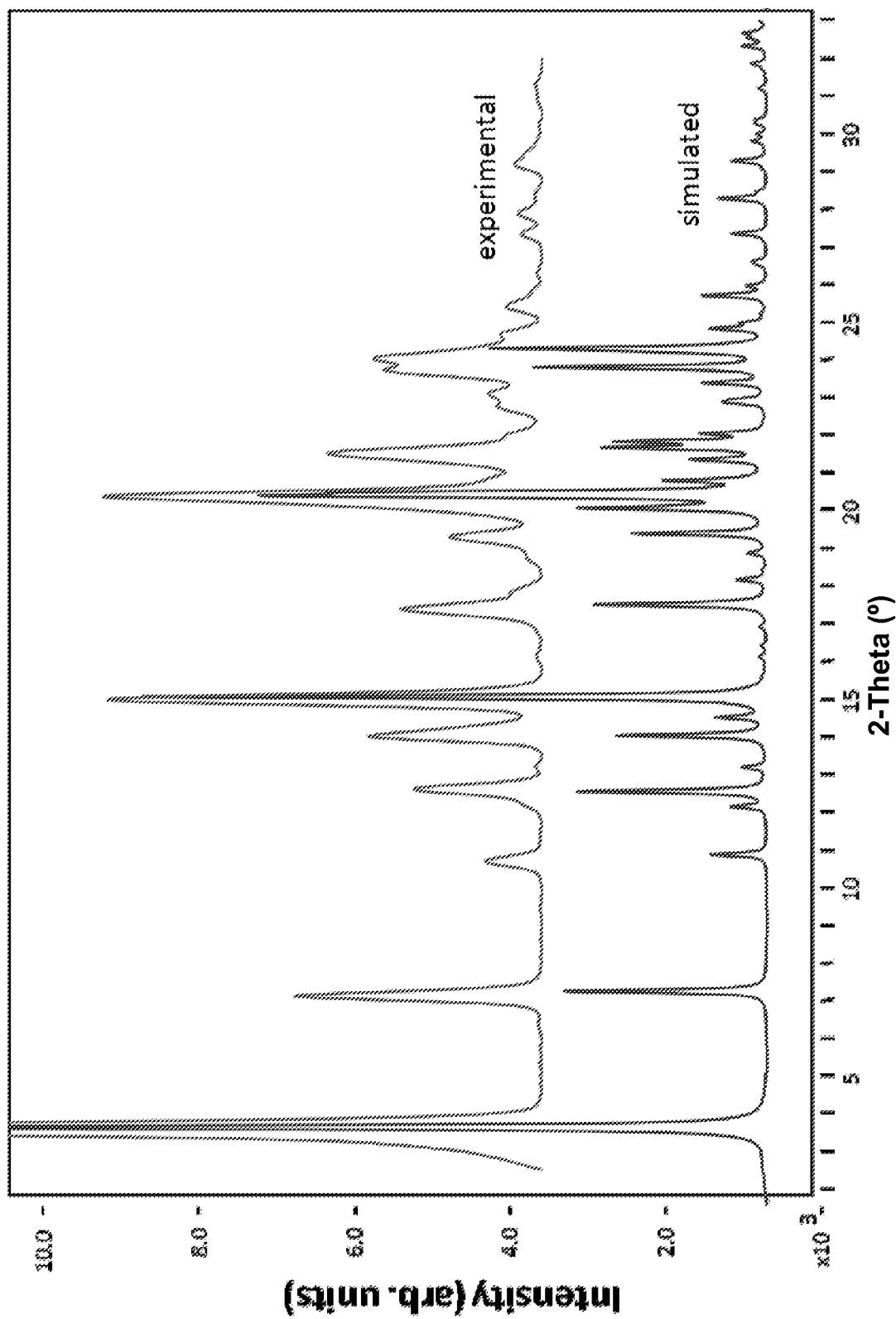
FIG. 1 shows the experimental and the simulated PXRD patterns (CuKα λ=1.5418 Å at approximately 25° C.) of the N-1 Form of the compound of Example 2.

The first aspect of the present invention provides at least one compound of Formula (I):

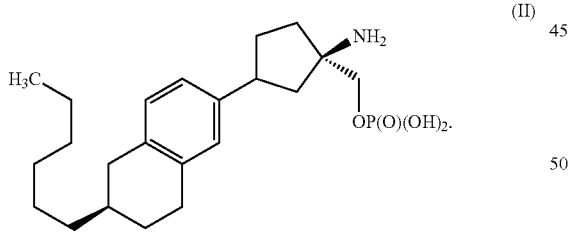

(I)

and/or a salt thereof; wherein R is —OH or —OP(O)(OH)$_2$.

One embodiment provides compounds of Formula (I) and/or salts thereof, wherein R is —OP(O)(OH)$_2$. The compounds of this embodiment have the structure of Formula (II):

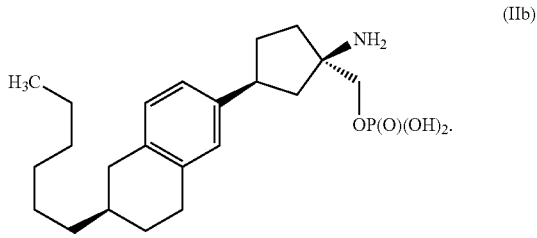

(II)

Included in this embodiment are the compound of Formula (IIa) and

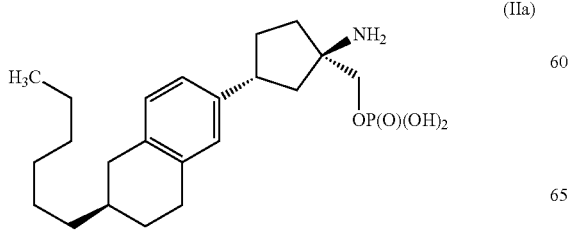

(IIa)

and the compound of Formula (IIb):

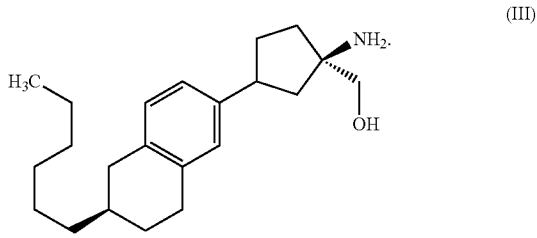 [SMILES: CCCCCC[C@@H]1CCc2cc(C3CC[C@](N)(CO)C3)ccc2C1]

(IIb)

The compounds of Formula (II) and/or salts thereof, are useful as selective agonists of S1P$_1$.

One embodiment provides compounds of Formula (I) and/or salts thereof, wherein R is —OH. The compounds of this embodiment have the structure of Formula (III):

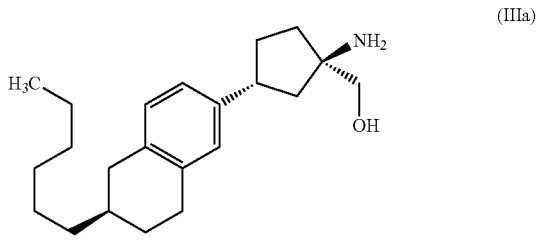 [SMILES: CCCCCC[C@@H]1CCc2cc([C@@H]3CC[C@](N)(CO)C3)ccc2C1]

(III)

Included in this embodiment are the compound of Formula (IIIa) and

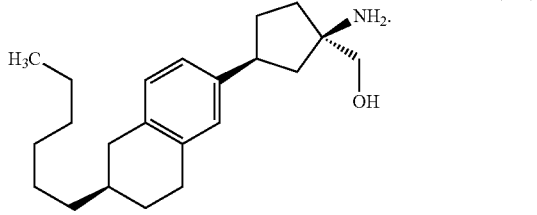

(IIIa)

and the compound of Formula (IIIb):

(IIIb)

The compounds of Formula (III) and/or salts thereof, are useful as prodrugs of the compounds of Formula (II). The compounds of Formula (III) are activated in vivo through phosphorylation to provide the compounds of Formula (II). The compounds of Formula (II) are active as a selective agonists of S1P$_1$.

One embodiment provides compounds of Formula (I) and/or salts thereof, having the structure of Formula (IV):

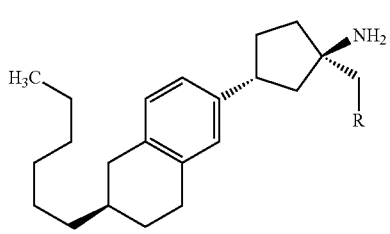

wherein R is —OH or —OP(O)(OH)$_2$. Included in this embodiment are the compounds of Formula (IIa) and Formula (IIIa).

One embodiment provides compounds of Formula (I) and/or salts thereof, having the structure of Formula (V):

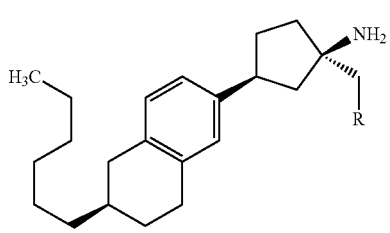

wherein R is —OH or —OP(O)(OH)$_2$. Included in this embodiment are the compounds of Formula (IIb) and Formula (IIIb).

One embodiment provides the compound of Formula (IIa) and/or salts thereof.

One embodiment provides the compound of Formula (IIb) and/or salts thereof.

One embodiment provides the compound of Formula (IIIa) and/or salts thereof.

One embodiment provides the compound of Formula (IIIb) and/or salts thereof.

One embodiment provides the compound of Formula (IIa).

One embodiment provides the compound of Formula (IIb).

One embodiment provides the compound of Formula (IIIa).

One embodiment provides the compound of Formula (IIIb).

One embodiment provides one or more salts of the compound of Formula (IIa).

One embodiment provides one or more salts of the compound of Formula (IIb).

One embodiment provides one or more salts of the compound of Formula (IIIa).

One embodiment provides one or more salts of the compound of Formula (IIIb).

One embodiment provides the compound of Formula (III) as an HCl salt.

One embodiment provides the compound of Formula (IIIa) as an HCl salt.

One embodiment provides the compound of Formula (IIIb) as an HCl salt.

One embodiment provides the compound of Formula (III) as a phosphoric acid salt.

One embodiment provides the compound of Formula (IIIa) as a phosphoric acid salt.

One embodiment provides the compound of Formula (IIIb) as a phosphoric acid salt.

One embodiment provides the compound of Formula (IIIb) as an L-malic acid salt.

One embodiment provides the compound of Formula (III) as malonic acid salt.

One embodiment provides the compound of Formula (IIIa) as malonic acid salt.

One embodiment provides the compound of Formula (IIIb) as malonic acid salt.

One embodiment provides the compound of Formula (IIIb) as an R-(+)-mandelic acid salt.

One embodiment provides the compound of Formula (III) as a salt selected from HCl salt, phosphoric acid salt, and malonic acid salt.

One embodiment provides the compound of Formula (IIIa) as a salt selected from HCl salt, phosphoric acid salt, and malonic acid salt.

One embodiment provides the compound of Formula (IIIb) as a salt selected from HCl salt, phosphoric acid salt, L-malic acid salt, malonic acid salt, and R-(+)-mandelic acid salt.

One embodiment provides a compound selected from ((1R,3R)-1-amino-3-((R)-6-hexyl-5,6,7,8-tetrahydronaphthalen-2-yl)cyclopentyl)methanol and ((1R,3S)-1-amino-3-((R)-6-hexyl-5,6,7,8-tetrahydronaphthalen-2-yl)cyclopentyl)methanol; and salts thereof.

One embodiment provides a compound selected from ((1R,3R)-1-amino-3-((R)-6-hexyl-5,6,7,8-tetrahydronaphthalen-2-yl)cyclopentyl)methyl dihydrogen phosphate and ((1R,3S)-1-amino-3-((R)-6-hexyl-5,6,7,8-tetrahydronaphthalen-2-yl)cyclopentyl)methyl dihydrogen phosphate; and salts thereof.

One embodiment provides a compound selected from ((1R,3R)-1-amino-3-((R)-6-hexyl-5,6,7,8-tetrahydronaphthalen-2-yl)cyclopentyl)methanol and ((1R,3R)-1-amino-3-((R)-6-hexyl-5,6,7,8-tetrahydronaphthalen-2-yl)cyclopentyl)methyl dihydrogen phosphate; and salts thereof.

One embodiment provides a compound selected from ((1R,3S)-1-amino-3-((R)-6-hexyl-5,6,7,8-tetrahydronaphthalen-2-yl)cyclopentyl)methanol and ((1R,3S)-1-amino-3-((R)-6-hexyl-5,6,7,8-tetrahydronaphthalen-2-yl)cyclopentyl)methyl dihydrogen phosphate; and salts thereof.

Salts and Crystal Forms of the Compound of Example 2:

TABLE 1

| Salts and Crystalline Forms of Example 2 | |
|---|---|
| Example 2 | Form |
| free base | N-1 |
| mono-HCl salt (monohydrate) | H-1 |
| mono-HCl salt (monohydrate) | H-2 |
| mono-HCl salt | N-3 |
| mono-HCl salt | N-4 |
| hemi-L-Malic Acid salt (monohydrate) | H-1 |
| hemi-Malonic Acid salt (monohydrate) | H-1 |
| 2/3-Phosphoric Acid salt (1/3-hydrate) | H.33-1 |
| R-(+)-Mandelic Acid salt | N-1 |

Form N-1 of Example 2, Free Base

In one embodiment, the compound of Example 2

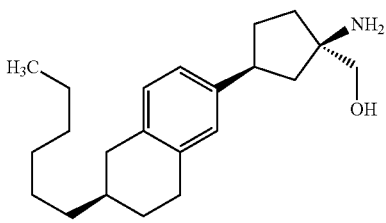

is provided as a crystalline material comprising the first crystalline form. The first crystalline form of the compound of Example 2 comprises a neat crystalline form referred to herein as "Form N-1" or "N-1 Form" of Example 2.

In one embodiment, the N-1 Form of Example 2 is characterized by unit cell parameters approximately equal to the following:
Cell dimensions:
a=5.54 Å
b=7.37 Å
c=48.85 Å
α=90.0°
β=90.0°
γ=90.0°
Space group: $P2_12_12_1$
Molecules of Example 2/asymmetric unit: 1
Volume/Number of molecules in the unit cell=499 Å$^3$
Density (calculated)=1.098 g/cm$^3$,
wherein the unit cell parameters of Form N-1 of Example 2 are measured at a temperature of about −70° C.

In another embodiment, the N-1 Form of Example 2 is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, the N-1 Form of Example 2 is characterized by a PXRD pattern (CuKα λ=1.5418 Å at a temperature of about 25° C.) comprising four or more, preferably five or more, 2θ values selected from: 3.6±0.2, 7.2±0.2, 12.5±0.2, 14.0±0.2, 15.0±0.2, 17.5±0.2, 19.4±0.2, 20.4±0.2, and 23.8±0.2, wherein the PXRD pattern of Form N-1 is measured at a temperature of about 25° C.

In still yet an even further embodiment, the N-1 Form of Example 2 is substantially pure.

In still yet another embodiment, the N-1 Form of Example 2 contains at least about 90 wt. %, preferably at least about 95 wt. %, and more preferably at least about 99 wt. %, based on weight of the Form N-1 of Example 2. In yet another embodiment, a substantially pure Form N-1 of Example 2 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline Form N-1 of Example 2 has substantially pure phase homogeneity with less than about 1% of the total peak area of the experimentally measured PXRD pattern arising from peaks that are absent from the simulated PXRD pattern.

In another embodiment, the crystalline form of Example 2 consists essentially of Form N-1. The crystalline form of this embodiment may comprise at least about 90 wt. %, preferably at least about 95 wt. %, and more preferably at least about 99 wt. %, based on the weight of the crystalline form, Form N-1 of Example 2.

In yet another embodiment, a pharmaceutical composition is provided comprising Form N-1 of Example 2; and at least one pharmaceutically-acceptable carrier and/or diluent.

In still another embodiment, a pharmaceutical composition comprises substantially pure Form N-1 of Example 2; and at least one pharmaceutically-acceptable carrier and/or diluent.

In still an even further embodiment, a therapeutically effective amount of Form N-1 of Example 2 is combined with at least one pharmaceutically acceptable carrier and/or diluent to provide at least one pharmaceutical composition.

HCl Salts of Example 2

In one embodiment, the Example 2 is provided as a hydrochloric acid salt.

In one embodiment, the Example 2 is provided as a mono-hydrochloric acid salt comprising one mole of HCl for each mole of Example 2.

In one embodiment, the mono-hydrochloric acid salt of Example 2 is provided as crystalline material comprising one or more crystalline forms. Examples of suitable crystalline forms of the mono-hydrochloric acid salt of Example 2 include Forms H-1, H-2, N-3, and N-4.

In one embodiment, the mono-hydrochloric acid salt of Example 2 is provided as a monohydrate.

In one embodiment, the monohydrate mono-hydrochloric acid salt of Example 2 is provided in as crystalline material comprising one or more crystalline forms. Examples of suitable crystalline forms of the monohydrate mono-hydrochloric acid salt of Example 2 include Forms H-1 and H-2.

In one embodiment, the monohydrate mono-hydrochloric acid salt of Example 2 is provided in a second crystalline form referred to herein as "Form H-1" or "H-1 Form" of Example 2, HCl salt. The H-1 Form of Example 2, HCl salt comprises one molecule of water and one molecule of HCl for each molecule of Example 2.

In one embodiment, the H-1 Form of the mono-hydrochloric acid salt of Example 2 is characterized by unit cell parameters approximately equal to the following:
Cell dimensions:
a=6.30 Å
b=6.42 Å
c=55.28 Å
α=90.0°
β=90.0°
γ=90.0°
Space group: $P2_12_12_1$
Molecules of Example 2/asymmetric unit: 1
Volume/number of molecules in the unit cell=560 Å$^3$
Density (calculated)=1.14 g/cm$^3$,
wherein the unit cell parameters of Form H-1 of the mono-hydrochloric acid salt of Example 2 are measured at a temperature of about −70° C.

Figure 2:
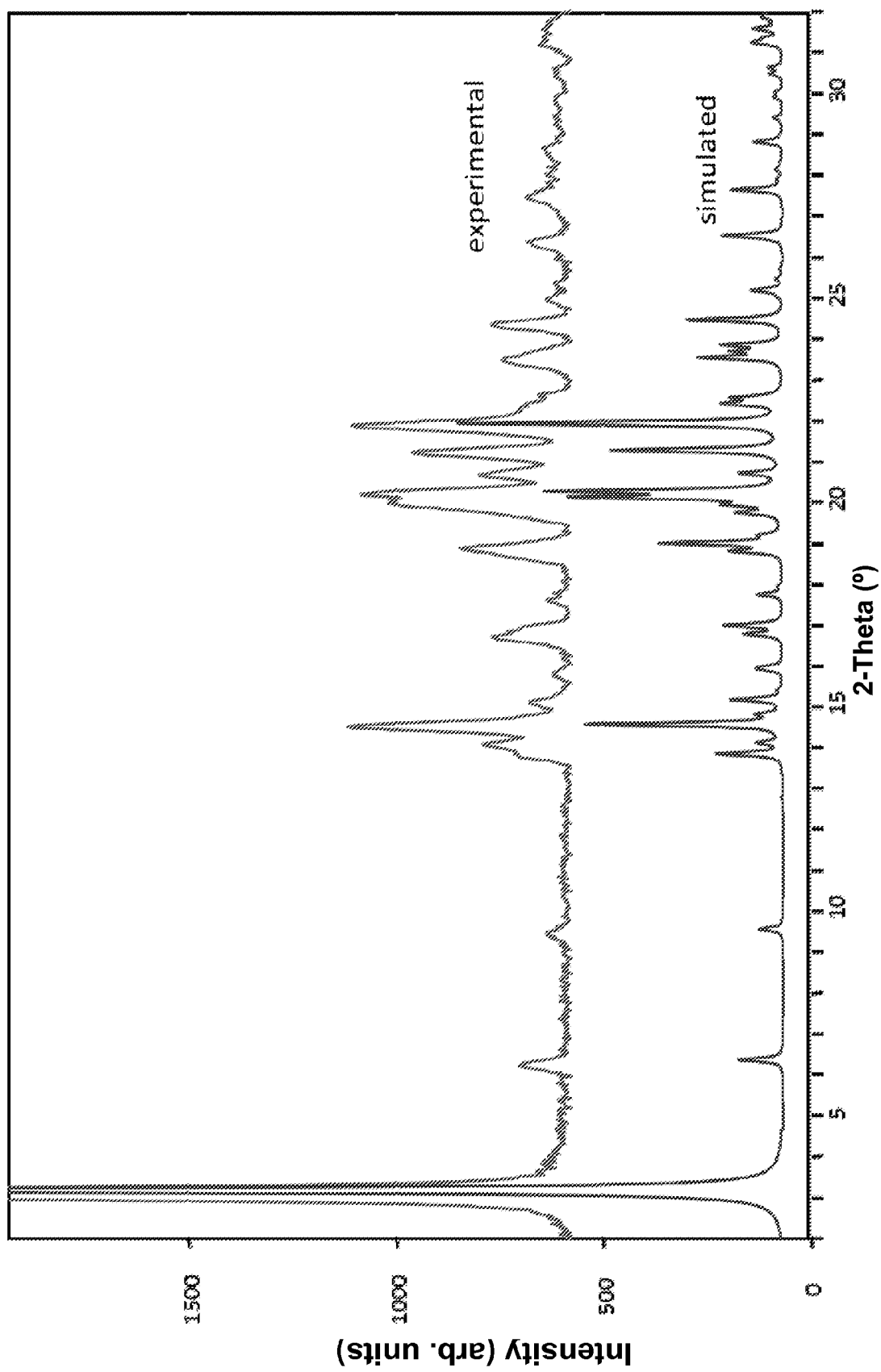
FIG. 2 shows the experimental and the simulated PXRD patterns (CuKα λ=1.5418 Å at approximately 25° C.) of the monohydrate H-1 Form of the mono-HCl salt of the compound of Example 2.

In another embodiment, the H-1 Form of the mono-hydrochloric acid salt of Example 2 is characterized by a simulated powder x-ray diffraction (PXRD) pattern substantially in accordance with the pattern shown in FIG. 2 and/or by an observed PXRD pattern substantially in accordance with the pattern shown in FIG. 2.

In yet another embodiment, the monohydrate H-1 form of the mono-HCl salt of Example 2 is characterized by a PXRD pattern (CuKα λ=1.5418 Å at a temperature of about 25° C.) comprising four or more, preferably five or more, 2θ values selected from: 3.2±0.2, 6.4±0.2, 9.6±0.2, 13.9±0.2, 14.6±0.2, 17.0±0.2, 19.0±0.2, 20.1±0.2, 21.3±0.2, 21.9±0.2, and 24.5±0.2, wherein the PXRD pattern is measured at a temperature of about 25° C.

In still yet an even further embodiment, the H-1 Form of the mono-hydrochloric acid salt of Example 2 is substantially pure.

In still yet another embodiment, the H-1 Form of the mono-hydrochloric acid salt of Example 2 contains at least about 90 wt. %, preferably at least about 95 wt. %, and more preferably at least about 99 wt. %, based on weight of the second crystalline form, Form H-1 of Example 2, HCl salt.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the mono-HCl salt of Example 2 consists essentially of Form H-1. The second crystalline form of this embodiment may comprise at least about 90 wt. %, preferably at least about 95 wt. %, and more preferably at least about 99 wt. %, based on the weight of the second crystalline form, Form H-1.

In one embodiment, the monohydrate mono-hydrochloric acid salt of Example 2 is provided in a third crystalline form referred to herein as "Form H-2" or "H-2 Form" of Example 2, HCl salt. The H-2 Form of Example 2, HCl salt comprises one molecule of water and one molecule of HCl for each molecule of Example 2.

In one embodiment, the H-2 Form of the mono-hydrochloric acid salt of Example 2 is characterized by unit cell parameters approximately equal to the following:
Cell dimensions:
a=6.30 Å
b=6.43 Å
c=27.88 Å
α=90.0°
β=96.0°
γ=90.0°
Space group: $P2_1$
Molecules of Example 2/asymmetric unit: 1
Volume/number of molecules in the unit cell=562 Å$^3$
Density (calculated)=1.135 g/cm$^3$,
wherein the unit cell parameters of the H-2 Form of Example 2, HCl salt are measured at a temperature of about −70° C.

Figure 3:
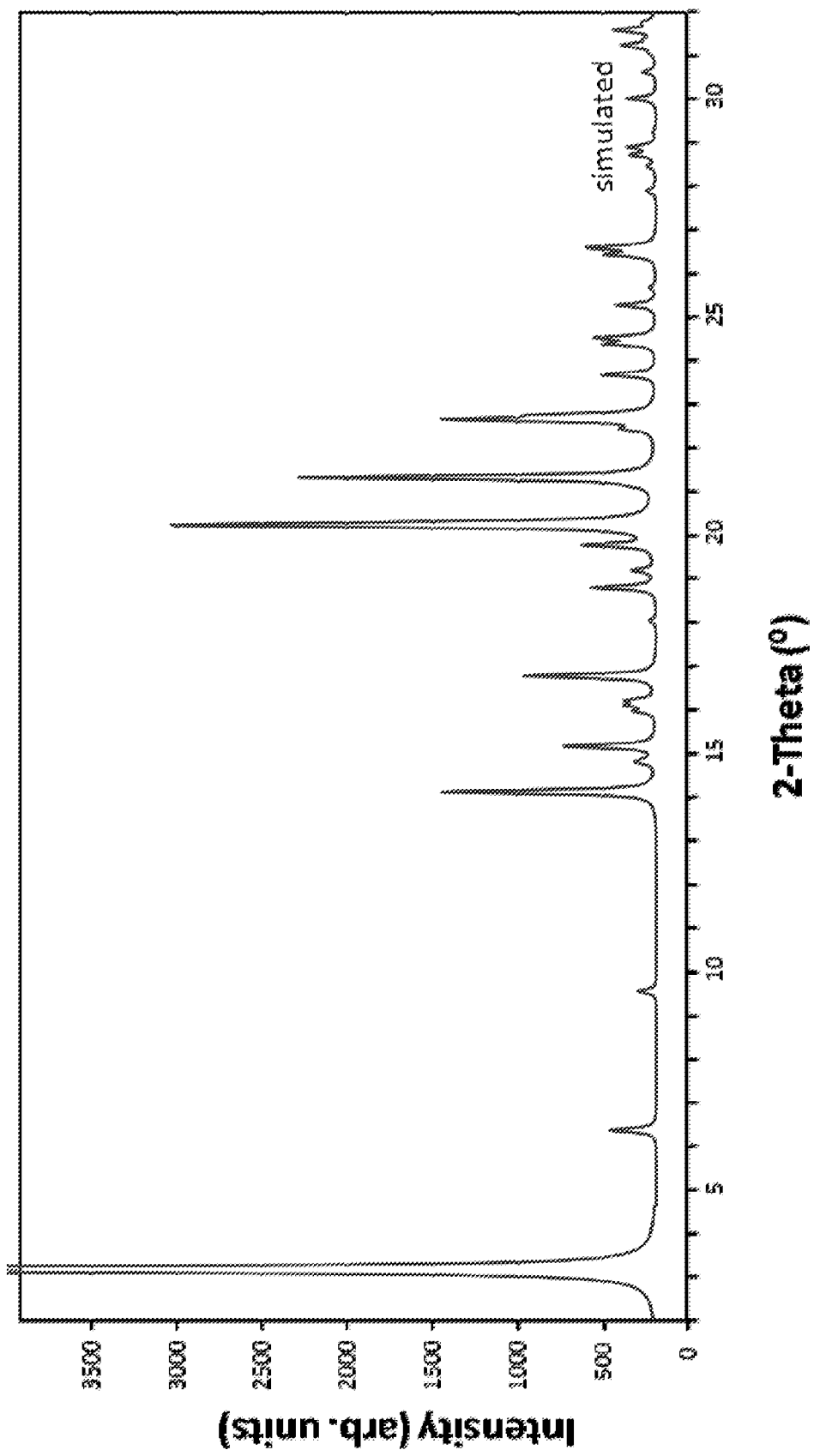
FIG. 3 shows the experimental and the simulated PXRD patterns (CuKα λ=1.5418 Å at approximately 25° C.) of the monohydrate H-2 Form of the mono-HCl salt of the compound of Example 2.

In another embodiment, the H-2 Form of Example 2, HCl salt is characterized by a simulated powder x-ray diffraction (PXRD) pattern substantially in accordance with the pattern shown in FIG. 3 and/or by an observed PXRD pattern substantially in accordance with the pattern shown in FIG. 3.

In yet another embodiment, the monohydrate H-2 form of the mono-HCl salt of Example 2 is characterized by a PXRD pattern (CuKα λ=1.5418 Å at a temperature of about 25° C.) comprising four or more, preferably five or more, 2θ values selected from: 3.2±0.2, 6.4±0.2, 9.6±0.2, 14.1±0.2, 15.2±0.2, 16.8±0.2, 18.8±0.2, 20.2±0.2, 21.3±0.2, 22.6±0.2, and 26.6±0.2, wherein the PXRD pattern is measured at a temperature of about 25° C.

In still yet an even further embodiment, the H-2 Form of Example 2, HCl salt is substantially pure.

In still yet another embodiment, the H-2 Form of Example 2, HCl salt contains at least about 90 wt. %, preferably at least about 95 wt. %, and more preferably at least about 99 wt. %, based on weight of the third crystalline form.

In yet another embodiment, a substantially pure H-2 Form of Example 2, HCl salt has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline H-2 Form of Example 2, HCl salt has substantially pure phase homogeneity with less than about 1% of the total peak area of the experimentally measured PXRD pattern arising from peaks that are absent from the simulated PXRD pattern.

In another embodiment, the third crystalline form of the compound of Example 2 consists essentially of H-2 Form of Example 2, HCl salt. The third crystalline form of this embodiment may comprise at least about 90 wt. %, preferably at least about 95 wt. %, and more preferably at least about 99 wt. %, based on the weight of the third crystalline form.

In one embodiment, the mono-hydrochloric acid salt of Example 2 is provided as neat crystalline material comprising one or more crystalline forms. Examples of suitable crystalline forms of the neat mono-hydrochloric acid salt of Example 2 include Forms N-3 and N-4.

In one embodiment, the neat mono-hydrochloric acid salt of Example 2 is provided in a fourth crystalline form referred to herein as "Form N-3" or "N-3 Form" of Example 2, HCl salt. The N-3 Form of Example 2, HCl salt comprises one molecule of HCl for each molecule of Example 2.

In one embodiment, the N-3 Form of the HCl salt of Example 2 is characterized by unit cell parameters approximately equal to the following:
Cell dimensions:
a=5.98 Å
b=7.24 Å
c=25.74 Å
α=90.0°
β=91.7°
γ=90.0°
Space group: $P2_1$
Molecules of Example 2/asymmetric unit: 1
Volume/number of molecules in the unit cell=556 Å$^3$
Density (calculated)=1.092 g/cm$^3$,
wherein the unit cell parameters of Form N-3 of the HCl salt of Example 2 are measured at a temperature of about 27° C.

In one embodiment, the N-3 Form of the HCl salt of Example 2 is characterized by unit cell parameters approximately equal to the following:
Cell dimensions:
a=5.93 Å
b=7.20 Å
c=25.24 Å
α=90.0°
β=90.2°
γ=90.0°
Space group: $P2_1$
Molecules of Example 2/asymmetric unit: 1
Volume/number of molecules in the unit cell=538 Å$^3$
Density (calculated)=1.128 g/cm$^3$,
wherein the unit cell parameters of Form N-3 of the HCl salt of Example 2 are measured at a temperature of about −70° C.

Figure 4:
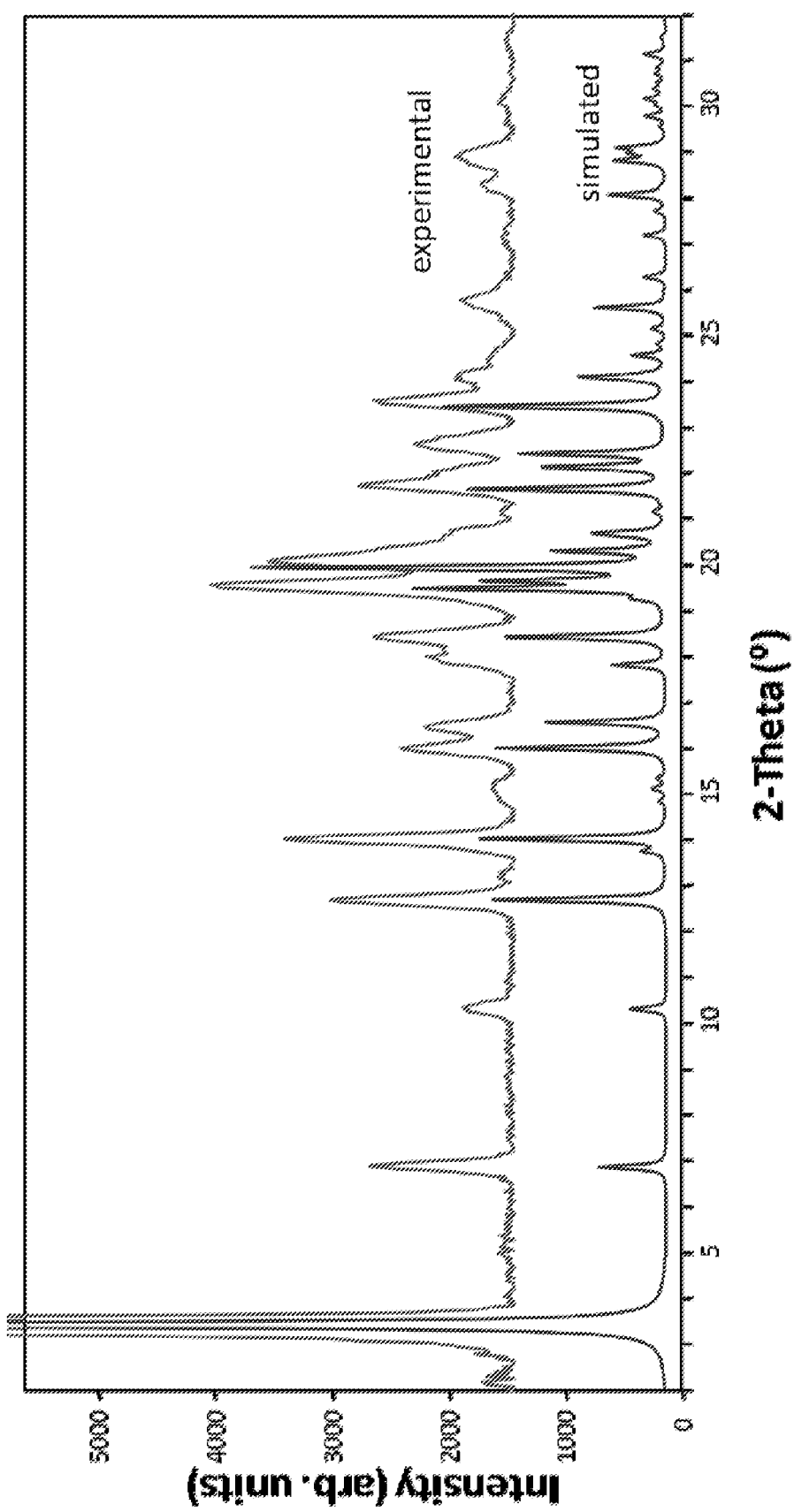
FIG. 4 shows the experimental and the simulated PXRD patterns (CuKα λ=1.5418 Å at approximately 25° C.) of the N-3 Form of the mono-HCl salt of the compound of Example 2.

In another embodiment, the N-3 Form of Example 2, HCl salt is characterized by a simulated powder x-ray diffraction (PXRD) pattern substantially in accordance with the pattern shown in FIG. 4 and/or by an observed PXRD pattern substantially in accordance with the pattern shown in FIG. 4.

In yet another embodiment, the N-3 form of the mono-HCl salt of Example 2 is characterized by a PXRD pattern (CuKα λ=1.5418 Å at a temperature of about 25° C.) comprising four or more, preferably five or more, 2θ values selected from:

3.4±0.2, 6.9±0.2, 10.4±0.2, 12.7±0.2, 14.0±0.2, 16.1±0.2, 19.7±0.2, 20.6±0.2, 22.1±0.2, and 24.0±0.2, wherein the PXRD pattern is measured at a temperature of about 25° C.

In still yet an even further embodiment, the N-3 Form of the HCl salt of Example 2 is substantially pure.

In still yet another embodiment, the N-3 Form of the HCl salt of Example 2 contains at least about 90 wt. %, preferably at least about 95 wt. %, and more preferably at least about 99 wt. %, based on weight of the fourth crystalline form, Form N-3.

In yet another embodiment, a substantially pure Form N-3 of the HCl salt of Example 2 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form N-3 of the HCl salt of Example 2 has substantially pure phase homogeneity with less than about 1% of the total peak area of the experimentally measured PXRD pattern arising from peaks that are absent from the simulated PXRD pattern.

In still yet an even further embodiment, the Form N-3 of the HCl salt of Example 2 is substantially pure.

In another embodiment, the crystalline form of Example 2 consists essentially of Form N-3. The crystalline form of this embodiment may comprise at least about 90 wt. %, preferably at least about 95 wt. %, and more preferably at least about 99 wt. %, based on the weight of the crystalline form, Form N-3 of Example 2.

In yet another embodiment, a pharmaceutical composition is provided comprising Form N-3 of Example 2; and at least one pharmaceutically-acceptable carrier and/or diluent.

In still another embodiment, a pharmaceutical composition comprises substantially pure Form N-3 of Example 2; and at least one pharmaceutically-acceptable carrier and/or diluent.

In still an even further embodiment, a therapeutically effective amount of Form N-3 of Example 2 is combined with at least one pharmaceutically acceptable carrier and/or diluent to provide at least one pharmaceutical composition.

In another embodiment, the fourth crystalline form of the HCl salt of Example 2 consists essentially of Form N-3. The fourth crystalline form of this embodiment may comprise at least about 90 wt. %, preferably at least about 95 wt. %, and more preferably at least about 99 wt. %, based on the weight of the fourth crystalline form, Form N-3.

In one embodiment, the neat mono-hydrochloric acid salt of Example 2 is provided in a fifth crystalline form referred to herein as "Form N-4" or "N-4 Form" of Example 2, HCl salt. The N-4 Form of Example 2, HCl salt comprises one molecule of HCl for each molecule of Example 2.

In one embodiment, the N-4 Form of the HCl salt of Example 2 is characterized by unit cell parameters approximately equal to the following:
Cell dimensions:
a=5.95 Å
b=7.27 Å
c=51.60 Å
α=90.0°
β=90.0°
γ=90.0°
Space group: P2$_1$2$_1$2$_1$
Molecules of Example 2/asymmetric unit: 1
Volume/number of molecules in the unit cell=558 Å$^3$
Density (calculated)=1.088 g/cm$^3$,
wherein the unit cell parameters of Form N-4 of Example 2, HCl salt are measured at a temperature of about 27° C.

In one embodiment, the N-4 Form of the HCl salt of Example 2 is characterized by unit cell parameters approximately equal to the following:
Cell dimensions:
a=5.92 Å
b=7.25 Å
c=50.61 Å
α=90.0°
β=90.0°
γ=90.0°
Space group: P2$_1$2$_1$2$_1$
Molecules of Example 2/asymmetric unit: 1
Volume/number of molecules in the unit cell=543 Å$^3$
Density (calculated)=1.119 g/cm$^3$,
wherein the unit cell parameters of Form N-4 of Example 2, HCl salt are measured at a temperature of about −70° C.

Figure 5:
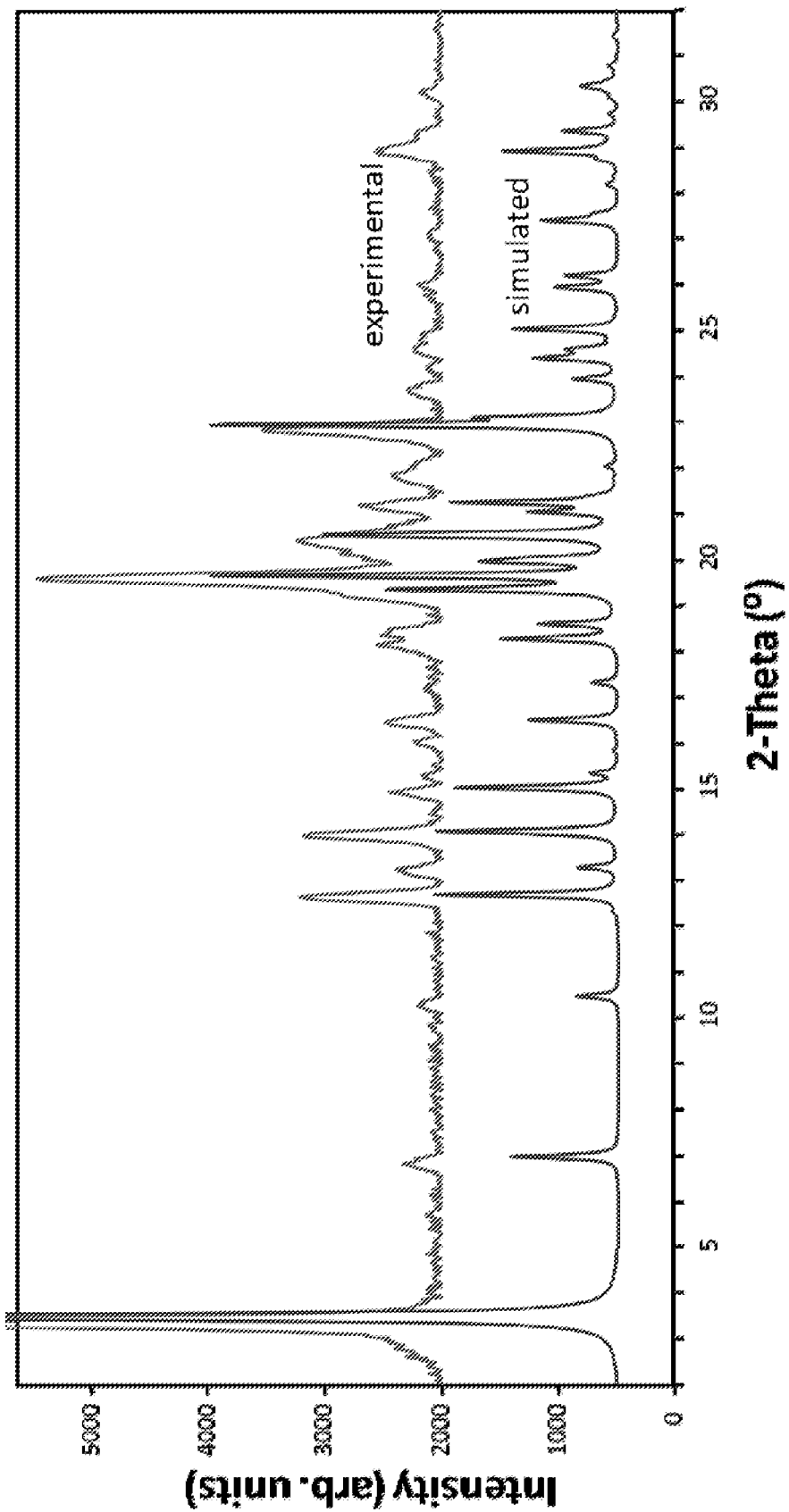
FIG. 5 shows the experimental and the simulated PXRD patterns (CuKα λ=1.5418 Å at approximately 25° C.) of the N-4 Form of the mono-HCl salt of the compound of Example 2.

In another embodiment, the N-4 Form of Example 2, HCl salt is characterized by a simulated powder x-ray diffraction (PXRD) pattern substantially in accordance with the pattern shown in FIG. 5 and/or by an observed PXRD pattern substantially in accordance with the pattern shown in FIG. 5.

In yet another embodiment, the N-4 form of the mono-HCl salt of Example 2 is characterized by a PXRD pattern (CuKα λ=1.5418 Å at a temperature of about 25° C.) comprising four or more, preferably five or more, 2θ values selected from: 3.4±0.2, 6.9±0.2, 10.3±0.2, 12.7±0.2, 13.3±0.2, 15.0±0.2, 19.7±0.2, 20.4±0.2, 21.2±0.2, 22.9±0.2, and 24.9±0.2, wherein the PXRD pattern is measured at a temperature of about 25° C.

In still yet an even further embodiment, the N-4 Form of the HCl salt of Example 2 is substantially pure.

In still yet another embodiment, the N-4 Form of the HCl salt of Example 2 contains at least about 90 wt. %, preferably at least about 95 wt. %, and more preferably at least about 99 wt. %, based on weight of the fourth crystalline form, Form N-4.

In yet another embodiment, a substantially pure Form N-4 of the HCl salt of Example 2 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially crystalline Form N-4 of the HCl salt of Example 2 has substantially pure phase homogeneity with less than about 1% of the total peak area of the experimentally measured PXRD pattern arising from peaks that are absent from the simulated PXRD pattern.

In still yet an even further embodiment, the Form N-4 of the HCl salt of Example 2 is substantially pure.

In another embodiment, the crystalline form of Example 2 consists essentially of Form N-4. The crystalline form of this embodiment may comprise at least about 90 wt. %, preferably at least about 95 wt. %, and more preferably at least about 99 wt. %, based on the weight of the crystalline form, Form N-4 of Example 2.

In yet another embodiment, a pharmaceutical composition is provided comprising Form N-4 of Example 2; and at least one pharmaceutically-acceptable carrier and/or diluent.

In still another embodiment, a pharmaceutical composition comprises substantially pure Form N-4 of Example 2; and at least one pharmaceutically-acceptable carrier and/or diluent.

In still an even further embodiment, a therapeutically effective amount of Form N-4 of Example 2 is combined with at least one pharmaceutically acceptable carrier and/or diluent to provide at least one pharmaceutical composition.

In one embodiment, a composition is provided comprising Form N-3, Form N-4, or a mixture thereof of the neat monohydrochloric acid salt of Example 2.

L-Malic Acid Salt

In one embodiment, the Example 2 is provided as an L-malic acid salt.

In one embodiment, the Example 2 is provided as a hemi-L-malic acid salt comprising 0.5 mole of L-malic acid for each mole of Example 2.

In one embodiment, the Example 2 is provided as a monohydrate hemi-L-malic acid salt comprising one mole of water and 0.5 mole of L-malic acid for each mole of Example 2.

In one embodiment, the monohydrate hemi-L-malic acid salt of Example 2 is provided in a sixth crystalline form referred to herein as "Form H-1" or "H-1 Form" of Example 2, hemi-L-malic acid salt. The H-1 Form of Example 2, hemi-L-malic acid salt comprises one molecule of water and 0.5 molecule of L-malic acid for each molecule of Example 2.

In one embodiment, the H-1 Form of the hemi-L-malic acid salt of Example 2 is characterized by unit cell parameters approximately equal to the following:

Cell dimensions:
a=6.13 Å
b=13.83 Å
c=28.75 Å
α=103.4°
β=94.0°
γ=92.6°
Space group: P1
Molecules of Example 2/asymmetric unit: 4
Volume/number of molecules in the unit cell=591 Å$^3$
Density (calculated)=1.165 g/cm$^3$, wherein the unit cell parameters of Form H-1 of the hemi-L-malic acid salt of Example 2 are measured at a temperature of about −70° C.

Figure 6:
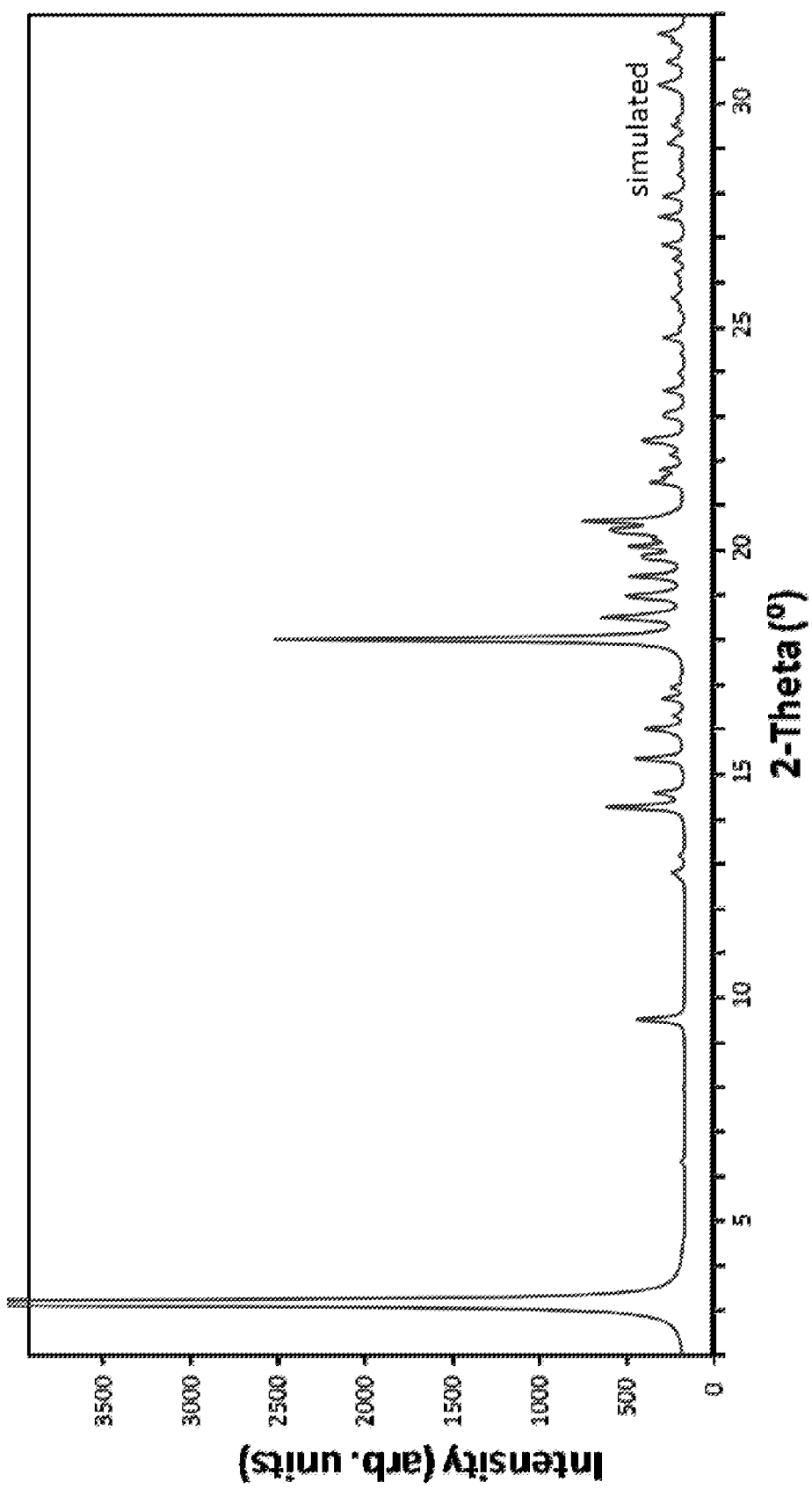
FIG. 6 shows the experimental and the simulated PXRD patterns (CuKα λ=1.5418 Å at approximately 25° C.) of the monohydrate H-1 Form of the hemi-L-malic salt of the compound of Example 2.

In another embodiment, the H-1 form of the hemi-L-malic acid salt of Example 2 is characterized by a simulated powder x-ray diffraction (PXRD) pattern substantially in accordance with the pattern shown in FIG. 6 and/or by an observed PXRD pattern substantially in accordance with the pattern shown in FIG. 6.

In yet another embodiment, the H-1 form of the hemi-L-malic acid salt of Example 2 is characterized by a PXRD pattern (CuKα λ=1.5418 Å at a temperature of about 25° C.) comprising four or more, preferably five or more, 2θ values selected from: 3.2±0.2, 6.3±0.2, 9.5±0.2, 12.8±0.2, 14.3±0.2, 18.0±0.2, 22.4±0.2, and 24.8±0.2, wherein the PXRD pattern is measured at a temperature of about 25° C.

Malonic Acid Salt

In one embodiment, the Example 2 is provided as a malonic acid salt.

In one embodiment, the Example 2 is provided as a hemi-malonic acid salt comprising 0.5 mole of malonic acid for each mole of Example 2.

In one embodiment, the Example 2 is provided as a monohydrate hemi-malonic acid salt comprising one mole of water and 0.5 mole of malonic acid for each mole of Example 2.

In one embodiment, the monohydrate hemi-malonic acid salt of Example 2 is provided in a seventh crystalline form referred to herein as "Form H-1" or "H-1 Form" of Example 2, hemi-malonic acid salt. The H-1 Form of Example 2, hemi malonic acid salt comprises one molecule of water and 0.5 molecule of malonic acid for each molecule of Example 2.

In one embodiment, the H-1 Form of the hemi-malonic acid salt of Example 2 is characterized by unit cell parameters approximately equal to the following:

Cell dimensions:
a=14.73 Å
b=6.27 Å
c=25.36 Å
α=90.0°
β=93.8°
γ=90.0°
Space group: P2$_1$
Molecules of Example 2/asymmetric unit: 2
Volume/number of molecules in the unit cell=584 Å$^3$
Density (calculated)=1.137 g/cm$^3$, wherein the unit cell parameters of Form H-1 are measured at a temperature of about −70° C.

Figure 7:
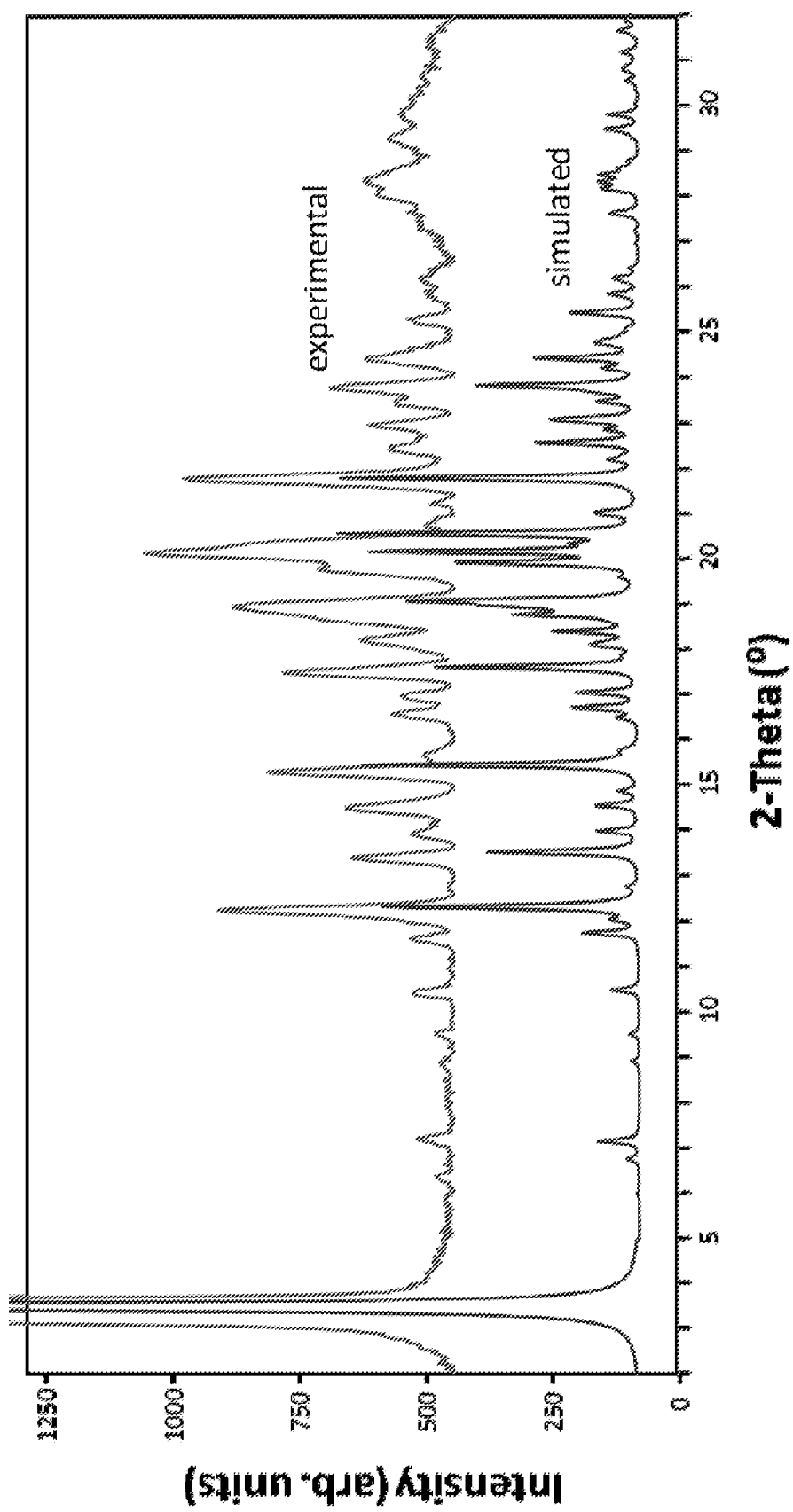
FIG. 7 shows the experimental and the simulated PXRD patterns (CuKα λ=1.5418 Å at approximately 25° C.) of the monohydrate H-1 Form of the hemi-malonic salt of the compound of Example 2.

In another embodiment, the H-1 form of the hemi-malonic acid salt of Example 2 is characterized by a simulated powder x-ray diffraction (PXRD) pattern substantially in accordance with the pattern shown in FIG. 7 and/or by an observed PXRD pattern substantially in accordance with the pattern shown in FIG. 7.

In yet another embodiment, the H-1 form of the hemi-malonic acid salt of Example 2 is characterized by a PXRD pattern (CuKα λ=1.5418 Å at a temperature of about 25° C.) comprising four or more, preferably five or more, 2θ values selected from: 3.5±0.2, 7.1±0.2, 12.3±0.2, 13.5±0.2, 15.5±0.2, 17.6±0.2, 19.1±0.2, 20.2±0.2, 20.6±0.2, 21.7±0.2, and 23.8±0.2, wherein the PXRD pattern is measured at a temperature of about 25° C.

Phosphoric Acid Salt

In one embodiment, the Example 2 is provided as a phosphoric acid salt.

In one embodiment, the Example 2 is provided as a 1/3-hydrate phosphoric acid salt.

In one embodiment, the Example 2 is provided as a phosphoric acid salt comprising 0.67 mole of phosphoric acid for each mole of Example 2.

In one embodiment, the Example 2 is provided as a 1/3-hydrate phosphoric acid salt comprising 0.33 mole of water and 0.67 mole of phosphoric acid for each mole of Example 2.

In one embodiment, the 1/3-hydrate phosphoric acid salt of Example 2 is provided in an eighth crystalline form referred to herein as "Form H.33-1" or "H.33-1 Form" of Example 2, phosphoric acid salt. The H.33-1 Form of Example 2, phosphoric acid salt comprises 0.33 molecule of water and 0.67 molecule of phosphoric acid for each molecule of Example 2.

In one embodiment, the H.33-1 Form is characterized by unit cell parameters approximately equal to the following:

Cell dimensions:
a=59.12 Å
b=6.89 Å
c=16.62 Å
α=90.0°
β=94.7°
γ=90.0°
Space group: C2
Molecules of Example 2/asymmetric unit: 3
Volume/number of molecules in the unit cell=563 Å$^3$
Density (calculated)=1.181 g/cm$^3$, wherein the unit cell parameters of Form H.33-1 are measured at a temperature of about −70° C.

Figure 8:
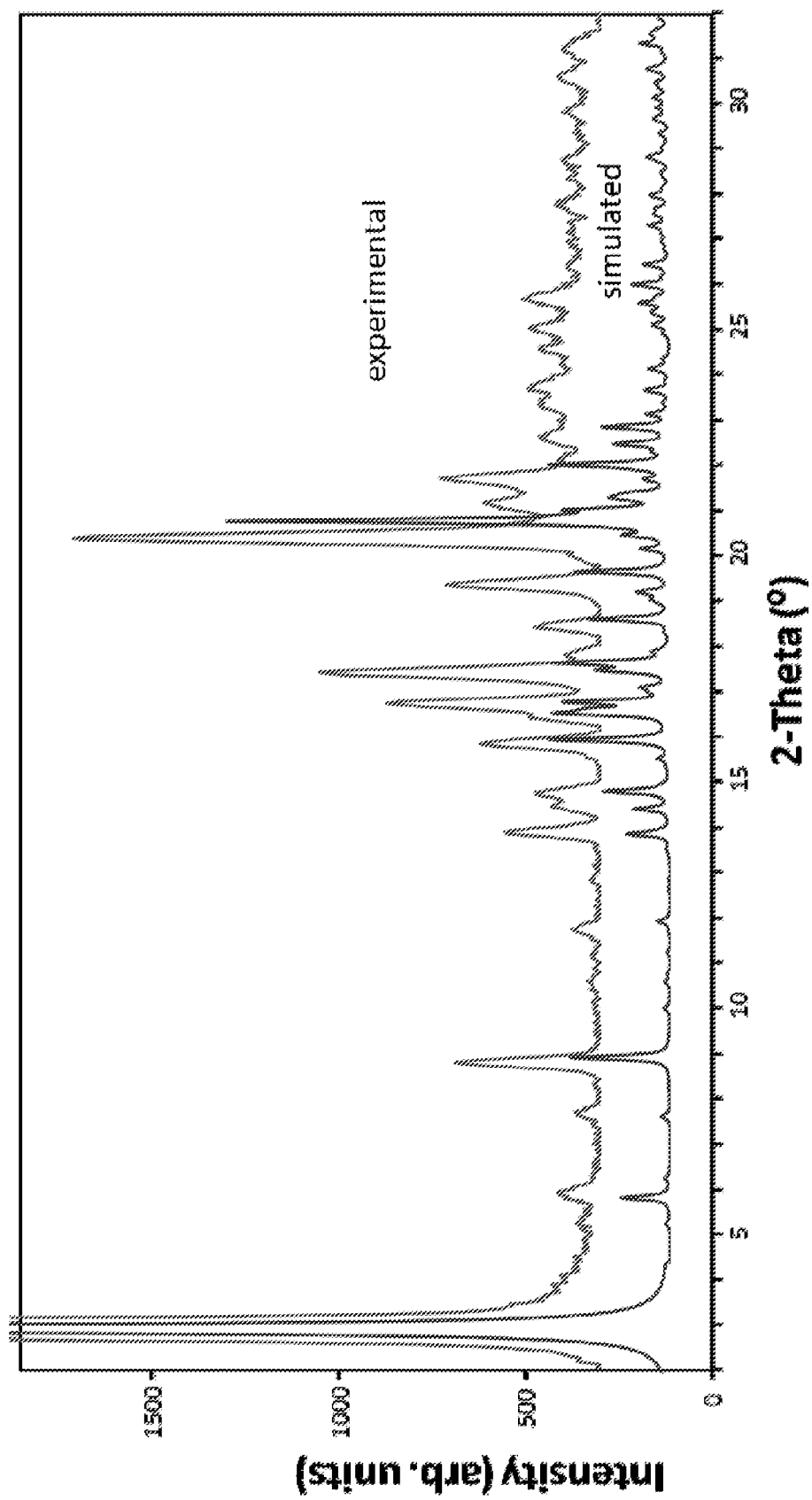
FIG. 8 shows the experimental and the simulated PXRD patterns (CuKα λ=1.5418 Å at approximately 25° C.) of the 1/3-hydrate H.33-1 Form of the 2/3 phosphoric acid salt of the compound of Example 2.

In another embodiment, the H.33-1 form of the 1/3-phosphoric acid salt of Example 2 is characterized by a simulated powder x-ray diffraction (PXRD) pattern substantially in accordance with the pattern shown in FIG. 8 and/or by an observed PXRD pattern substantially in accordance with the pattern shown in FIG. 8.

In yet another embodiment, the H.33-1 form of the 1/3-phosphoric acid salt of Example 2 is characterized by a PXRD pattern (CuKα λ=1.5418 Å at a temperature of about 25° C.) comprising four or more, preferably five or more, 2θ values selected from: 2.9±0.2, 5.9±0.2, 8.8±0.2, 13.9±0.2, 15.8±0.2, 16.7±0.2, 17.4±0.2, 18.4±0.2, 19.4±0.2, and 20.4±0.2, wherein the PXRD pattern is measured at a temperature of about 25° C.

R-(+)-Mandelic Acid Salt

In one embodiment, the Example 2 is provided as an R-(+)-mandelic acid salt.

In one embodiment, the Example 2 is provided as a monohydrate R-(+)-mandelic acid.

In one embodiment, the Example 2 is provided as an R-(+)-mandelic acid salt comprising one mole of R-(+)-mandelic acid for each mole of Example 2.

In one embodiment, the Example 2 is provided as a monohydrate R-(+)-mandelic acid salt comprising one mole of water and one mole of R-(+)-mandelic acid for each mole of Example 2.

In one embodiment, the monohydrate R-(+)-mandelic acid salt of Example 2 is provided in an ninth crystalline form referred to herein as "Form N-1" or "N-1 Form" of Example 2, R-(+)-mandelic acid salt. The N-1 Form of Example 2, R-(+)-mandelic acid salt comprises one molecule of water and one molecule of R-(+)-mandelic acid for each molecule of Example 2.

In one embodiment, the N-1 Form of Example 2, R-(+)-mandelic acid salt is characterized by unit cell parameters approximately equal to the following:

Cell dimensions:
a=6.31 Å
b=10.03 Å
c=21.79 Å
α=98.2°
β=91.3°
γ=91.7°
Space group: P1
Molecules of Example 2/asymmetric unit: 2
Volume/number of molecules in the unit cell=683 Å$^3$
Density (calculated)=1.171 g/cm$^3$,
wherein the unit cell parameters of Form N-1 of Example 2, R-(+)-mandelic acid salt are measured at a temperature of about −70° C.

Figure 9:
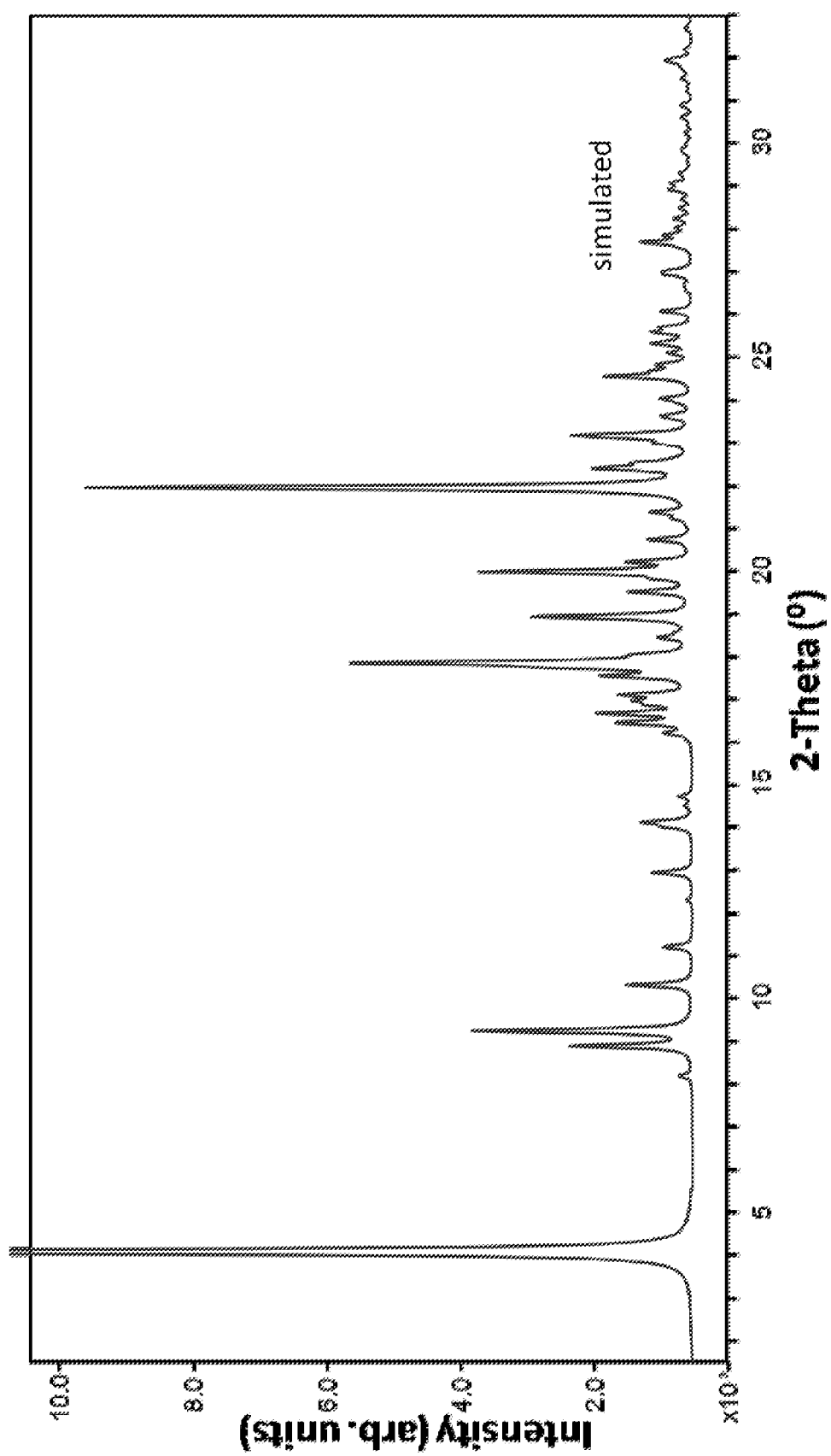
FIG. 9 shows the simulated PXRD pattern, calculated at −70° C. (CuKα λ=1.5418 Å) of the N-1 Form of the R-(+)-mandelic acid salt of the compound of Example 2.

In another embodiment, the N-1 Form of Example 2, R-(+)-mandelic acid salt is characterized by a simulated powder x-ray diffraction (PXRD) pattern substantially in accordance with the pattern shown in FIG. 9.

In still yet an even further embodiment, the N-1 Form of Example 2, R-(+)-mandelic acid salt is substantially pure.

In still yet another embodiment, the N-1 Form of Example 2, R-(+)-mandelic acid salt contains at least about 90 wt. %, preferably at least about 95 wt. %, and more preferably at least about 99 wt. %, based on weight of the Form N-1 of Example 2, R-(+)-mandelic acid salt.

In yet another embodiment, a substantially pure Form N-1 of Example 2, R-(+)-mandelic acid salt has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure crystalline Form N-1 of Example 2, R-(+)-mandelic acid salt has substantially pure phase homogeneity with less than about 1% of the total peak area of the experimentally measured PXRD pattern arising from peaks that are absent from the simulated PXRD pattern.

In another embodiment, the crystalline form of Example 2, R-(+)-mandelic acid salt consists essentially of Form N-1. The crystalline form of this embodiment may comprise at least about 90 wt. %, preferably at least about 95 wt. %, and more preferably at least about 99 wt. %, based on the weight of the crystalline form, Form N-1 of Example 2, R-(+)-mandelic acid salt.

In yet another embodiment, a pharmaceutical composition is provided comprising Form N-1 of Example 2, R-(+)-mandelic acid salt; and at least one pharmaceutically-acceptable carrier and/or diluent.

In still another embodiment, a pharmaceutical composition comprises substantially pure Form N-1 of Example 2, R-(+)-mandelic acid salt; and at least one pharmaceutically-acceptable carrier and/or diluent.

In still an even further embodiment, a therapeutically effective amount of Form N-1 of Example 2, R-(+)-mandelic acid salt is combined with at least one pharmaceutically acceptable carrier and/or diluent to provide at least one pharmaceutical composition.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

Listed below are definitions of various terms used to describe the present invention. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

Throughout the specification, groups and substituents thereof may be chosen by one skilled in the field to provide stable moieties and compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s)" may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology,* 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, juvenile idiopathic arthritis, systemic lupus erythematosus, cutaneous lupus erythematosus (discoid lupus erythematosus, subacute lupus erythematosus) and lupus nephritis, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis including ANCA-associated vasculitis, giant cell arteritis, Takayasu's arteritis, microscopic poliangiitis, central nervous system vasculitis, Churg-Strauss Syndrome, and rheumatoid vasculitis, erythema, cutaneous eosinophilia, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderrna and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, chronic bacterial infection, thrombocytopenia, IgA nephropathy, mesangioproliferative glomerulonephritis, IgG4-related disease, ankylosing spondylitis, and relapsing polychondritis. Juvenile idiopathic arthritis includes oligoarthritis-onset juvenile idiopathic arthritis, polyarthritis-onset juvenile idiopathic arthritis, systemic-onset juvenile idiopathic arthritis, juvenile psoriatic arthritis, and enthesitis-related juvenile idiopathic arthritis.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

In another embodiment, a method for treating inflammatory bowel disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of inflammatory bowel disease. In another embodiment, provided is the use of the compounds of Formula (I) or pharmaceutically acceptable salts thereof, for the manufacture of a medicament for treatment of inflammatory bowel disease. A therapeutically effective amount may be employed in these embodiments. Preferably, in these embodiments, the inflammatory bowel disease is selected from Crohn's disease, ulcerative colitis, collagenous colitis, lymphocytic colitis, ischaemic colitis, diversion colitis, Behçet's disease, and indeterminate colitis.

In another embodiment, a method for treating lupus is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of lupus. In another embodiment, provided is the use of the compounds of Formula (I) or pharmaceutically acceptable salts thereof, for the manufacture of a medicament for treatment of lupus. A therapeutically effective amount may be employed in these embodiments. Lupus includes systemic lupus erythematosus, cutaneous lupus erythematosus, discoid lupus erythematosus, subacute lupus erythematosus and lupus nephritis.

In another embodiment, a method for treating multiple sclerosis is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of multiple sclerosis. In another embodiment, provided is the use of the compounds of Formula (I) or pharmaceutically acceptable salts thereof, for the manufacture of a medicament for treatment of multiple sclerosis. A therapeutically effective amount may be employed in these embodiments. Preferably, in these embodiments, multiple sclerosis includes relapsing remitting multiple sclerosis, primary progressive multiple sclerosis, secondary progressive multiple sclerosis, and progressive relapsing multiple sclerosis.

The methods of treating S1P1-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the S1P1 receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo[1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

Ac acetyl
anhyd. anhydrous
aq. aqueous
Bn benzyl
Bu butyl
Boc tert-butoxycarbonyl
CV Column Volumes
DCM dichloromethane
DEA diethylamine
DMA N,N-dimethylacetamide
DMF dimethylformamide
DMPU 1,3-dimethyl-3,4,5,6-tetrahydro-2(1H)-pyrimidinone
DMSO dimethylsulfoxide
EtOAc ethyl acetate
Et ethyl
$Et_3N$ triethyl amine
EtOH ethanol
H or $H_2$ hydrogen
h, hr or hrs hour(s)
hex hexane
iso
HOAc acetic acid
HPLC high pressure liquid chromatography
LC liquid chromatography
LDA lithium diisopropylamide
LiHMDS lithium bis(trimethylsilyl)amide
M molar
mM millimolar
Me methyl
MeCN acetonitrile
MeOH methanol
MHz megahertz
min. minute(s)
mins minute(s)
$M^{+1}$ $(M+H)^+$
MS mass spectrometry
n or N normal
nM nanomolar
NMP N-methylpyrrolidine
Pd/C palladium on carbon
$Pd_2(dba)_3$ tris-(dibenzylideneacetone)dipalladium
Ph phenyl
Pr propyl
PSI pounds per square inch
R-BINAP (R)-(+)-2,2'-bis(diphenylphosphino)-1,1'-binaphthyl
Ret Time or RT retention time
sat. saturated
S-BINAP (S)-(−)-2,2'-bis(diphenylphosphino)-1,1'-binaphthyl
SFC supercritical fluid chromatography
TFA trifluoroacetic acid
THF tetrahydrofuran
HPLC Conditions:
Condition C: Column: YMC COMBISCREEN® S5 50×4.6 mm (Linear gradient of 0 to 100% Solvent B over 4 min, then 1-4 min hold at 100% B; Solvent A=water 90%/MeOH 10%/$H_3PO_4$, 0.2%; Solvent B=MeOH 90%/water 10%/$H_3PO_4$ 0.2%. Flow rate: 4 mL/min; Products detected at 220 nm.
Condition G: Column: Waters Acquity BEH C18 2.1×50 mm 17 μm; Linear gradient of 0-100% Solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.
Condition H: Column: SunFire C18, (150×3.0 mm), 3.5 μm; Linear gradient of 10 to 100% Solvent B over 25 min, then 5 min hold at 100% B; Flow rate: 1 mL/min; Buffer: 0.5% TFA, in water with pH adjusted to 2.5 using dilute ammonia; Solvent A: Buffer:acetonitrile (95:5); Solvent B: Buffer:acetonitrile (5:95); Products detected at 220 nm.

Condition I: Column: Waters Acquity SD BEH C18, 2.1× 50 mm, 1.7-μm particles; Mobile Phase A: 100% $H_2O$ with 0.05% TFA; Mobile Phase B: 100% acetonitrile with 0.05% TFA; Temperature: 50° C.; gradient of 98:2 to 2:98 (A %:B %) over 1 min and hold 2:98 for 0.5 min.; Flow: 0.800 mL/min Products detected at 220 nm.

Condition J: Column: CHROMOLITH® SpeedROD (4.6× 50 mm); Linear gradient of 0 to 100% Solvent B over 4 min, with 1 min hold at 100% B; Solvent A: 10% MeOH, 90% $H_2O$, 0.1% TFA; Solvent B: 90% MeOH, 10% $H_2O$, 0.1% TFA; Flow rate: 4 mL/min; Products detected at 220 nm.

Intermediate 1

(1R,3S)-Methyl 1-amino-3-(4-bromophenyl)cyclopentanecarboxylate

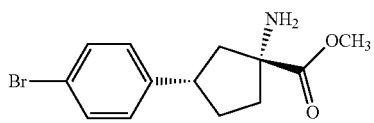

(I-1)

Intermediate 1A: (S)-3-(4-Bromophenyl)cyclopentanone

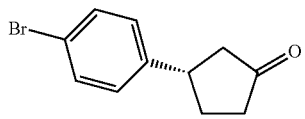

(I-1A)

A solution of 4-bromophenylboronic acid (20 g, 100 mmol) in 1,4-dioxane (120 mL) in a 500 ml flask was purged with nitrogen for 5 mins S-BINAP (0.992 g, 1.593 mmol) and bis(norbornadiene)rhodium (I) tetrafluoroborate (0.559 g, 1.494 mmol) were added sequentially to the solution under a positive pressure of nitrogen. After 2 hours of agitation at room temperature, water (20 mL) was added followed by cyclopent-2-enone (8.06 mL, 100 mmol) and $Et_3N$ (13.88 mL, 100 mmol). The mixture was allowed to stir at room temperature for 16 hours. The resulting dark solids were removed by filtration and the filtrate was poured into 250 ml of ethyl acetate. The solution was washed with water twice and the organic layer was concentrated. The residue was purified by flash column chromatography (split into two batches, each run on a 330 g silica column 0%-25% ethyl acetate in hexane) to afford 12.1 grams of (S)-3-(4-bromophenyl)cyclopentanone. HPLC purity was >98% and Chiral HPLC analysis indicated approximately 90% ee. The material was further purified under the Chiral SFC conditions described below. Experimental Details: Instrument: Berger SFC MGIII; Preparative Conditions Column: CHIRAL-PAK® AD-H 25×5 cm, 5 μm; Column Temperature: 40° C.; Flow rate: 200 mL/min; Mobile Phase: $CO_2$/MeOH=80/20; Detector Wavelength: 225 nm; Injection Vol.: 1.0 mL; Sample Preparation: 12.1 g in; 210 mL MeOH (Conc. 60 mg/ml); Analytical Conditions: Column: CHIRALPAK® AD 25×0.46 cm, 10 μm; Column Temperature: 40° C.; Flow rate: 2.0 min; Mobile Phase: $CO_2$/MeOH=70/30; Detector Wavelength: 220 nm; Injection Vol.: 5 μL.

The desired enantiomer (major isomer) was isolated and named as "PK2" based on the elution order. The enantiomeric purity of the isolated isomer was determined to be greater than 99.6% on SFC/UV area % at 220 nm. After evaporation, 10.5 grams of the desired enantiomer were recovered. HPLC retention time=LC/MS $M^{+1}$=239/241. $^1$H NMR (400 MHz, $CD_3OD$) δ ppm 7.43-7.51 (2H, m), 7.10-7.19 (2H, m), 3.32-3.46 (1H, m), 2.67 (1H, dd, J=18.27, 7.48 Hz), 2.39-2.54 (2H, m), 2.23-2.39 (2H, m), 1.97 (1H, ddd, J=12.98, 11.00, 9.02 Hz).

Intermediate 1B: (7S)-7-(4-Bromophenyl)-1,3-diazaspiro[4.4]nonane-2,4-dione

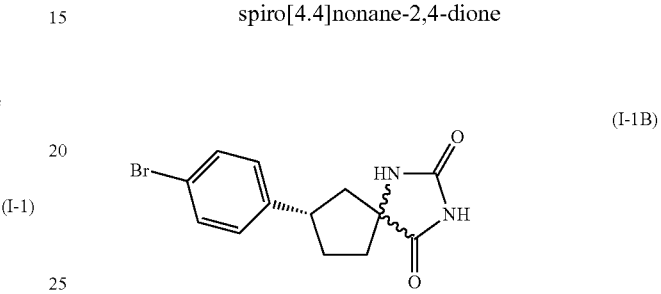

(I-1B)

A total of 9.8 g (S)-3-(4-bromophenyl)cyclopentanone was used, divided into 2 batches each containing 4.9 g. The two batches were processed under identical conditions as described below.

To a mixture of (S)-3-(4-bromophenyl)cyclopentanone (I-1A, 4.9 g, 20.49 mmol) and potassium cyanide (1.935 g, 29.7 mmol) in EtOH (40 mL) and water (20 mL) in a glass pressure vessel was added ammonium carbonate (4.92 g, 51.2 mmol). The reaction vessel was sealed and placed in an oil bath heated at 80° C. for 24 hours, resulting in the formation of a white solid. After cooling the reaction vessel in an ice bath, the vessel was opened and 30 ml of water was added resulting in the formation of additional solids. The solids were collected by filtration, washed twice with 5 ml water, and then dried under high vacuum. The two batches were combined to provide 13.9 g of (7S)-7-(4-bromophenyl)-1,3-diazaspiro[4.4]nonane-2,4-dione) which were used for subsequent reactions without further purification. HPLC retention time=0.82 min (Condition G) LC/MS $M^{+Na}$=331, $2M^{+H}$=619.

Intermediate 1C: (3S)-1-Amino-3-(4-bromophenyl) cyclopentanecarboxylic acid

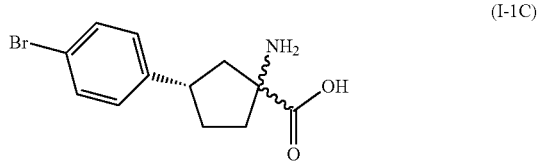

(I-1C)

To (7S)-7-(4-bromophenyl)-1,3-diazaspiro[4.4]nonane-2, 4-dione (I-1B, 13.9 g, 45.0 mmol) in 1,4-dioxane (40 mL) in a round bottom flask was added aqueous NaOH (2N, 100 mL, 200 mmol). The mixture was heated to 95° C. and stirred for 24 hours. Additional NaOH (25 mL, 50 mmol) was added and heating continued for another two days. The solution was cooled with an ice-bath, neutralized with 5N HCl to approximately pH 7 resulting in the formation of a white precipitate. The solids were collected by filtration and dried under high vacuum for 2 days to provide 14 g of (3S)-1-amino-3-(4-bromophenyl)cyclopentanecarboxylic acid as a white solid which was used as such for the subsequent step without further purification. HPLC retention time=0.64 min (Condition G) LC/MS M$^{+1}$=284/286.

Intermediate 1D: (3S)-Methyl 1-amino-3-(4-bromophenyl)cyclopentanecarboxylate

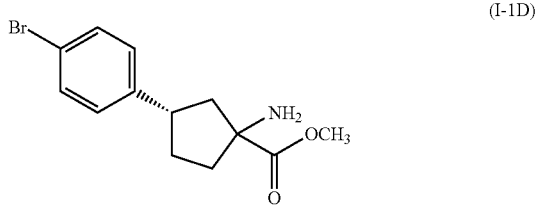 [SMILES: COC(=O)C1(N)CC[C@H](c2ccc(Br)cc2)C1]

(I-1D)

To a heterogeneous mixture of (3S)-1-amino-3-(4-bromophenyl)cyclopentanecarboxylic acid (I-1C, 14 g, 49.3 mmol) in MeOH (250 mL) was added thionyl chloride (36.0 mL, 493 mmol) dropwise over a period of 20 minutes at room temperature via an additional funnel (exothermic). The reaction mixture was placed in an oil bath and heated to 70° C. for 4 hours. The solvent was removed under vacuum, with the residue being dissolved in ethyl acetate (200 mL) and washed twice with 1N NaOH. The organic layer was then dried over Na$_2$SO$_4$ and concentrated to give 10.8 g of (3S)-methyl 1-amino-3-(4-bromophenyl)cyclopentanecarboxylate. HPLC retention time=0.68 min (Condition G); LC/MS M$^{+1}$=298/300.

Intermediate 1: (1R,3S)-Methyl 1-amino-3-(4-bromophenyl)cyclopentanecarboxylate (I-1)

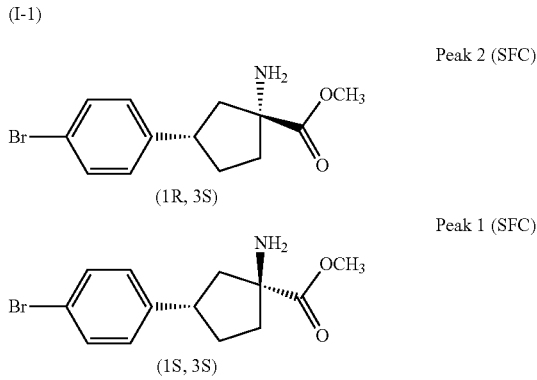

Peak 2 (SFC)

(1R, 3S)

Peak 1 (SFC)

(1S, 3S)

The mixture of diastereomers (I-1D, 9.5 g) was separated by Chiral SFC. The absolute stereochemical assignment of Intermediate 1 and its diastereomer was previously described (Wallace, G. A. et al., *J. Org. Chem.*, 74:4886-4889 (2009)). Experimental Details: Instrument: Preparative: Thar SFC350; Analytical: Berger analytical SFC; Preparative Conditions: Column: Lux-Cellulose-4 25×3 cm, 5 µm; Column Temperature: 35° C.; Flow rate: 200 ml/min; Mobile Phase: CO$_2$/(MeOH with 0.1% DEA)=87/13; Detector Wavelength: 220 nm; Injection Vol.: 0.6 ml; Sample Preparation: 9.5 g in 400 ml MeOH (Conc. 23.7 mg/ml). Analytical Conditions: Column: Lux-Cellulose-4 25×0.46 cm, 5 µm; Column Temp. 35° C.; Flow rate: 3 ml/min; Mobile Phase: CO$_2$/(MeOH with 0.1% DEA)=85/15; Detector Wavelength: 220 nm; Injection Vol.: 5 µL.

Intermediate 1: Peak 2: 4.06 g; ret. time=6.64 min on the analytical chiral SFC conditions above. Optical purity: 98.2%; LC/MS M$^{+1}$=298/300; Peak 1: 3.96 g; ret. time=5.47 min on the analytical chiral SFC conditions above. Optical purity: 99.4%.

Alternative Preparation: HCl Salt of Intermediate 1

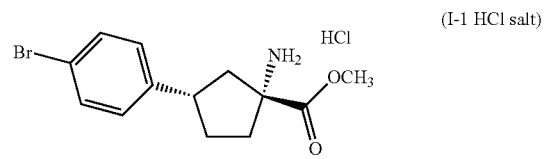 [SMILES: COC(=O)[C@@]1(N)CC[C@H](c2ccc(Br)cc2)C1 ; Cl]

(I-1 HCl salt)

A solution of (3S)-1-amino-3-(4-bromophenyl)cyclopentanecarboxylic acid (10.2 g, 35.9 mmol) in MeOH (100 mL) was cooled in an ice bath, followed by addition of SOCl$_2$ (15.72 mL, 215 mmol) dropwise. After the addition was complete, the solution was refluxed for 3 hrs at which time the reaction was determined to be complete by HPLC. The solution was concentrated to remove methanol to afford a solid. The solid was taken in 50 ml of 3% H$_2$O in EtOAc and stirred well for 30 mins. The white solid formed was collected by filtration. The wet white solid was taken in 50 ml of 4% H$_2$O in 1,2-dimethoxyethane and heated to 50° C. for 3 hrs, and then stirred at room temperature overnight. The resulting white solid was collected by filtration and dried to afford (1R,3S)-methyl 1-amino-3-(4-bromophenyl)cyclopentanecarboxylate hydrochloride (3.5 g, 10.35 mmol). HPLC retention time=6.6 min (Condition H) LC/MS M$^{+1}$=298/300. $^1$H NMR (400 MHz, DMSO-d$_6$) δ 8.95 (br. s, 3H) 7.50-7.53 (m, 2H), 7.35-7.37 (m, 2H), 3.81 (s, 3H) 3.17-3.28 (m, 1H), 2.57 (dd, J=14, 7 Hz, 1H), 2.0-2.28 (m, 5H).

Intermediate 2

(1R,3R)-Methyl 1-amino-3-(4-bromophenyl)cyclopentanecarboxylate (I-2)

Intermediate 2A: (R)-3-(4-Bromophenyl)cyclopentanone (I-2A)

A solution of 4-bromophenylboronic acid (20 g, 100 mmol) in 1,4-dioxane (120 mL) was purged with nitrogen for 10 min. (R)-BINAP (0.992 g, 1.593 mmol) and bis(norbornadiene)rhodium (I) tetrafluoroborate (0.559 g, 1.494 mmol) were added sequentially, and the suspension was sonicated for 5 min. The mixture was stirred for 20 min. Water (20 mL) was added, and the reaction mixture became homogeneous. After 10 minutes, cyclopent-2-enone (8.06 mL, 100 mmol) was added, and the reaction mixture was stirred at room temperature overnight. HPLC and LCMS analysis indicated that the reaction had proceeded, but there was more starting material than product. The reaction mixture was filtered through a pad of CELITE®, and the CELITE® was washed with ethyl acetate (100 mL). The filtrate was diluted with an additional ethyl acetate (150 mL), washed with water (2×), washed with brine, and dried over anhydrous sodium sulfate. The product mixture was purified by flash silica gel chromatography using a mixture of ethyl acetate and hexane to give (R)-3-(4-bromophenyl)cyclopentanone (6.09 g, 25.5 mmol) as a white solid. The product was 98% pure by HPLC with a retention time=2.11 min.—(Condition J). LC/MS $M^{+1}$=241 $^1$H NMR (400 MHz, chloroform-d) δ 7.57-7.39 (m, 2H), 7.22-7.06 (m, 2H), 3.39 (ddd, J=10.9, 6.8, 4.1 Hz, 1H), 2.67 (dd, J=18.2, 7.4 Hz, 1H), 2.57-2.38 (m, 2H), 2.38-2.21 (m, 2H), 1.99-1.85 (m, 1H).

Chiral HPLC indicated that the compound was 90-95% enantiomerically pure. The compound (6.03 g) was further purified by Chiral SFC using the conditions listed below. The desired enantiomer was isolated and named as "PK1" in the elution order. The enantiomeric purity of the isolated isomer was determined to be greater than 99.9% on SFC/UV area % at 220 nm. 5.45 grams of the desired enantiomer was recovered after concentration. Experimental Details: Instrument: Berger SFC MGIII; Prep. Conditions; Column: CHIRALPAK® AD-H 25×3 cm, 5um; Column Temperature: 40° C.; Flow rate: 180 mL/min; Mobile Phase: CO$_2$/MeOH=87/13; Detector Wavelength: 225 nm; Injection Vol.: 0.5 mL; Sample Preparation: 6.03 g in 100 mL MeOH (Conc. 60 mg/ml). Analytical Conditions: Column: CHIRALPAK® AD 25×0.46 cm, 10 µm; Column Temperature: 40° C.; Flow rate: 2.0 min; Mobile Phase: CO$_2$/MeOH=70/30; Detector Wavelength: 220 nm; Injection Vol.: 5 µL.

Intermediate 2B: (7R)-7-(4-Bromophenyl)-1,3-diazaspiro[4.4]nonane-2,4-dione

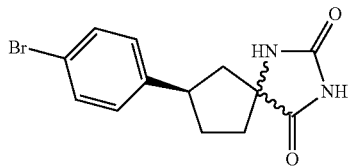

(I-2B)

To a mixture of (R)-3-(4-bromophenyl)cyclopentanone (I-2A, 5.4 g, 22.58 mmol) and potassium cyanide (2.132 g, 32.7 mmol) in EtOH (40 mL) and water (20 mL) in a glass pressure vessel was added ammonium carbonate (5.42 g, 56.5 mmol). The reaction vessel was sealed and placed in an oil bath heated at 80° C. for 20 hours. A large amount of white, free flowing solid formed in the pale yellow solution. Analysis by LCMS indicated remaining starting material so the reaction was continued for an additional 24 hours. As conversion was incomplete, the temperature of the oil bath was raised to 120° C. The white solid completely dissolved at the higher temperature. After 3 hours the solution was cooled down to room temperature. The solution was further cooled in an ice bath, water (30 mL) was added and the resulting white solid was collected by filtration, washed with water, air dried, then placed under high vacuum to afford the target compound (6.9 g, 22.32 mmol) which was used for subsequent reaction without additional purification. HPLC retention time=0.81 min (Condition G); LC/MS $M^H$=309/311; $2M^{+H}$=619.

Intermediate 2C: (3R)-1-Amino-3-(4-bromophenyl)cyclopentanecarboxylic acid

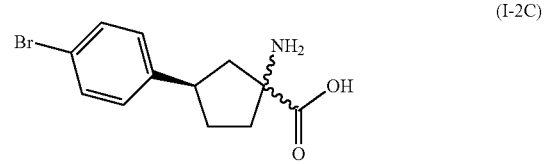

(I-2C)

A solution of (7R)-7-(4-bromophenyl)-1,3-diazaspiro[4.4]nonane-2,4-dione (I-2B, 6.80 g, 22 mmol) in dioxane (20 mL) and NaOH (2N aq) (120 mL, 240 mmol) was heated in an oil bath set to 95° C. The resulting clear, pale yellow solution was left to stir over the weekend. The solution was cooled in an ice bath and neutralized to approximately pH 7 with 6 N HCl resulting in the formation of a precipitate. The solids were collected and left to air dry overnight. The white solid was slurried in hot ethanol (~100 mL) and re-collected by filtration and the solid was air-dried then placed under high vacuum. (5.8 g, 20.41 mmol). HPLC retention time=0.64 min (Condition G); LC/MS $M^{+1}$=284/286. $^1$H NMR (500 MHz, methanol-d$_4$) δ 7.52-7.38 (m, 2H), 7.31-7.17 (m, 2H), 3.55-3.40 (m, 1H), 2.68 (dd, J=13.3, 6.7 Hz, 1H from single diastereomer), 2.58-2.39 (m, 1H), 2.26-2.15 (m, 1H), 2.10-1.98 (m, 1H), 1.98-1.81 (m, 1H), 1.70 (dd, J=13.2, 11.8 Hz, 1H from single diastereomer).

Intermediate 2D: (3R)-Methyl 1-amino-3-(4-bromophenyl)cyclopentanecarboxylate

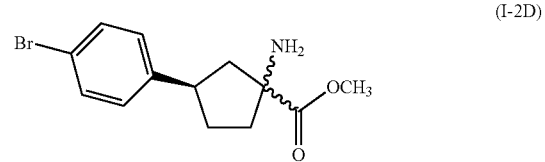

(I-2D)

In a 500 mL round bottom flask containing a stir bar, (3R)-1-amino-3-(4-bromophenyl)cyclopentanecarboxylic acid (I-2C, 5.4 g, 19.00 mmol) was suspended in methanol (100 mL) to afford a white slurry. A dropping funnel was charged with thionyl chloride (13.87 mL, 190 mmol) and the reagent was added dropwise at a rate to keep the mixture from reaching reflux temperature. After the addition was complete, the pale yellow, milky solution was placed in an oil bath set to 70° C. and an air-cooled reflux condenser was attached. The solution was heated for several hours and then allowed to cool to room temperature overnight. The solvent was evaporated under vacuum. The residue was dissolved in ethyl acetate, washed with 1N NaOH (aq), washed with water, then dried over MgSO$_4$ before being filtered and concentrated. The resulting yellow solid was slurried in warm ethyl acetate, with sonication and then filtered. The solid was air-dried and placed under vacuum and the filtrate was evaporated to afford Solid 1: white solid, 4.28 g LCMS shows >98% AP. The filtrate was evaporated to afford a yellow solid (1.89 g). The solid from the filtrate was slurried in a minimal amount of hot ethyl acetate, with sonication, then cooled (ice bath) and filtered cold. The solid was air-dried and placed under vacuum to afford Solid 2: 1.44 g white solid. Combined solids (5.7 g).

Intermediate 2: (1R,3R)-Methyl 1-amino-3-(4-bromophenyl)cyclopentanecarboxylate (I-2)

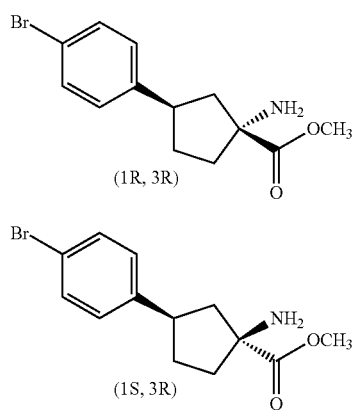

Peak 1 (SFC)

(1R, 3R)

Peak 2 (SFC)

(1S, 3R)

The combined solids of (3R)-methyl 1-amino-3-(4-bromophenyl)cyclopentanecarboxylate (I-2D, 4 g) were separated using Chiral SFC separation of the diastereomers. The absolute stereochemical assignment of Intermediate 2 and its diastereomer has been previously described (Wallace, G. A. et al., *J. Organic Chem.*, 74:4886-4889 (2009)). Experimental Details: Instrument: Preparative: Thar SFC350; Analytical: Thar analytical MDS. Preparative Conditions: Column: CHIRALPAK® AD-H 25×5 cm, 5 μm; Column Temperature: 35° C.; Flow rate: 300 ml/min; Mobile Phase: $CO_2$/(MeOH with 0.1% DEA)=82/18; Detector Wavelength: 230 nm; Injection Vol.: 0.4-0.5 ml; Sample Preparation: 4 g in 120 ml MeOH (Conc. 33 mg/ml). Analytical Conditions: Column: CHIRALPAK® AD-H 25×0.46 cm, 5 μm; Column Temperature: 35° C.; Flow rate: 3 ml/min; Mobile Phase: $CO_2$/(MeOH with 0.1% DEA)=80/20; Detector Wavelength: 222 nm; Injection Vol.: 5 mL.

Intermediate 2 (Peak 1): 1.56 g (99.3% optical purity at 222 nm) Ret. Time=7.18 min on analytical chiral SFC. $^1$H NMR (500 MHz, methanol-$d_4$) δ 7.45-7.39 (m, 2H), 7.23-7.17 (m, 2H), 3.78 (s, 3H), 3.40-3.48 (m, 1H), 2.40 (ddd, J=13.0, 8.9, 3.6 Hz, 1H), 2.28-2.21 (m, 1H), 2.18 (dd, J=13.0, 11.7 Hz, 1H), 2.04 (dd, J=13.0, 7.2 Hz, 1H), 1.88-1.79 (m, 1H), 1.79-1.70 (m, 1H).

Peak 2: 1.8 g (97.2% optical purity at 222 nm). Ret. Time=7.71 min on analytical chiral SFC. $^1$H NMR (500 MHz, methanol-$d_4$) δ 7.45-7.38 (m, 2H), 7.26-7.20 (m, 2H), 3.78 (s, 3H), 3.28-3.20 (m, 1H), 2.66-2.57 (m, 1H), 2.25 (ddd, J=12.8, 11.0, 7.2 Hz, 1H), 2.10 (dt, J=12.2, 6.8 Hz, 1H), 2.03-1.93 (m, 1H), 1.84 (ddd, J=13.0, 7.8, 2.2 Hz, 1H), 1.65 (dd, J=13.3, 11.1 Hz, 1H).

Intermediate 3

(5R,7S)-7-(4-Bromophenyl)-3-oxa-1-azaspiro[4.4]nonan-2-one (I-3)

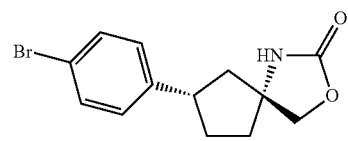

Intermediate 3A: ((1R,3S)-1-Amino-3-(4-bromophenyl)cyclopentyl)methanol (I-3A)

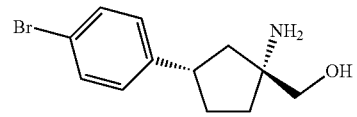

To a mixture of (1R,3S)-methyl 1-amino-3-(4-bromophenyl)cyclopentanecarboxylate, HCl (I-1 HCl, 15 g, 44.8 mmol) in MeOH (100 mL) at 0° C. was added sodium borohydride (4 g, 106 mmol) portionwise. The reaction mixture was warmed to room temperature and sodium borohydride was added portionwise until the reaction was determined to be complete by HPLC analysis. Water was added to quench the reaction. The reaction mixture was diluted with ethyl acetate and washed with saturated NaCl. The aqueous layer was back extracted several times. The combined organic layers were dried with $MgSO_4$, filtered and concentrated. The product (11 g) was recovered after concentration. HPLC retention time=0.65 min (Condition G); LC/MS $M^{+1}$=272: $^1$H NMR (400 MHz, DMSO-$d_6$) δ 7.51-7.40 (m, 2H), 7.27 (d, J=8.4 Hz, 2H), 3.32-3.20 (m, 2H), 3.09-2.92 (m, 1H), 2.11 (dd, J=12.9, 8.7 Hz, 1H), 1.98-1.87 (m, 1H), 1.80 (qd, J=11.1, 7.9 Hz, 1H), 1.69-1.58 (m, 1H), 1.48 (ddd, J=12.4, 7.9, 2.2 Hz, 1H), 1.32 (dd, J=12.8, 10.1 Hz, 1H).

Intermediate 3: (5R,7S)-7-(4-Bromophenyl)-3-oxa-1-azaspiro[4.4]nonan-2-one

To a mixture of ((1R,3S)-1-amino-3-(4-bromophenyl)cyclopentyl)methanol (11 g, 40.7 mmol) and pyridine (I-3A, 3.29 mL, 40.7 mmol) in dioxane (300 mL) was added 1,1'-carbonyldiimidazole (19.81 g, 122 mmol). The reaction mixture was stirred for 4 hours. The reaction mixture was diluted with ethyl acetate and washed with 1M HCl, brine and saturated $NaHCO_3$. The mixture was back extracted several times. The organic layer was dried with $MgSO_4$, filtered and concentrated to afford 10.5 g of desired product as an off-white solid. HPLC retention time=0.87 min (Condition G). LC/MS $M^{+1}$=297.9; $^1$H NMR (400 MHz, chloroform-d) δ 7.45 (d, J=8.6 Hz, 2H), 7.12 (d, J=8.4 Hz, 2H), 6.42 (br. s., 1H), 4.41-4.21 (m, 2H), 3.17-2.91 (m, 1H), 2.34 (dd, J=13.3, 7.4 Hz, 1H), 2.23-2.11 (m, 2H), 2.01-1.90 (m, 2H), 1.88-1.74 (m, 1H).

Intermediate 4

(5R,7R)-7-(4-Bromophenyl)-3-oxa-1-azaspiro[4.4]nonan-2-one

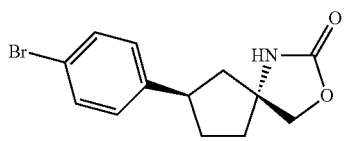
(I-4)

Intermediate 4A: ((1R,3R)-1-Amino-3-(4-bromophenyl)cyclopentyl)methanol

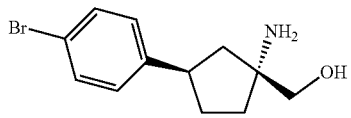
(I-4A)

(1R,3R)-Methyl 1-amino-3-(4-bromophenyl)cyclopentanecarboxylate (I-2, 3.88 g, 13.01 mmol) was dissolved in MeOH (65.1 ml) and sodium borohydride (1.477 g, 39.0 mmol) was added portionwise. Additional sodium borohydride was added (0.5 equiv every 1 h) portionwise until the reaction was determined to be complete by HPLC analysis. The reaction was found to be complete after 2 hours. The reaction mixture was quenched with water and diluted with ethyl acetate. The aqueous layer was back extracted three times with EtOAc. The organic layers were combined, washed with saturated NaCl, dried over MgSO$_4$, filtered and concentrated to afford ((1R,3R)-1-amino-3-(4-bromophenyl)cyclopentyl)methanol (3.19 g, 11.81 mmol). HPLC ret time=0.68 min; LC/MS M$^{+1}$=272: $^1$H NMR (400 MHz, CDCl$_3$) δ 7.42 (d, J=8.4 Hz, 2H), 7.13 (d, J=8.4 Hz, 2H), 3.49 (s, 2H), 3.32-3.41 (m, 1H), 2.19-2.25 (m, 1H), 1.98-2.07 (m, 1H), 1.90-1.95 (m, 1H), 1.66-1.74 (m, 2H), 1.52-1.60 (m, 1H).

Intermediate 4: (5R,7R)-7-(4-Bromophenyl)-3-oxa-1-azaspiro[4.4]nonan-2-one ((1R,3R)-1-Amino-3-(4-bromophenyl)cyclopentyl)methanol (I-4A, 3.19 g, 11.81 mmol) was dissolved in THF (59.0 ml). Pyridine (0.955 ml, 11.81 mmol) and 1,1'-carbonyldiimidazole (5.74 g, 35.4 mmol) were added portionwise. The reaction mixture was stirred for 4 h and was followed by LCMS. After completion, the mixture was diluted with EtOAc and washed with 1M HCl. The aqueous layer was back extracted twice with EtOAc. The organic layers were combined, washed with saturated NaCl, dried over MgSO$_4$, filtered and concentrated to afford (5R,7R)-7-(4-bromophenyl)-3-oxa-1-azaspiro[4.4]nonan-2-one (2.5 g, 8.44 mmol) after flash chromatography (24 g silica gel column; eluent: hexane 2 CV followed by a gradient to 100% EtOAc over 15 CV). HPLC ret time=0.91 min; LC/MS M$^{+1}$=298. $^1$H NMR (400 MHz, CDCl$_3$) δ 7.46 (d, J=8.5 Hz, 2H), 7.09 (d, J=8.5 Hz, 2H), 5.72-5.81 (m, 1H), 4.35 (dd, J=13 Hz, 8 Hz, 2H), 3.19-3.24 (m, 1H), 2.38-2.44 (m, 1H), 2.15-2.26 (m, 1H), 2.11-2.14 (m, 1H), 1.99-2.05 (m, 1H), 1.79-1.85 (m, 1H), 1.65-1.72 (m, 1H).

Intermediate 5

(5R,7S)-7-(6-oxo-5,6,7,8-tetrahydronaphthalen-2-yl)-3-oxa-1-azaspiro[4.4]nonan-2-one

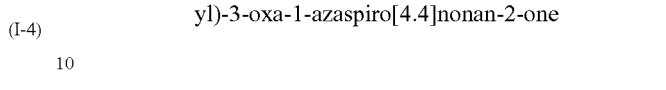
(I-5)

Intermediate 5A: tert-Butyl 2-(4-((5R,7S)-2-oxo-3-oxa-1-azaspiro[4.4]nonan-7-yl)phenyl)acetate

(I-5A)

To a mixture of (5R,7S)-7-(4-bromophenyl)-3-oxa-1-azaspiro[4.4]nonan-2-one (I-3, 1 g, 3.38 mmol) in dioxane (10 mL) at room temperature was added lithium bis(trimethylsilyl)amide (3.71 mL, 3.71 mmol). The mixture was stirred for 30 minutes, then 1,2,3,4,5-pentaphenyl-1'-(di-t-butylphosphino)ferrocene (0.121 g, 0.169 mmol), Pd$_2$(dba)$_3$ (0.155 g, 0.169 mmol) and (2-(tert-butoxy)-2-oxoethyl)zinc(II) chloride (8.10 mL, 4.05 mmol) were added. The reaction mixture was heated at 80° C. for 2 hours, then cooled to room temperature, diluted with ethyl acetate and washed with 1M HCl. The organic layer was dried with MgSO$_4$, filtered and concentrated. The crude material was purified on a silica gel cartridge (40 g) using an EtOAc/hexane gradient (0-100% EtOAc over 20 minutes) to afford 950 mg of tert-butyl 2-(4-((5R,7S)-2-oxo-3-oxa-1-azaspiro[4.4]nonan-7-yl)phenyl)acetate. HPLC retention time=0.93 min (Condition G); LC/MS M$^{+1}$=332.

Intermediate 5B: 2-(4-((5R,7S)-2-oxo-3-oxa-1-azaspiro[4.4]nonan-7-yl)phenyl)acetic acid

(I-5B)

To a mixture of tert-butyl 2-(4-((5R,7S)-2-oxo-3-oxa-1-azaspiro[4.4]nonan-7-yl)phenyl)acetate (I-5A, 1 g, 3.02 mmol) in DCM (20 mL) was added TFA (10 mL). After 2 h, the solution was concentrated in vacuo and used as such for the subsequent step without further purification. HPLC retention time=0.65 min (Condition G); LC/MS M+1=276.

Intermediate 5: (5R,7S)-7-(6-oxo-5,6,7,8-tetrahydronaphthalen-2-yl)-3-oxa-1-azaspiro[4.4]nonan-2-one To a mixture of 2-(4-((5R,7S)-2-oxo-3-oxa-1-azaspiro[4.4]nonan-7-yl)phenyl)acetic acid (I-5B, 800 mg, 2.91 mmol) in DCM (20 mL) was added oxalyl chloride (1 ml, 11.42 mmol) and a few drops of DMF. After one hour, the reaction mixture was concentrated in vacuo. The residue was re-dissolved in DCM (20 mL) in a glass pressure vessel. Granular aluminum chloride (1550 mg, 11.62 mmol) was added and the reaction mixture was cooled to −78° C. Ethylene was bubbled through the solution for 5 minutes and then the reaction vessel was sealed. The reaction mixture was allowed to slowly warm to room temperature and stirred for 4 hours. The mixture was poured onto ice, diluted with dichloromethane and washed with 1M HCl. The organic layer was dried with MgSO₄, filtered and concentrated. The crude material was purified on a silica gel cartridge (80 g) using a MeOH/DCM gradient (0-10% MeOH over 13CV). The product containing fractions were collected and dried in vacuo to afford 770 mg of (5R,7S)-7-(6-oxo-5,6,7,8-tetrahydronaphthalen-2-yl)-3-oxa-1-azaspiro[4.4]nonan-2-one. HPLC retention time=0.74 min (Condition G); LC/MS M+1=286: ¹H NMR (400 MHz, chloroform-d) δ 7.20-7.00 (m, 3H), 5.49 (br. s., 1H), 4.45-4.25 (m, 2H), 3.59 (s, 2H), 3.08 (t, J=6.8 Hz, 3H), 2.58 (t, J=6.7 Hz, 2H), 2.38 (dd, J=13.2, 7.3 Hz, 1H), 2.27-2.11 (m, 2H), 2.05-1.92 (m, 2H), 1.92-1.74 (m, 1H).

Intermediate 6

6-((5R,7S)-2-oxo-3-oxa-1-azaspiro[4.4]nonan-7-yl)-3,4-dihydronaphthalen-2-yl trifluoromethanesulfonate

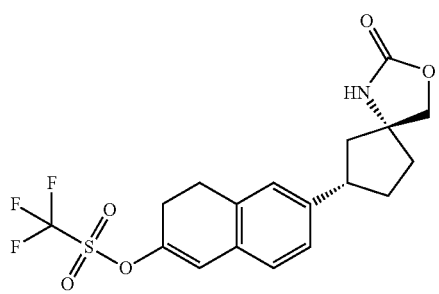

(I-6)

To a mixture of (5R,7S)-7-(6-oxo-5,6,7,8-tetrahydronaphthalen-2-yl)-3-oxa-1-azaspiro[4.4]nonan-2-one (I-5, 340 mg, 1.192 mmol) and DMPU (0.431 mL, 3.57 mmol) in THF (10 mL) at −78° C. was added LDA (1.456 mL, 2.62 mmol). The reaction mixture was stirred for 30 minutes then 1,1,1-trifluoro-N-phenyl-N-(trifluoromethyl)sulfonyl methanesulfonamide (639 mg, 1.787 mmol) in THF (10 mL) was added. The reaction mixture was warmed to 0° C. After 1 hour, the reaction was quenched with water. The reaction mixture was diluted with ethyl acetate and washed with saturated aqueous NaCl. The organic layer was dried with MgSO₄, filtered and concentrated. The crude material was purified on a silica gel cartridge (40 g) using an EtOAc/hexane gradient (0-100% EtOAc over 20 minutes) to afford 400 mg of 6-((5R,7S)-2-oxo-3-oxa-1-azaspiro[4.4]nonan-7-yl)-3,4-dihydronaphthalen-2-yl trifluoromethanesulfonate.

HPLC retention time=1.01 min (Condition G); LC/MS M+1=418. ¹H NMR (400 MHz, chloroform-d) δ 7.17-6.95 (m, 3H), 6.74 (s, 1H), 6.48 (s, 1H), 4.48-4.20 (m, 2H), 3.17-2.95 (m, 3H), 2.81-2.60 (m, 2H), 2.33 (dd, J=13.3, 7.2 Hz, 1H), 2.24-2.08 (m, 2H), 2.05-1.74 (m, 3H).

Intermediate 7

(5R,7R)-7-(6-oxo-5,6,7,8-tetrahydronaphthalen-2-yl)-3-oxa-1-azaspiro[4.4]nonan-2-one

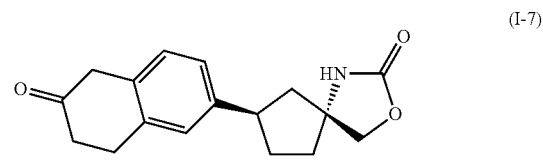 [SMILES: O=C1CCc2cc([C@@H]3CC[C@]4(COC(=O)N4)C3)ccc2C1]

(I-7)

Intermediate 7A: tert-Butyl 2-(4-((5R,7R)-2-oxo-3-oxa-1-azaspiro[4.4]nonan-7-yl)phenyl)acetate

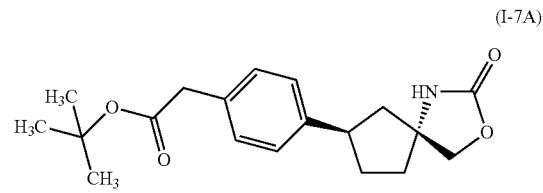 [SMILES: CC(C)(C)OC(=O)Cc1ccc([C@@H]2CC[C@]3(COC(=O)N3)C2)cc1]

(I-7A)

To a solution of (5R,7R)-7-(4-bromophenyl)-3-oxa-1-azaspiro[4.4]nonan-2-one (Int. 4, 2.1 g, 7.09 mmol) in THF (25.3 ml) at room temperature was added LiHMDS (7.80 ml, 7.80 mmol). The solution was stirred for 15 min. Next, Pd₂(dba)₃ (0.195 g, 0.213 mmol), 1,2,3,4,5-pentaphenyl-1'-(di-t-butylphosphino)ferrocene (0.151 g, 0.213 mmol), and (2-(tert-butoxy)-2-oxoethyl)zinc(II) bromide, tetrahydrofuran (7.07 g, 21.27 mmol) were sequentially added. The slurry was stirred at 24° C. for 2 h. LCMS analysis showed complete consumption of the starting material. The reaction mixture was diluted with ethyl acetate and washed with 1M HCl. The organic layer was dried over MgSO₄, filtered and concentrated. The crude material was purified on a silica gel cartridge (40 g) using hexane:acetone 100:0 to 0:100 over 25 CV. tert-Butyl 2-(4-((5R,7R)-2-oxo-3-oxa-1-azaspiro[4.4] nonan-7-yl)phenyl)acetate (2.35 g, 7.09 mmol) was isolated. HPLC retention time=0.95 min (Condition I): LC/MS M+1=332; ¹H NMR (400 MHz, chloroform-d) δ 7.27-7.21 (m, 2H), 7.21-7.15 (m, 2H), 5.11 (br. s., 1H), 4.40-4.26 (m, 2H), 3.53 (s, 2H), 3.22-3.01 (m, 1H), 2.36 (dd, J=13.2, 7.3 Hz, 1H), 2.25-2.10 (m, 2H), 2.04-1.92 (m, 2H), 1.91-1.76 (m, 1H), 1.47 (s, 9H).

Intermediate 7: (5R,7R)-7-(6-oxo-5,6,7,8-tetrahydronaphthalen-2-yl)-3-oxa-1-azaspiro[4.4]nonan-2-one The brown liquid tert-butyl 2-(4-((5R,7R)-2-oxo-3-oxa-1-azaspiro[4.4]nonan-7-yl)phenyl)acetate (I-7A, 2.35 g, 7.09 mmol) was dissolved in DCM (60 mL) followed by the addition of trifluoroacetic acid (20 mL, 260 mmol). The reaction mixture was stirred at room temperature for 1 h at which time the solvent was removed under reduced pressure. The resulting material was diluted in DCM (60 mL), purified by acid/ base extraction and placed under vacuum for 1 h. The resulting brown gum 2-(4-((5R,7R)-2-oxo-3-oxa-1-azaspiro[4.4]nonan-7-yl)phenyl)acetic acid (1.952 g, 7.09 mmol) was dissolved in DCM (60 mL) followed by the addition of oxalyl chloride (1.862 mL, 21.27 mmol), and DMF (0.027 mL, 0.355 mmol). The resulting solution was stirred until the evolution of gas ceased (about 30 min) at room temperature. LCMS of an aliquot quenched with MeOH showed complete consumption of the acid (RT=0.65 min, Condition I) and appearance of the presumed methyl ester due to methanol quench (RT=0.77 min, Condition I) as the only product. The solvent was removed under reduced pressure and the product was placed under vacuum. The brown gum was transfer to a sealed tube with DCM (60 mL) (does not completely dissolve, a brown suspension is obtained). The reaction mixture was cooled to −78° C. followed by the addition of granular aluminum chloride (2.84 g, 21.27 mmol). Ethylene was bubbled through the solution for 7 min and the tube was sealed. A precipitate formed and the reaction mixture was stirred at −78° C. for 15 min and then allowed to reach room temperature. The reaction mixture was stirred for 2 h at room temperature and then depressurized. LCMS analysis showed disappearance of starting material and appearance of the tetralone product. The reaction mixture was poured over ice, diluted with DCM and stirred until the ice melted. The organic layer was washed with brine, dried and concentrated under reduced pressure. Purification on silica gel afforded (5R,7R)-7-(6-oxo-5,6,7,8-tetrahydronaphthalen-2-yl)-3-oxa-1-azaspiro[4.4]nonan-2-one (1.05 g, 3.68 mmol). HPLC retention time=0.74 min (Condition I); LC/MS M$^{+1}$=286; $^1$H NMR (400 MHz, chloroform-d) δ 7.23-7.11 (m, 3H), 5.68 (br. s., 1H), 4.45-4.30 (m, 2H), 3.59 (s, 2H), 3.31-3.18 (m, 1H), 3.08 (t, J=6.8 Hz, 2H), 2.58 (t, J=6.7 Hz, 2H), 2.42-2.39 (m, 1H), 2.32-2.15 (m, 2H), 2.09-1.99 (m, 1H), 1.91-1.83 (m, 1H), 1.82-1.72 (m, 1H).

Intermediate 8

(1-Amino-3-((R)-6-hexyl-5,6,7,8-tetrahydronaphthalen-2-yl)cyclopentyl)methanol

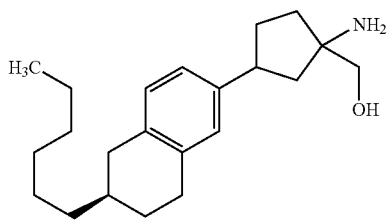

(8)

Intermediate 8A:
6-Iodo-3,4-dihydronaphthalen-1(2H)-one

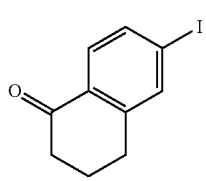

(I-8A)

To a stirred clear solution of 6-amino-3,4-dihydronaphthalen-1(2H)-one (15 g, 93 mmol) in acetic acid (150 mL) and water (150 mL) was added sulfuric acid (5.5 mL, 101 mmol) dropwise at 0° C. A solution of sodium nitrite (12.90 g, 187 mmol) in water (100 mL) was then added dropwise over 40 min at the same temperature. The mixture was stirred at 0° C. for 10 min before being added to a stirred solution of sodium iodide (55.8 g, 372 mmol) in water (600 mL) slowly over 2 h at 0° C. The resulting brown suspension was stirred at 0° C. for 30 min and at room temperature for 1 h. The mixture was extracted with ethyl acetate (400 mL, 2×100 mL). The combined ethyl acetate extracts were washed with water (60 mL), saturated aqueous $Na_2S_2O_3$ solution until the brown color disappeared, and saturated aqueous $K_3PO_4$ (60 mL) solution, dried over anhydrous sodium sulfate, and concentrated under reduced pressure. Flash chromatography purification (330 g silica gel column, gradient elution from 5 to 15% ethyl acetate in hexanes) afforded 6-iodo-3,4-dihydronaphthalen-1(2H)-one (17.3 g, 63.6 mmol) as a solid. LC/MS M$^{+1}$=273.

Intermediate 8B: (S)—N-(6-Iodo-3,4-dihydronaphthalen-1(2H)-ylidene)-2-(methoxymethyl) pyrrolidin-1-amine

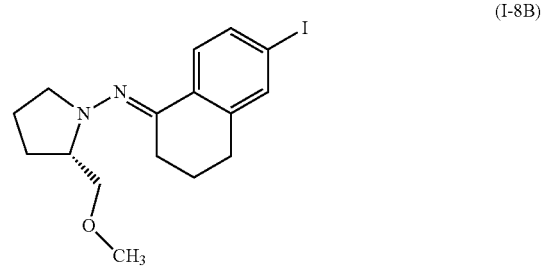 [SMILES: COC[C@@H]1CCCN1/N=C1\CCCc2cc(I)ccc21]

(I-8B)

To a stirred mixture of 6-iodo-3,4-dihydronaphthalen-1(2H)-one (I-8A, 20.90 g, 77 mmol), p-toluenesulfonic acid monohydrate (0.584 g, 3.07 mmol), and cyclohexane (40 mL) was added (S)-2-(methoxymethyl)pyrrolidin-1-amine (10 g, 77 mmol) dropwise at room temperature under nitrogen. The mixture was heated with azeotropic removal of water for 5 h. The reaction mixture was diluted with ethyl acetate (20 mL) and mixed with saturated aqueous sodium bicarbonate solution (15 mL). The aqueous layer was separated and extracted with ethyl acetate (2×30 mL). The combined organic solutions were dried over anhydrous sodium sulfate and concentrated under reduced pressure. Flash chromatography purification (330 g silica gel column, gradient elution from 0% to 20% EtOAc in hexanes) afforded (S)—N-(6-iodo-3,4-dihydronaphthalen-1(2H)-ylidene)-2-(methoxymethyl)pyrrolidin-1-amine (29.1 g, 76 mmol) as a yellow liquid. LC/MS M$^{+1}$=385.

Intermediate 8C: (R)-2-Hexyl-6-iodo-3,4-dihydronaphthalen-1(2H)-one

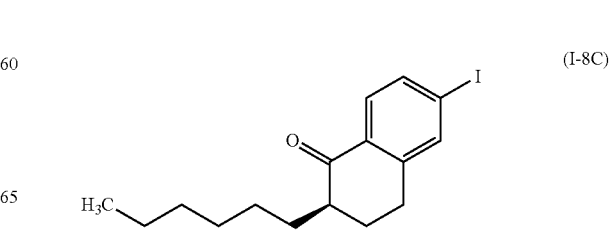

(I-8C)

To a stirred solution of diisopropylamine (19.43 mL, 136 mmol) in anhydrous tetrahydrofuran (250 mL) was added butyl lithium solution (2.5 M in hexanes, 39.4 mL, 98 mmol) dropwise at 0° C. under nitrogen. The resulting solution was stirred at the same temperature for 15 min before a solution of (S)—N-(6-iodo-3,4-dihydronaphthalen-1(2H)-ylidene)-2-(methoxymethyl)pyrrolidin-1-amine (I-8B, 29.1 g, 76 mmol) in anhydrous tetrahydrofuran (100 mL) was added dropwise. The reaction solution was stirred at 0° C. for 2 h. A solution of 1-iodohexane (22.35 mL, 151 mmol) in tetrahydrofuran (50 mL) was added dropwise at −78° C. and the mixture was stirred at the same temperature for 2 h. The temperature was raised to room temperature over 1.5 h. The reaction mixture was quenched with saturated aqueous ammonium chloride solution (50 mL) and water (50 mL). The mixture was extracted with hexanes (200 mL) and ethyl acetate (3×50 mL). The combined extracts were dried over anhydrous sodium sulfate and concentrated under reduced pressure to give an oil. The oil was dissolved in THF (200 mL). A solution of cupric chloride, dihydrate (52 g) in water (220 mL) was added at 0° C. dropwise and the mixture was vigorously stirred at room temperature overnight. Aqueous ammonia solution was added to raise the pH to approximately 9. The mixture was extracted with hexane (100 mL) and diethyl ether (2×100 mL). The combined extracts were dried over anhydrous sodium sulfate and concentrated. Flash chromatography purification (330 g silica gel column, gradient elution from 0 to 15% EtOAc in hexanes) afforded (R)-2-hexyl-6-iodo-3,4-dihydronaphthalen-1(2H)-one (21.6 g, 60.6 mmol) as a white solid containing some of the (S) isomer, which was removed in the subsequent step. LC/MS M$^{+1}$=357.

Intermediate 8D:
(R)-2-Hexyl-6-iodo-1,2,3,4-tetrahydronaphthalene

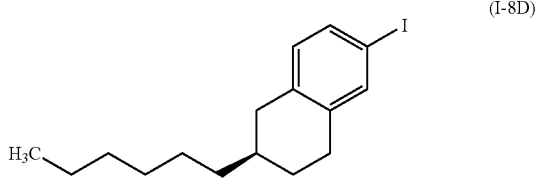 [SMILES: CCCCCC[C@@H]1CCc2cc(I)ccc2C1]

(I-8D)

To a stirred solution of (R)-2-hexyl-6-iodo-3,4-dihydronaphthalen-1(2H)-one (I-8C, 21.6 g, 60.6 mmol) in dichloromethane (10 mL) and 100% EtOH (100 mL) was added sodium borohydride (4.59 g, 121 mmol) portionwise. The mixture was stirred at room temperature for 2 h before being quenched by adding acetone slowly (cooled with water bath). The mixture was concentrated under reduced pressure. The residue was mixed with saturated aqueous ammonium chloride solution (100 mL) and water (50 mL) and extracted with ethyl acetate (100 mL, 2×50 mL). The combined ethyl acetate extracts were dried over anhydrous sodium sulfate and concentrated under reduced pressure to give an oil. The oil was dissolved in triethylsilane (70 mL, 438 mmol). TFA (100 mL, 1298 mmol) was added with vigorous stirring. The mixture was stirred at room temperature under nitrogen for 2.5 h. After water (150 mL) was added, the mixture was extracted with hexanes (100 mL, 2×50 mL). The combined extracts were washed with water (50 mL) and then saturated aqueous sodium bicarbonate solution (50 mL), dried over anhydrous sodium sulfate, and concentrated to give a yellow liquid. Flash chromatography purification (330 g silica gel column, gradient elution from 0 to 12% EtOAc in hexanes) afforded (R)-2-hexyl-6-iodo-1,2,3,4-tetrahydronaphthalene (18.4 g, 53.8 mmol) as a colorless liquid. $^1$H NMR (400 MHz, chloroform-d) δ 7.41 (s, 1H), 7.38 (dd, J=7.9, 1.8 Hz, 1H), 6.79 (d, J=8.1 Hz, 1H), 2.82-2.71 (m, 3H), 2.31 (dd, J=16.5, 10.6 Hz, 1H), 1.93-1.85 (m, 1H), 1.72-1.60 (m, 1H), 1.41-1.24 (m, 11H), 0.92-0.85 (m, 3H). Chiral SFC separation (CHIRALPAK® AS-H 25×3.0 cm, 5 nm, CO$_2$/MeOH=95/5, 180 mL/min, 230 nm) gave (R)-2-hexyl-6-iodo-1,2,3,4-tetrahydronaphthalene (11.8 g, PK2) and its (S)-isomer (1.4 g, PK1) as liquids.

Intermediate 8E: 3-((R)-6-Hexyl-5,6,7,8-tetrahydronaphthalen-2-yl)cyclopentanone

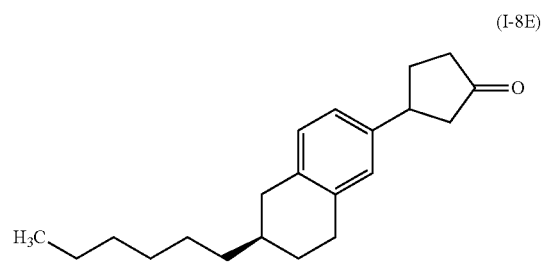 [SMILES: CCCCCC[C@@H]1CCc2cc(C3CCC(=O)C3)ccc2C1]

(I-8E)

Nitrogen gas was bubbled through a mixture of (R)-2-hexyl-6-iodo-1,2,3,4-tetrahydronaphthalene (I-8D, 11.8 g, 34.5 mmol), tetrabutylammonium chloride (9.58 g, 34.5 mmol), potassium acetate (10.15 g, 103 mmol), palladium (II) acetate (0.774 g, 3.45 mmol), and anhydrous DMF (100 mL) for 3 min before cyclopent-2-enol (6.8 g, 81 mmol, prepared according to Larock, R. C. et al., *Tetrahedron*, 50(2): 305-321 (1994)) was added. Nitrogen gas was bubbled through the solution for an additional 2 min. The mixture was stirred at 80° C. under nitrogen for 2.5 h and then concentrated to remove DMF. The residue was mixed with water (150 ml) and extracted with ethyl acetate (4×50 mL). The combined ethyl acetate solutions were washed with water (30 mL), dried over anhydrous sodium sulfate, filtered through a silica gel pad, and concentrated under reduced pressure. Flash chromatography purification (220 g silica gel column, gradient elution from 5 to 50% ethyl acetate in hexanes) afforded 3-((R)-6-hexyl-5,6,7,8-tetrahydronaphthalen-2-yl)cyclopentanone (5.96 g, 19.97 mmol) LC/MS M$^{+1}$=299.

Intermediate 8F: Methyl 1-amino-3-((R)-6-hexyl-5,6,7,8-tetrahydronaphthalen-2-yl)cyclopentanecarboxylate

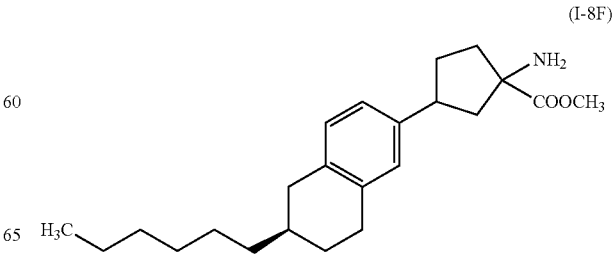

(I-8F)

A mixture of 3-((R)-6-hexyl-5,6,7,8-tetrahydronaphthalen-2-yl)cyclopentanone (I-8E, 5.96 g, 19.97 mmol), ammonium chloride (5.34 g, 100 mmol), sodium cyanide (4.89 g, 100 mmol), 7 M methanol solution of ammonia (28.5 ml, 200 mmol), and dichloromethane (15 mL) was stirred at room temperature for 1 day. Additional 7 M methanol solution of ammonia (15 mL) was added. The mixture was stirred at room temperature for 1 day and then concentrated. The residue was partitioned between ethyl acetate (70 mL) and saturated aqueous sodium bicarbonate solution (100 mL). The aqueous layer was separated and extracted with ethyl acetate (3×50 mL). The combined ethyl acetate solutions were dried over anhydrous sodium sulfate and concentrated under reduced pressure to give 1-amino-3-((R)-6-hexyl-5,6,7,8-tetrahydronaphthalen-2-yl)cyclopentanecarbonitrile as a semi-solid. The semi-solid material was mixed with a mixture of concentrated hydrochloric acid (56 ml, 1843 mmol), water (28 ml, 1554 mmol), acetic acid (35 ml), and dioxane (35 ml). The mixture was stirred at 100° C. under nitrogen for 10 h and then concentrated to give a solid. The solid was dissolved in methanol (20 mL) and mixed with toluene (20 mL). The mixture was concentrated to dryness. This drying procedure was repeated one more time to give a dry solid. The solid was dissolved in anhydrous methanol (300 mL). Thionyl chloride (11.66 mL, 160 mmol) was added dropwise at 0° C. under nitrogen. The reaction mixture was stirred at 70° C. for 7 h before being concentrated. The residue was made basic with saturated aqueous sodium bicarbonate solution (100 mL) and some potassium carbonate solid and extracted with ethyl acetate (100 mL, 3×30 mL). The combined ethyl acetate extracts were dried over anhydrous sodium sulfate and concentrated under reduced pressure. Flash chromatography purification (80 g silica gel column, gradient elution from 20 to 100% ethyl acetate in hexanes) afforded methyl 1-amino-3-((R)-6-hexyl-5,6,7,8-tetrahydronaphthalen-2-yl)cyclopentanecarboxylate (5.7 g, 15.94 mmol) as a liquid. LC/MS $M^{+1}=358$.

Intermediate 8

Methyl 1-amino-3-((R)-6-hexyl-5,6,7,8-tetrahydronaphthalen-2-yl)cyclopentanecarboxylate (I-8F, 5.7 g, 16 mmol) was dissolved in EtOH (60 mL) and methylene chloride (15 mL). Sodium borohydride (2.5 g, 67 mmol) was added. The mixture was stirred at room temperature overnight. Hydrochloric acid (6 N aqueous, 40 mL) was added slowly at 0° C. to make pH approximately 1. After the mixture was stirred at room temperature for 60 min, sodium hydroxide (10 g in 20 mL of water) was added to make pH approximately 12. The mixture was stirred at room temperature for 40 min before being concentrated to remove organic solvents. The aqueous residue was diluted with water (20 mL) and extracted with EtOAc (100 mL, 2×50 mL). The combined ethyl acetate extracts were dried over anhydrous sodium sulfate, decolored by charcoal, filtered through CELITE® pad, and concentrated under reduced pressure to give (1-amino-3-((R)-6-hexyl-5,6,7,8-tetrahydronaphthalen-2-yl)cyclopentyl)methanol (5.0 g, 15 mmol) as a white solid.

Examples 1 and 2 and Compounds 3 and 4

Intermediate 8 was separated into 3 fractions: F1 (Peak 1), F2 (Peak 2 and Peak 3), F3 (Peak 4)) using chiral SFC (Column: CHIRALPAK® AD-H 25×3 cm, 5 µm; Mobile Phase: $CO_2$/(MeOH+0.1% DEA)=88/12; Flow Rate: 200 mL/min; Detector Wavelength: 220 nm; Column Temperature: 35° C.). The second fraction (F2) was separated again using chiral SFC (Column: CHIRALPAK® AS-H 25×3 cm, 5 µm; Mobile Phase: $CO_2$/[MeOH-MeCN (1:1)+0.5% DEA]=88/12; Flow Rate: 180 mL/min; Detector Wavelength: 220 nm; Column Temperature: 35° C.) to give Peak 2 and Peak 3. All four isomers are white solids with LC/MS $M^{+1}=330$.

Example 1 (Peak 2): $^1$H NMR (400 MHz, chloroform-d) δ 7.07-6.95 (m, 3H), 3.54-3.44 (m, 2H), 3.34 (tt, J=11.0, 7.0 Hz, 1H), 2.92-2.74 (m, 3H), 2.39 (dd, J=16.4, 10.7 Hz, 1H), 2.29-2.14 (m, 1H), 2.08-1.84 (m, 3H), 1.76-1.65 (m, 3H), 1.46-1.26 (m, 12H), 0.99-0.85 (m, 3H).

Example 2 (Peak 4): $^1$H NMR (400 MHz, chloroform-d) δ 7.06-6.92 (m, 3H), 3.52-3.37 (m, 2H), 3.09-2.93 (m, 1H), 2.88-2.72 (m, 3H), 2.35 (dd, J=15.8, 10.6 Hz, 1H), 2.26 (dd, J=12.7, 7.8 Hz, 1H), 2.11-2.00 (m, 1H), 1.97-1.84 (m, 2H), 1.78-1.60 (m, 3H), 1.43-1.22 (m, 12H), 0.95-0.83 (m, 3H).

Compound 3 (Peak 1): $^1$H NMR (400 MHz, chloroform-d) δ 7.03-6.92 (m, 3H), 3.46 (s, 2H), 3.39-3.24 (m, 1H), 2.88-2.72 (m, 3H), 2.36 (dd, J=16.3, 10.8 Hz, 1H), 2.27-2.13 (m, 1H), 2.08-1.82 (m, 3H), 1.76-1.63 (m, 3H), 1.43-1.20 (m, 12H), 0.94-0.85 (m, 3H).

Compound 4 (Peak 3): $^1$H NMR (400 MHz, chloroform-d) δ 7.02-6.92 (m, 3H), 3.51-3.37 (m, 2H), 3.08-2.94 (m, 1H), 2.87-2.71 (m, 3H), 2.35 (dd, J=16.2, 11.1 Hz, 1H), 2.25 (dd, J=13.1, 7.8 Hz, 1H), 2.12-1.97 (m, 1H), 1.97-1.83 (m, 2H), 1.81-1.59 (m, 3H), 1.43-1.21 (m, 12H), 0.96-0.74 (m, 3H).

Compounds 5-8 were prepared according to the general synthesis and separation procedures for Intermediate 8, Examples 1-2, and Compounds 3-4 using (S)-enantiomer (PK1) of the iodide Intermediate I-8D. All four isomers (Compounds 5-8) had MW=329.5; LC/MS $M^{+1}=330$; HPLC condition: C.

TABLE 1

| Example No. | Structure | Name | HPLC RT (min.) |
|---|---|---|---|
| 1 | 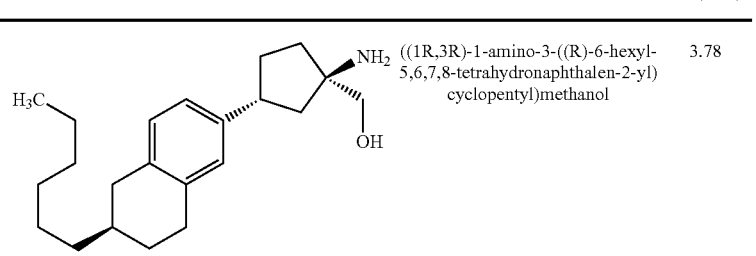 | ((1R,3R)-1-amino-3-((R)-6-hexyl-5,6,7,8-tetrahydronaphthalen-2-yl)cyclopentyl)methanol | 3.78 |

TABLE 1-continued

| Example No. | Structure | Name | HPLC RT (min.) |
|---|---|---|---|
| 2 | 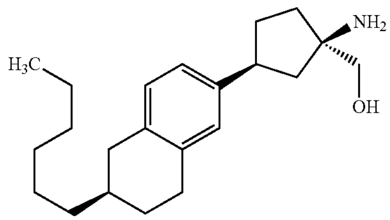 [SMILES: CCCCCC[C@@H]1CCc2cc([C@H]3CC[C@](N)(CO)C3)ccc2C1] | ((1R,3S)-1-amino-3-((R)-6-hexyl-5,6,7,8-tetrahydronaphthalen-2-yl)cyclopentyl)methanol | 3.78 |

TABLE 2

| Compound No. | Structure | Name | HPLC Ret. Time (min.) |
|---|---|---|---|
| 3 | 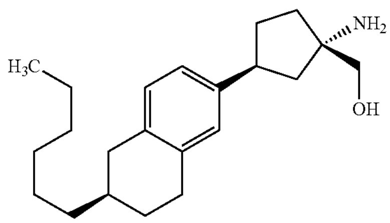 [SMILES: CCCCCC[C@@H]1CCc2cc([C@H]3CC[C@@](N)(CO)C3)ccc2C1] | ((1S,3S)-1-amino-3-((R)-6-hexyl-5,6,7,8-tetrahydronaphthalen-2-yl)cyclopentyl)methanol | 3.78 |
| 4 | 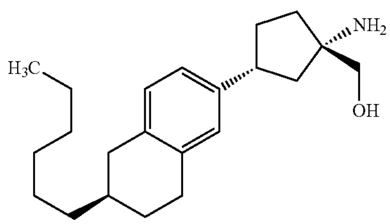 [SMILES: CCCCCC[C@@H]1CCc2cc([C@@H]3CC[C@@](N)(CO)C3)ccc2C1] | ((1S,3R)-1-amino-3-((R)-6-hexyl-5,6,7,8-tetrahydronaphthalen-2-yl)cyclopentyl)methanol | 3.78 |
| 5 | 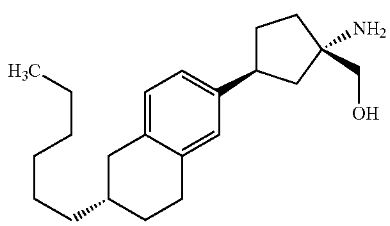 [SMILES: CCCCCC[C@H]1CCc2cc([C@H]3CC[C@@](N)(CO)C3)ccc2C1] | ((1S,3S)-1-amino-3-((S)-6-hexyl-5,6,7,8-tetrahydronaphthalen-2-yl)cyclopentyl)methanol | 3.78 |
| 6 | 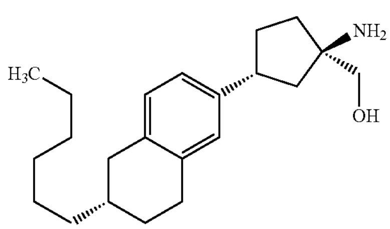 [SMILES: CCCCCC[C@H]1CCc2cc([C@@H]3CC[C@](N)(CO)C3)ccc2C1] | ((1R,3R)-1-amino-3-((S)-6-hexyl-5,6,7,8-tetrahydronaphthalen-2-yl)cyclopentyl)methanol | 3.78 |
| 7 | 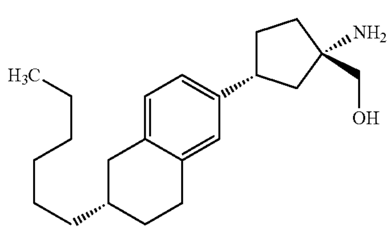 [SMILES: CCCCCC[C@H]1CCc2cc([C@@H]3CC[C@@](N)(CO)C3)ccc2C1] | ((1S,3R)-1-amino-3-((S)-6-hexyl-5,6,7,8-tetrahydronaphthalen-2-yl)cyclopentyl)methanol | 3.77 |

TABLE 2-continued

| Compound No. | Structure | Name | HPLC Ret. Time (min.) |
|---|---|---|---|
| 8 | 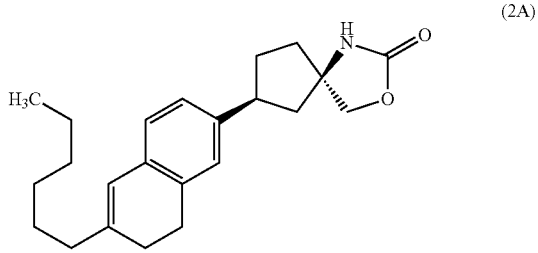 [SMILES: CCCCCCC1=Cc2ccc([C@H]3CC[C@]4(COC(=O)N4)C3)cc2CC1] | ((1R,3S)-1-amino-3-((S)-6-hexyl-5,6,7,8-tetrahydronaphthalen-2-yl)cyclopentyl)methanol | 3.77 |

Alternate Preparation of Example 2

Preparation 2A: (5R,7S)-7-(6-Hexyl-7,8-dihydronaphthalen-2-yl)-3-oxa-1-azaspiro[4.4]nonan-2-one (2A)

To a mixture of 6-((5R,7S)-2-oxo-3-oxa-1-azaspiro[4.4]nonan-7-yl)-3,4-dihydronaphthalen-2-yl trifluoromethanesulfonate (Int. 6, 1 g, 2.396 mmol) and NMP (2.306 mL, 23.96 mmol) in THF (20 mL) at −40° C. was added a solution of lithium bis(trimethylsilyl)amide in THF (2.396 mL, 2.396 mmol). The reaction mixture was stirred for 15 minutes, and then ferric acetylacetonate (0.042 g, 0.120 mmol) and hexylmagnesium bromide in ether (2.396 mL, 4.79 mmol) were added. The reaction mixture was stirred for 30 minutes and quenched with water. The reaction mixture was diluted with ethyl acetate and washed with 1M HCl. The organic layer was dried with MgSO$_4$, filtered and concentrated. The crude material was purified on a silica gel cartridge (40 g) using an EtOAc/hexane gradient (0-100% EtOAc over 12 CV) to afford 662 mg of (5R,7S)-7-(6-hexyl-7,8-dihydronaphthalen-2-yl)-3-oxa-1-azaspiro[4.4]nonan-2-one as a white solid. HPLC retention time=1.28 min (Condition G); LC/MS M$^{+1}$=354: $^1$H NMR (400 MHz, chloroform-d) δ 7.03-6.88 (m, 3H), 6.21 (s, 1H), 5.16 (br. s., 1H), 4.44-4.15 (m, 2H), 3.13-2.96 (m, 1H), 2.80 (t, J=8.0 Hz, 2H), 2.47-2.08 (m, 6H), 2.05-1.93 (m, 2H), 1.90-1.73 (m, 1H), 1.68-1.43 (m, 4H), 1.41-1.22 (m, 5H), 1.01-0.83 (m, 3H).

Preparation 2B: (5R,7S)-7-((R)-6-Hexyl-5,6,7,8-tetrahydronaphthalen-2-yl)-3-oxa-1-azaspiro[4.4]nonan-2-one (2B)

A mixture of (5R,7S)-7-(6-hexyl-7,8-dihydronaphthalen-2-yl)-3-oxa-1-azaspiro[4.4]nonan-2-one (2A, 760 mg, 2.15 mmol) and (−)-2,3-bis[(2R,5R)-2,5-dimethylphospholanyl]-N-[3,5-bis(trifluoromethyl)phenyl]maleicimide(1,5-cyclooctadiene)rhodium(I) tetrafluoroborate (273 mg, 0.43 mmol) in MeOH (27 mL) was hydrogenated at 850 PSI for 1000 minutes using a 100 mL HEL autoclave. The reaction mixture was filtered and concentrated in vacuo. The crude material was purified on a silica gel cartridge (40 g) using an EtOAc/hexane gradient (0-100% EtOAc over 20 minutes) to afford 640 mg of (5R,7S)-7-(6-hexyl-5,6,7,8-tetrahydronaphthalen-2-yl)-3-oxa-1-azaspiro[4.4]nonan-2-one in a 1:2 ratio of the two isomers. The desired major isomer was separated using a CHIRALPAK® AS-H column under SFC conditions (35% MeOH in CO$_2$). Retention time=5.14 min. Recovered 400 mg of (5R,7S)-7-((R)-6-hexyl-5,6,7,8-tetrahydronaphthalen-2-yl)-3-oxa-1-azaspiro[4.4]nonan-2-one. $^1$H NMR (400 MHz, methanol-d$_4$) δ 7.02-6.91 (m, 3H), 4.47-4.20 (m, 2H), 3.02 (tt, J=11.0, 7.2 Hz, 1H), 2.87-2.74 (m, 3H), 2.41-2.24 (m, 2H), 2.17-2.03 (m, 2H), 2.00-1.89 (m, 3H), 1.86-1.74 (m, 1H), 1.73-1.61 (m, 1H), 1.51-1.28 (m, 11H), 0.99-0.88 (m, 3H).

Alternate Preparation of Preparation 2B

A mixture of (5R,7S)-7-(6-hexyl-7,8-dihydronaphthalen-2-yl)-3-oxa-1-azaspiro[4.4]nonan-2-one (2A, 2.1 g, 5.94 mmol) in DCM (10 ml) was added dropwise to a solution of ((1R,2S,3R,5R)-2,6,6-trimethylbicyclo[3.1.1]heptan-3-yl)borane in DCM (30 ml) at −35° C. under nitrogen. (The borane reagent was made as following: To a mixture of S-Alpine-Boramine (8.4 g, 20.18 mmol) in THF (35 ml) was added BF$_3$ ethereate (5.11 ml, 40.4 mmol) at room temperature. The mixture was stirred at room temperature for 1.5 h, filtered under nitrogen, and the cake was washed with cold THF (2×6 ml). The filtrate and washes were combined and concentrated under vacuum. To the residue was added DCM (20 ml) and the solution was concentrated again. The reagent obtained was redissolved in DCM (30 ml) and used directly for the hydroboration step). After stirring at −35° C. to −30° C. for 4 h and at −25° C. to −20° C. for 2 h, MeOH (3.6 mL) was added and the reaction mixture was stirred at −10° C. for 10 min and at 0° C. for 10 min. The mixture was diluted with THF (25 ml), then a solution of NaOH (6N, 9.9 ml, 59.4 mmol) was added dropwise followed by H$_2$O$_2$ (30%, 6.07 ml, 59.4 mmol) and the mixture was stirred at room temperature for 16 h. To the mixture was added DCM (100 ml) and water (50 ml). The whole solution was filtered through a pad of CELITE® and the cake was washed with DCM. The two layers were separated, the aqueous layer was extracted with DCM (50 ml) which was combined with the organic layer. The combined organic layers were washed with water (100 ml) and brine (100 ml), dried over anhydrous $Na_2SO_4$ and concentrated in vacuo. The crude material was purified on a silica gel cartridge (40 g) using an EtOAc/hexane gradient (0-50% EtOAc over 55 minutes) to afford 1.9 g (86%) of (5R,7S)-7-(6-hexyl-5,6,7,8-tetrahydronaphthalen-2-yl)-3-oxa-1-azaspiro[4.4]nonan-2-one in a 8:1 ratio of two isomers. The mixture was carried into the next step without separating the diastereomers.

To (5R,7S)-7-(6-hexyl-5,6,7,8-tetrahydronaphthalen-2-yl)-3-oxa-1-azaspiro[4.4]nonan-2-one (3.2 g, 8.61 mmol) in MeOH (30 ml) was added Pd/C (10%, 1.1 g). A slight vacuum was applied to the reaction flask, followed by back filling with hydrogen from a hydrogen balloon. After stirring at room temperature for 6 h, EtOAc (20 ml) was added to dissolve the precipitate. A slight vacuum was applied to the reaction flask, followed by back filling with hydrogen from a hydrogen balloon and the contents stirred at room temperature for 16 h. The mixture was filtered through a pad of CELITE® and the cake was washed with EtOAc, DCM, MeOH and EtOAc. The combined solvents were concentrated in vacuo to afford the crude mixture (3.06 g) as an 8:1 diastereomeric mixture. The major isomer was separated using a CHIRALPAK® AS-H column under SFC conditions (35% MeOH in $CO_2$). Retention time=4.64 min. Recovered 2.35 g (77%) of (5R,7S)-7-((R)-6-hexyl-5,6,7,8-tetrahydronaphthalen-2-yl)-3-oxa-1-azaspiro[4.4]nonan-2-one.

Example 2

To a mixture of (5R,7S)-7-((R)-6-hexyl-5,6,7,8-tetrahydronaphthalen-2-yl)-3-oxa-1-azaspiro[4.4]nonan-2-one (400 mg, 1.125 mmol) in dioxane (30 mL) was added aqueous NaOH (1N, 20 mL). The reaction mixture was heated at 100° C. for 3 days, cooled to room temperature, diluted with ethyl acetate and washed with water. The organic layer was dried with $MgSO_4$, filtered and concentrated. The crude material was purified on a silica gel cartridge (24 g) using an 20% (2N $NH_3$/MeOH) in DCM/DCM gradient (0-75% of 20% (2N $NH_3$/MeOH) in DCM over 13 CV) to afford 290 mg of ((1R,3S)-1-amino-3-((R)-6-hexyl-5,6,7,8-tetrahydronaphthalen-2-yl)cyclopentyl)methanol. HPLC retention time=10.09 min (Condition H); LC/MS $M^{+1}$=330; $^1H$ NMR (400 MHz, methanol-$d_4$) δ 7.03-6.91 (m, 3H), 3.54-3.41 (m, 2H), 3.01 (tt, J=11.1, 7.2 Hz, 1H), 2.87-2.69 (m, 3H), 2.34 (dd, J=16.2, 10.5 Hz, 1H), 2.20 (dd, J=13.0, 7.5 Hz, 1H), 2.07-1.84 (m, 3H), 1.83-1.60 (m, 3H), 1.60-1.48 (m, 1H), 1.47-1.25 (m, 1H), 1.00-0.88 (m, 3H).

Example 2

Free Base, Form N-1

Example 2, free base, Form N-1 was obtained by preparing a stock solution containing 385 mg of Example 2 dissolved in a mixture of 18 ml THF and 1.25 ml $H_2O$ (20 mg/ml). Next, 52 μl of the stock solution was evaporated to dryness. To the dried material was added 52 μl of a 50:50 ratio ethanol:heptane solution. The resulting solution was evaporated to yield plates of crystalline material.

Example 2

Mono-HCl Salt, Monohydrate, Form H-1

The monohydrate, mono-HCl salt of Example 2, Form H-1 was obtained by preparing a 50:50 aqueous methanol (200 μl) solution containing 3.2 mg of Example 2. Next, 400 μl of a 0.025M aqueous HCl solution was added dropwise with stirring. The resulting solution was evaporated to yield plates of crystalline material.

Example 2

Mono-HCl Salt, Monohydrate, Form H-2

The monohydrate, mono-HCl salt of Example 2, Form H-2 was obtained by preparing a 50:50 aqueous THF (200 μl) solution containing 3.2 mg of Example 2. Next, 400 μl of a 0.025M aqueous HCl solution was added dropwise with stirring. The solution was then evaporated to yield plates of the monohydrate H-2 form of the mono-HCl salt of Example 2.

Example 2

Mono-HCl Salt, Form N-3

The mono-HCl salt of Example 2, Form N-3 was obtained by preparing a 200 μl solution of isopropyl alcohol containing 3.2 mg of Example 2. Next, a 400 μl of a 0.025 M alcoholic HCl solution was added dropwise with stirring. The solution was evaporated to yield plates of the N-3 form of the mono-HCl salt of Example 2.

Example 2

Mono-HCl Salt, Form N-4

The mono-HCl salt of Example 2, Form N-3 was obtained by preparing a 200 μl of a 50:50 methanol/THF solution containing 3.2 mg of Example 2. Next, 400 μl of a 0.025 M alcoholic HCl solution was added dropwise with stirring. The resulting solution was evaporated to yield plates of the N-4 form of the mono-HCl salt of Example 2.

Example 2

Monohydrate, Hemi-L-Malic Acid Salt, Form H-1

The monohydrate, hemi-L-malic acid salt, Form H-1 was obtained by preparing a 200 μl, 150:50 aqueous THF solution containing 3.2 mg of Example 2. Next, 240 μl of a 0.042 M alcoholic L-malic acid solution was added dropwise with stirring. The resulting solution was evaporated to yield plates of the H-1 form of the hemi-L-malic acid salt of Example 2.

Example 2

Monohydrate, Hemi-Malonic Acid Salt, Form H-1

The monohydrate, hemi-malonic acid salt, Form H-1 was obtained by preparing a 200 μl, 150:50 aqueous THF solution containing 3.2 mg of Example 2. Next, 193 μl of a 0.052 M alcoholic malonic acid solution was added dropwise with stirring. The resulting solution was evaporated to yield plates of the H-1 form of the hemi-malonic acid salt of Example 2.

Example 2

1/3-Hydrate, Phosphoric Acid Salt, Form H.33-1

The 1/3-hydrate, phosphoric acid salt, Form H.33-1 was obtained by preparing a 200 μl 50:50 aqueous methanol solution containing 3.2 mg of Example 2. Next, 136 μl of a 0.073 M alcoholic phosphoric acid solution was added dropwise with stirring. The resulting solution was evaporated to yield plates of the H.33-1 form of the phosphoric acid salt of Example 2.

Example 2

R-(+)-Mandelic Acid Salt, Form N-1

The R-(+)-mandelic acid salt, Form N-1 was prepared by adding Example 2 and an equimolar amount of R-(+)-mandelic acid to a mixture of methanol and acetonitrile. The solution was evaporated to yield plates of the N-1 form of the mono-R-(+)-mandelic acid salt of Example 2.

Example 9

((1R,3R)-1-Amino-3-((R)-6-hexyl-5,6,7,8-tetrahydronaphthalen-2-yl)cyclopentyl)methyl dihydrogen phosphate

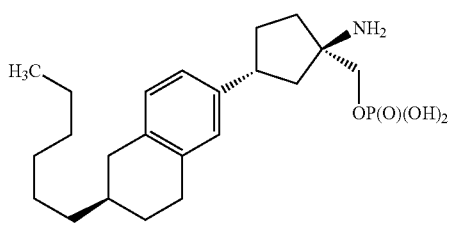

(9)

To a stirred solution of ((1R,3R)-1-amino-3-((R)-6-hexyl-5,6,7,8-tetrahydronaphthalen-2-yl)cyclopentyl)methanol (Example 1, 10 mg, 0.030 mmol) in anhydrous acetonitrile (1 mL) at 0° C. was added pyrophosphoryl chloride (0.042 mL, 0.303 mmol). The clear solution obtained was stirred at the same temperature for 5 min and at RT overnight. After water (0.4 mL) was added, the mixture was stirred at RT for 1 h. Purification using reverse phase HPLC (Luna Axia 5μ c18 30×100 mm, 10 min. gradient from 40% to 100% of Solvent B, Solvent A: 0.1% TFA in water, Solvent B: 0.1% TFA in MeCN), concentration and lyophilization gave ((1R,3R)-1-amino-3-((R)-6-hexyl-5,6,7,8-tetrahydronaphthalen-2-yl)cyclopentyl)methyl dihydrogen phosphate (2 mg, 4.15 μmol, 13.68% yield) as a white solid. HPLC retention time=3.94 min (Condition C); LC/MS $M^{+1}$=410; $^1$H NMR (500 MHz, methanol-$d_4$+KOH) δ 6.97-6.87 (m, 3H), 3.77-3.71 (m, 1H), 3.71-3.66 (m, 1H), 2.83-2.70 (m, 3H), 2.32 (dd, J=16.2, 10.7 Hz, 1H), 2.14-1.98 (m, 2H), 1.96-1.83 (m, 2H), 1.74-1.60 (m, 3H), 1.59-1.49 (m, 1H), 1.45-1.26 (m, 11H), 0.94-0.87 (m, 3H), one proton under methanol solvent peak (~3.3 ppm).

Example 10

((1R,3S)-1-Amino-3-((R)-6-hexyl-5,6,7,8-tetrahydronaphthalen-2-yl)cyclopentyl)methyl dihydrogen phosphate

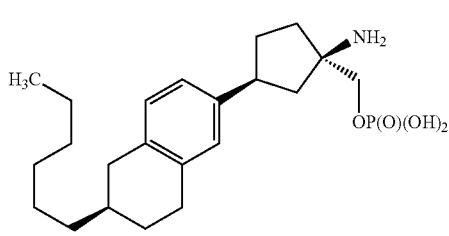

(10)

A mixture of phosphorus pentoxide (150 mg, 0.528 mmol) and 85% phosphoric acid (0.15 mL, 10.01 μmol) was stirred at 100° C. under nitrogen for 1 h before ((1R,3S)-1-amino-3-((R)-6-hexyl-5,6,7,8-tetrahydronaphthalen-2-yl)cyclopentyl)methanol (Example 1, 6 mg, 0.018 mmol) was added. The solution was stirred at the same temperature for 3 h. Water (0.5 mL) was added at room temperature. The mixture was stirred at room temperature for 1 h. Purification using reverse phase HPLC (PHENOMENEX® Luna Axia 5μ c18 30×100 mm, 10 minute run, Solvent A: 10% MeOH: 90% H$_2$O: 0.1% TFA, Solvent B: 90% MeOH, 10% H$_2$O, 0.1% TFA), concentration, and lyophilization gave ((1R,3S)-1-amino-3-((R)-6-hexyl-5,6,7,8-tetrahydronaphthalen-2-yl)cyclopentyl)methyl dihydrogen phosphate (4 mg, 9.38 μmol) as a white solid. LC/MS $M^{+1}$=410. HPLC retention time=3.96 min (Condition C). $^1$H NMR (400 MHz, methanol-$d_4$+CDCl$_3$) δ 7.10-6.83 (m, 3H), 4.06-3.77 (m, 2H), 3.20-3.06 (m, 1H), 2.85-2.74 (m, 2H), 2.48 (dd, J=12.9, 6.9 Hz, 1H), 2.40-2.28 (m, 1H), 2.19-2.08 (m, 1H), 2.05-1.90 (m, 4H), 1.80-1.62 (m, 2H), 1.48-1.22 (m, 12H), 0.95-0.86 (m, 3H).

Alternate Preparation of Example 10

Alternate Preparation 10A: tert-Butyl ((1R,3S)-3-((R)-6-hexyl-5,6,7,8-tetrahydronaphthalen-2-yl)-1-(hydroxymethyl)cyclopentyl)carbamate

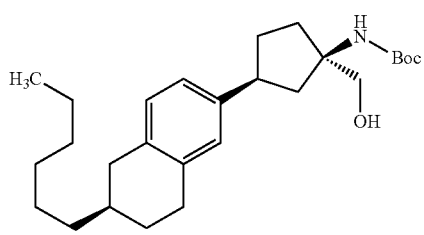

(10A)

To a stirred solution of ((1R,3S)-1-amino-3-((R)-6-hexyl-5,6,7,8-tetrahydronaphthalen-2-yl)cyclopentyl)methanol (Example 2, 270 mg, 0.819 mmol) in anhydrous dichloromethane (6 mL) was added di-tert-butyl dicarbonate (536 mg, 2.458 mmol). The resulting solution was stirred at room temperature for 3 h. The mixture was concentrated. Flash chromatography purification (24 g silica gel column, gradient elution from 10 to 60% of ethyl acetate in hexanes) afforded tert-butyl ((1R,3S)-3-((R)-6-hexyl-5,6,7,8-tetrahydronaphthalen-2-yl)-1-(hydroxymethyl)cyclopentyl)carbamate (337 mg, 0.784 mmol, 96% yield) as a white solid. LC/MS $M^{+1}$=430.

Alternate Preparation 10B: tert-Butyl ((1R,3S)-1-(((bis(2-(trimethylsilyl)ethoxy)phosphoryl)oxy)methyl)-3-((R)-6-hexyl-5,6,7,8-tetrahydronaphthalen-2-yl)cyclopentyl)carbamate

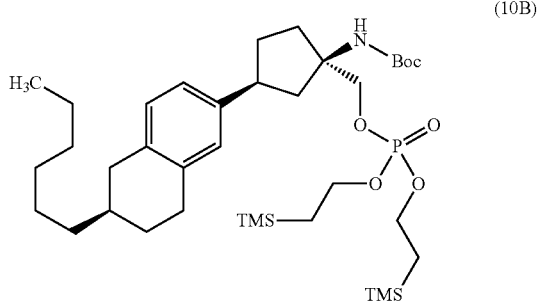 [SMILES: CCCCCC[C@@H]1CCc2cc([C@H]3CC[C@@](COP(=O)(OCC[Si](C)(C)C)OCC[Si](C)(C)C)(NC(=O)OC(C)(C)C)C3)ccc2C1]

(10B)

To a stirred solution of tert-butyl ((1R,3S)-3-((R)-6-hexyl-5,6,7,8-tetrahydronaphthalen-2-yl)-1-(hydroxymethyl)cyclopentyl)carbamate (Preparation 10A, 336 mg, 0.782 mmol)

in anhydrous methylene chloride (7 mL) was added bis(2-(trimethylsilyl)ethyl)diisopropylphosphoramidite (858 mg, 2.346 mmol) in one portion at 0° C. under nitrogen. Next, 1, 2, 4-1H-triazole (162 mg, 2.346 mmol) was then added. The reaction mixture was stirred at 40° C. for 18 h. The solution was cooled to 0° C. before hydrogen peroxide (0.781 mL, 7.82 mmol) was added. The mixture was stirred at 0° C. for 30 minutes at room temperature for 1 h before methanol (3 mL) was added to make the mixture a homogeneous solution. The solution was stirred at room temperature for 1 h. A saturated aqueous sodium thiosulfate solution (5 mL) was added to quench the reaction. The mixture was concentrated under reduced pressure and extracted with ethyl acetate (3×4 mL). The combined organic solutions were dried (Na$_2$SO$_4$) and concentrated under reduced pressure. Flash chromatography purification (24 g silica gel column, gradient elution from 5 to 25% of ethyl acetate in hexanes) afforded tert-butyl ((1R,3S)-1-(((bis(2-(trimethylsilyl)ethoxy)phosphoryl)oxy)methyl)-3-((R)-6-hexyl-5,6,7,8-tetrahydronaphthalen-2-yl)cyclopentyl)carbamate (514 mg, 0.724 mmol) as a liquid.

Example 10

To a stirred solution of tert-butyl ((1R,3S)-1-(((bis(2-(trimethylsilyl)ethoxy)phosphoryl)oxy)methyl)-3-((R)-6-hexyl-5,6,7,8-tetrahydronaphthalen-2-yl)cyclopentyl) carbamate (Preparation 10B, 500 mg, 0.704 mmol) in dichloromethane (6 mL) was added TFA (6 mL) slowly at 0° C. The mixture was stirred at room temperature for 3 h before 90 mL of heptanes was added. The solution was concentrated under reduced pressure. Next, 70 mL of methanol was added to the solid residue, followed by 1N aq NaOH (4 mL). HOAc (0.4 mL) was then added at 60° C. to acidify the solution to pH=4. The solid-liquid mixture was stirred at 60° C. for 1 h. The solid was separated, washed with methanol, water, methanol, ethyl acetate, and methanol. Lyophilization gave ((1R,3S)-1-amino-3-((R)-6-hexyl-5,6,7,8-tetrahydronaphthalen-2-yl)cyclopentyl)methyl dihydrogen phosphate (257 mg, 0.619 mmol, 88% yield) as a white solid. LC/MS M$^{+1}$=410; $^1$H NMR (400 MHz, methanol-d$_4$)(+KOH) δ 7.00-6.86 (m, 3H), 3.78-3.62 (m, 2H), 3.09-2.97 (m, 1H), 2.84-2.67 (m, 3H), 2.38-2.22 (m, 2H), 2.03-1.74 (m, 4H), 1.73-1.60 (m, 2H), 1.50 (t, J=12.3 Hz, 1H), 1.44-1.27 (m, 11H), 0.95-0.86 (m, 3H).

Comparative Compound 11

(1R,3R)-1-Amino-3-(6-(pentyloxy)naphthalen-2-yl) cyclopentyl)methanol (11)

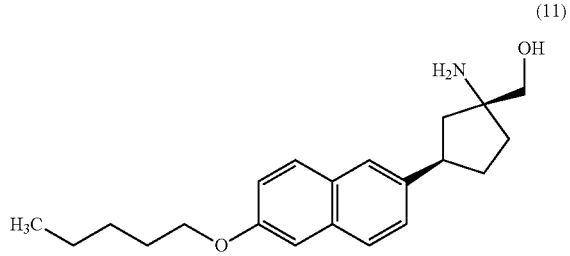 [SMILES: CCCCCOc1ccc2cc([C@@H]3CC[C@](N)(CO)C3)ccc2c1]

Comparative Compound 11 was disclosed in WO 2008/079382, Example Q.1.

Intermediate 11A: (5R,7R)-7-(6-(Pentyloxy)naphthalen-2-yl)-3-oxa-1-azaspiro[4.4]nonan-2-one (I-11A)

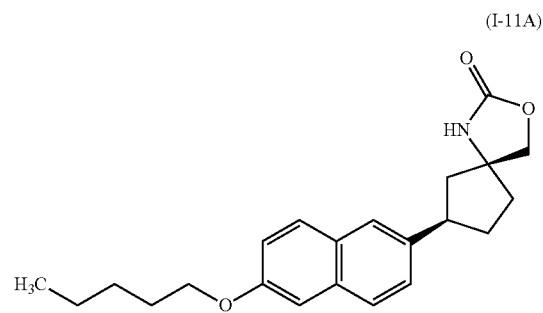 [SMILES: CCCCCOc1ccc2cc([C@@H]3CC[C@]4(COC(=O)N4)C3)ccc2c1]

A mixture of 1-pentanol (6.13 mL, 56.4 mmol), p-toluenesulfonic acid monohydrate (4.60 mg, 0.024 mmol), and trimethoxymethane (0.353 mL, 3.22 mmol) was stirred at 100° C. for 3 hr with a slow air stream flowing over the mixture to remove methanol and some pentanol. The obtained residual liquid was mixed with (5R,7R)-7-(6-oxo-5,6,7,8-tetrahydronaphthalen-2-yl)-3-oxa-1-azaspiro[4.4]nonan-2-one (Int. 7, 230 mg, 0.806 mmol) and stirred at 100° C. under nitrogen for 2.5 hr. The solution was allowed to cool down to room temperature before palladium on carbon (172 mg, 0.081 mmol) was added, followed by ethyl acetate (4 mL). The mixture was left to stir under a balloon-pressure of hydrogen at room temperature overnight. The resulting mixtures were filtered through a membrane filter and the filtrate was concentrated. Flash chromatography purification (24 g silica gel column, 0% to 70% ethyl acetate in hexanes) afforded 180 mg of material that required additional purification. Supercritical Fluid Chromatographic separation afforded a major fraction by UV analysis identified as (5R,7R)-7-(6-(pentyloxy)naphthalen-2-yl)-3-oxa-1-azaspiro[4.4]nonan-2-one (36 mg) as a solid. Instrument: Thar 350 Thar Analytical SFC-MS; Conditions: Analytical Conditions: Analytical Column: AD-H (0.46×25 cm, 5 μm); BPR pressure: 100 bars; Temperature: 45° C.; Flow rate: 3.0 mL/min; Mobile Phase: CO$_2$/MeOH (70/30); Detector Wavelength: UV 200-400 nm. Preparative Conditions: Preparative Column: AD-H (3×25 cm, 5 μm); BPR pressure: 100 bars; Temperature: 35° C.; Flow rate: 120 mL/min; Mobile Phase: CO$_2$/MeOH (70/30); Detector Wavelength: 220 nm; Separation program: Stack injection; Injection: 2.5 mL with cycle time 480 sec. (Analytical SFC ret. time=11.68 min, purity >99.5%) HPLC retention time=1.11 min (Condition G); LC/MS M$^{+1}$=354. $^1$H NMR (400 MHz, chloroform-d) δ 7.68 (d, J=8.4 Hz, 2H), 7.55 (s, 1H), 7.30 (s, 1H), 7.21-7.04 (m, 2H), 6.48 (br. s., 1H), 4.50-4.28 (m, 2H), 4.07 (t, J=6.6 Hz, 2H), 3.49-3.31 (m, 1H), 2.46 (dd, J=13.3, 7.6 Hz, 1H), 2.39-2.24 (m, 1H), 2.24-2.12 (m, 1H), 2.12-2.00 (m, 1H), 2.00-1.90 (m, 1H), 1.90-1.76 (m, 3H), 1.58-1.30 (m, 4H), 0.96 (t, J=7.0 Hz, 3H).

Comparative Compound 11

To a solution of (5R,7R)-7-(6-(pentyloxy)naphthalen-2-yl)-3-oxa-1-azaspiro[4.4]nonan-2-one (36 mg, 0.102 mmol) in dioxane (2 mL) and water (0.8 mL) was added LiOH (36.6 mg, 1.528 mmol). The solution was heated to 90° C. and allowed to stir for 15 hours. The reaction mixture was cooled to room temperature and was poured into ethyl acetate and washed with water. The crude material was then purified on reverse phase HPLC [Column: Luna Axia 30*100 mm; Gradient time: 10 min; Flow rate=40 ml/min; Solvent A=10% MeOH-90% Water-0.1% TFA; Solvent B=90% MeOH-10% water-0.1% TFA; Start % B=20; Final % B=100]. The product containing fractions were collected and dried under high vacuum to provide ((1R,3R)-1-amino-3-(6-(pentyloxy)naphthalen-2-yl)cyclopentyl)methanol, TFA (31 mg) as a solid. HPLC retention time=0.90 min (Condition G); LC/MS $M^{+1}$=328. $^1$H NMR (400 MHz, methanol-$d_4$) δ 7.75-7.66 (m, 2H), 7.66-7.59 (m, 1H), 7.40-7.33 (m, 1H), 7.17 (d, J=2.6 Hz, 1H), 7.14-7.08 (m, 1H), 4.07 (t, J=6.5 Hz, 2H), 3.74-3.60 (m, 2H), 3.59-3.41 (m, 1H), 2.39-2.22 (m, 3H), 2.04-1.80 (m, 5H), 1.55-1.34 (m, 4H), 1.01-0.89 (m, 3H).

BIOLOGICAL ASSAYS

Mouse Whole Blood Phosphorylation (WBP) Assay

The compounds of Formula (III) require bioactivation through phosphorylation of the alcohol to provide an active phosphate ester compound of Formula (II). According to Brinkmann, V. et al., (*J. Biol. Chem.* 277:21453-21457 (2002)), the stereoisomeric configuration of the amine bearing carbon center can influence the relative extent to which this phosphorylation takes place.

The relative extent of phospholylation of Examples 1-2 and Compounds 3-8 were evaluated by incubation of the alcohol compounds in whole blood from a mouse. The appearance of the phosphorylated compound was measured after 4 hours to determine the relative extent of phosphate ester formation. Whole blood was freshly obtained from BALB/C mice by retro-orbital bleeding and collected into EDTA containing tubes. The EDTA treated whole blood was aliquoted into 1.4 mL polypropylene tubes in 96 well format (100 μL per sample) and spiked with test compound (1 mM in DMSO) for a final concentration of 10 μM (n=2 per compound). Tubes were sealed and vortexed then transferred to orbital shaker for incubation at 37° C., 225 RPM for 4 hours. At the end of the incubation, samples were spotted onto Ahlstrom 226 untreated Specimen Collection Paper (25 μL per spot n=2) and allowed to air dry overnight. Dried Blood Spot (DBS) Cards were stored at ambient temperature in sealed plastic bags with desiccant added. When ready for analysis, a 6 mm punch (equivalent to 12.5 μl of wet blood) was taken at n=1 and placed in a shallow 96-well filter plate. Next, 105 μL of a mixture of 75% acetonitrile and 25% water containing Internal Standard was added and gently vortexed for 30 min then centrifuged. Supernatant was separated from the protein pellet and 5 μl was injected. The parent (alcohol) and active phosphate ester compounds were quantitatively analyzed, using a DBS calibration curve, by LC/MS/MS on a Triple Quadrapole Instrument. The area ratios of the phosphorylated compound to the parent (alcohol) compound were determined. A larger value for the ratio of the phosphorylated compound to the parent (alcohol) compound indicated greater phosphate ester compound formation from the parent (alcohol) compound. Table 2 shows the results (average of two experiments) for Examples 1-2 and Compounds 3-8 at 4 hours. For Examples 1-2 and Compound 6, the area ratios of the phosphate ester compound formation from the parent (alcohol) compounds at 4 hour were at least 0.59. In contrast, the area ratios of the phosphate ester compound formation from parent (alcohol) compounds for Compounds 3-5 and 7-8 were 0.17 or less. In this study, Examples 1-2 and Compound 6 were found to undergo phosphorylation to a greater extent than Compounds 3-5 and 7-8.

TABLE 2

Mouse Whole Blood Phosphorylation - Extent of Phosphorylation

| Example or Compound No. | Mouse Whole Blood Phosphate Area Ratio at 4 hr |
|---|---|
| 1 | 1.60 |
| 2 | 0.59 |
| 3 | 0.07 |
| 4 | 0.14 |
| 5 | 0.03 |
| 6 | 0.60 |
| 7 | 0.02 |
| 8 | 0.17 |

In Vivo Phosphate Ester Formation in Mice

BALB/c mice were dosed orally with Example 1, Example 2, Compound 3, and Compound 4 (10 mg/kg as a solution or suspension in the vehicle, polyethylene glycol 300, "PEG300"). Blood was drawn at 24 hr, spotted onto Dried Blood Spot (DBS) Cards, and analyzed as described for the WBP assay. Reference material (parent alcohol and phosphate ester) was analyzed to optimize the LC-MS/MS assay and enable data reporting in concentrations. DBS standard curves containing both parent alcohol and phosphate ester compounds were prepared and analyzed in the same manner as the study samples and analyzed by the optimized LC-MS/MS to quantify the amount of phosphate ester compound formed. The results in Table 3 represent the average results of all animals within each treatment group (n=3). A larger value for the phosphate ester compound concentration indicated greater phosphate ester compound formation from parent (alcohol) compound. In this study, Examples 1-2 were found to undergo phosphate ester formation to a greater extent than Compounds 3-4. The results of this in vivo study are consistent with the results obtained in the above Mouse Whole Blood Phosphorylation study.

TABLE 3

In Vivo Phosphate Formation in Mice

| Example or Compound No. | Dosage (mg/kg) | Phosphate at 24 hr (nM) |
|---|---|---|
| 1 | 10 | 475 |
| 2 | 10 | 202 |
| 3 | 10 | 14 |
| 4 | 10 | 46 |

$S1P_1$ Binding Assay

Membranes were prepared from CHO cells expressing human $S1P_1$. Cells pellets ($1\times10^9$ cells/pellet) were suspended in buffer containing 20 mM HEPES (4-(2-hydroxyethyl)-1-piperazineethanesulfonic acid), pH 7.5, 50 mM NaCl, 2 mM EDTA (Ethylenediaminetetraacetic acid) and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM $MgCl_2$, 2 mM EDTA and stored in aliquots at −80° C. after protein concentration determination.

Membranes (2 μg/well) and 0.03 nM final concentration of $^{33}$P-S1P ligand (1 mCi/ml, Perkin Elmer or American Radiolabeled Chemicals) diluted in assay buffer (50 mM HEPES, pH7.4, 5 mM $MgCl_2$, 1 mM $CaCl_2$, 0.5% fatty acid free BSA (bovine serum albumin), 1 mM NaF) were added to the compound plates (384 FALCON® v-bottom plate (0.5 μl/well in a 11 point, 3-fold dilution). Binding was performed for 45 minutes at room temperature, terminated by collecting the membranes onto 384-well Millipore FB filter plates, and radioactivity was measured by TOPCOUNT®. The competition data of the test compounds over a range of concentrations was plotted as percentage inhibition of radioligand specific binding. The $IC_{50}$ is defined as the concentration of competing ligand needed to reduce specific binding by 50%. The $IC_{50}$ for Example 10 was determined to be 0.01 nM.

Receptor [$^{35}$S] GTPγS Binding Assays

Compounds were loaded in a 384 FALCON® v-bottom plate (0.5 µl/well in a 11 point, 3-fold dilution). Membranes prepared from $S1P_1$/CHO cells or EDG3-Ga15-bla HEK293T cells (EDG3 equivalent $S1P_3$) were added to the compound plate (40 µl/well, final protein 3 µg/well) with MULTIDROP®. [$^{35}$S]GTP (1250 Ci/mmol, Perkin Elmer) was diluted in assay buffer: 20 mM HEPES, pH7.5, 10 mM $MgCl_2$, 150 mM NaCl, 1 mM EGTA (ethylene glycol tetraacetic acid), 1 mM DTT (Dithiothreitol), 10 µM GDP, 0.1% fatty acid free BSA, and 10 µg/ml Saponin to 0.4 nM. 40 µl of the [$^{35}$S] GTP solution was added to the compound plate with a final concentration of 0.2 nM. The reaction was kept at room temperature for 45 min. At the end of incubation, all the mixtures in the compound plate were transferred to Millipore 384-well FB filter plates via the VELOCITY11® Vprep liquid handler. The filter plate was washed with water 4 times by using the manifold Embla plate washer and dried at 60° C. for 45 min. MicroScint 20 scintillation fluid (30 µl) was added to each well for counting on the Packard TOPCOUNT®. $EC_{50}$ is defined as the agonist concentration that corresponds to 50% of the Ymax (maximal response) obtained for each individual compound tested. The $EC_{50}$ for Example 10 was determined to be 0.9 nM in the assay utilizing membranes prepared from $S1P_1$/CHO cells. The $EC_{50}$ for Example 10 was determined to be >62,500 nM in the assay utilizing membranes prepared from EDG3-Ga15-bla HEK293T cells.

A smaller value for GTPγS $S1P_1$ $EC_{50}$ value indicated greater activity for the compound in the GTPγS $S1P_1$ binding assay. A larger value for the GTPγS $S1P_3$ $EC_{50}$ value indicated less activity in the GTPγS $S1P_3$ binding assay. Example 10, which is the active phosphate ester of Example 2, possessed activity as an agonist of $S1P_1$ and is selective over $S1P_3$. Thus the compounds of the present invention, which include Examples 1-2 and 9-10 may be used in treating, preventing, or curing various $S1P_1$ receptor-related conditions while reducing or minimizing the side effects due to $S1P_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, lupus, or psoriasis, while reducing or minimizing possible side effects due to $S1P_3$ activity. Other potential uses of the compounds of the present invention include minimizing or reducing rejection of transplanted organs, while reducing or minimizing side effects due to $S1P_3$ activity.

S1P1 Receptor Internalization Assay

CHO-K1 cells expressing a GFP-tagged S1P1 receptor were plated in 384-well poly-D-lysine coated tissue culture plates at $4\times10^3$ cells/well in 50 µl assay media (F12 with L-glutamine, 10% charcoal/dextran-treated FBS, 1× penicillin-streptomycin, 1M HEPES). Cell plates were incubated overnight at 37° C./5% $CO_2$. Test compound were introduced to the cell plate from a compound source plate at 11 point, 3 fold serial dilutions and then the assay plates were incubated at 37° C./5% $CO_2$ for 45 min. Cells were fixed and stained with 6% formaldehyde and 15 µg/ml Hoechst dye in PBS ($Ca^{2+}/Mg^{2+}$ free) at room temperature for 15 minutes. Cell plates were washed 4 times with PBS ($Ca^{2+}/Mg^{2+}$ free) with addition of 50 µl/PBS prior to plate sealing. Images were acquired by the Cellomics ARRAYSCAN® VTI high content imager. Data analysis for $EC_{50}$ determination relative to internal control compound was accomplished using the Compartmental Analysis BioApplication on the Array Scan. The $EC_{50}$ is defined as the agonist concentration that corresponds to 50% of the Ymax (maximal response) obtained for each individual compound tested and was quantified using the 4 parameter logistic equation to fit the data. The $EC_{50}$ for Example 9 was determined to be 361 nM in the assay Blood Lymphocyte Reduction (BLR) Assay in Rodent Lewis rats were dosed orally with vehicle alone (polyethylene glycol 300, "PEG300") or with 2-amino-2-[2-(4-octylphenyl)ethyl]-1,3-propanediol, hydrochloride (CAS: 162359-56-0) as a solution in the vehicle at doses of 0.1 mg/kg, 0.5 mg/kg and 3.0 mg/kg adjusted to reflect the free amount of test article. The results are provided in Table 4a and the level of lymphocyte reduction at 24 hours post-dose was maximal at 3.0 mg/kg. The percent reduction in lymphocytes is dose-related but the relationship is not linear, with non-proportional increases in dose being required to elicit sequentially greater reductions in lymphocyte counts. For example, in this study to demonstrate a change of 13% (from 69% reduction to 82% reduction) required escalation of five-fold in dose (from 0.1 mg/kg to 0.5 mg/kg). Furthermore, to demonstrate an additional change of 7% in this study (from 82% reduction to 89% reduction) required escalation of six-fold in dose (from 0.5 mg/kg to 3.0 mg/kg). BALB/c mice were dosed orally with vehicle alone (polyethylene glycol 300, "PEG300") or with Example 1, Example 2, Compound 6, Compound 8, or Comparative Compound 11. Compounds were dosed as a solution or suspension in the vehicle, adjusted to reflect the free amount of test article in the event that salt forms are utilized. Blood was drawn at 24 hr and blood lymphocyte counts were determined on an ADVIA® 120 Hematology Analyzer (Siemens Healthcare Diagnostics). The results were measured as a reduction in the percentage of circulating lymphocytes as compared to the vehicle treated group at the time of measurement. The results represent the average results of all animals within each treatment group (n=2-4). The results of the Blood Lymphocyte Reduction assay (BLR) in mouse described hereinabove are shown in Table 4b.

TABLE 4a

2-Amino-2-[2-(4-octylphenyl)ethyl]-1,3-propanediol, hydrochloride

| Dosage | Rat Blood Lymphocyte Reduction Assay at 24 hr post-dose | | | | Percent reduction |
|---|---|---|---|---|---|
| | Compound | | Vehicle Control | | |
| (mg/kg) | Mean | SEM | Mean | SEM | vs. control |
| 0.1 | 2.78 | 0.17 | 9.01 | 0.19 | 69% |
| 0.5 | 1.64 | 0.25 | 9.01 | 0.19 | 82% |
| 3.0 | 1.02 | 0.06 | 9.01 | 0.19 | 89% |

TABLE 4b

Mouse Blood Lymphocyte Reduction Assay at 24 hr post-dose

| Example or Compound No | Dosage (mg/kg) | Compound Mean | SEM | Vehicle Control Mean | SEM | Percent reduction vs. control |
|---|---|---|---|---|---|---|
| 1 | 1 | 0.7 | 0.11 | 5.39 | 0.67 | 88% |
| 2 | 1 | 0.54 | 0.20 | 5.39 | 0.67 | 90% |
| 6 | 1 | 1.2 | 0.21 | 5.9 | 1.75 | 78% |
| 8 | 1 | 2.4 | 0.35 | 5.9 | 1.75 | 59% |
| 11 | 1 | 2.18 | 0.63 | 4.58 | 0.14 | 52% |

Pulmonary Toxicity Assay

The analysis of protein levels in bronchoalveolar lavage (BAL) fluid obtained from an animal were used to gauge pulmonary side effects. Increased levels of protein in BAL fluid were indicative of undesired pulmonary effects, such as pulmonary edema. Example 1, Example 2, Compound 6, Compound 8, and Compound 11 were administered orally to mice at a dose of 30 mg/kg. At 24 hours post dose, the mice were euthanized with intraperitoneal barbiturate overdose. The animals were placed in a supine position, a skin incision was made and blunt dissection followed to expose the trachea. The trachea was incised and a catheter was inserted 4-6 mm into the trachea. Phosphate-buffered saline (PBS; 1 mL/mouse) was infused into the lungs and then aspirated. The concentration of the BAL protein in the recovered BAL fluid was determined on an ADVIA® 1800 Chemistry Analyzer (Siemens Healthcare Diagnostics). The results of the bronchoalveolar lavage (BAL) assay are shown in Table 5. The results represent the average results of all animals within each treatment group (n=2-4).

TABLE 5

| Example or Compound No | Dosage (mg/kg) | Compound Mean | SEM | Vehicle Control Mean | SEM | Relative BAL protein vs. control |
|---|---|---|---|---|---|---|
| 1 | 30 | 8.25 | 1.0 | 8.3 | 0.33 | 0.99 |
| 2 | 30 | 8.0 | 0.0 | 8.3 | 0.33 | 0.96 |
| 6 | 30 | 14.3 | 2.0 | 7.3 | 1.3 | 1.96 |
| 8 | 30 | 7.5 | 1.0 | 7.3 | 1.0 | 1.03 |
| 11 | 30 | 13.3 | 0.5 | 10.0 | 1.0 | 1.33 |

Table 5 shows the relative BAL protein levels at 24 hours for the tested compounds compared to the administration of vehicle only. A value for the relative BAL protein versus control of greater than 1 indicated an increase in pulmonary toxicity compared to the administration of vehicle only. In this study, as reported in Table 5, the administration of Examples 1 and 2 gave relative BAL protein levels of 0.99 and 0.96, indicating no increase in the pulmonary toxicity. The administration of Compound 8 gave a relative BAL protein level of 1.03, which indicated slight or no increase in pulmonary toxicity. In contrast, administration of Compound 6 and Compound 11 gave relative BAL protein levels of 1.94 and 1.33, indicating increased pulmonary toxicity.

The compounds of the present invention, as exemplified by Examples 1 and 2, have been compared to a) Compounds 6 and 8, and b) Comparative Compound 11, disclosed in WO 2008/079382, and have been found to be especially advantageous. The compounds of the present invention had the surprising advantage of the combination of activity in reducing blood lymphocytes and minimizing pulmonary side effects, such as pulmonary edema. As shown in Tables 4b and 5, in the reported tests, Examples 1 and 2 of this invention show the surprising advantage in efficacy of reducing blood lymphocytes without increasing in the BAL protein, a measure of pulmonary side effects. For example, as compared to Compounds 6, 8, and 11, the exemplified compounds of the invention reported in Table 4b and 5 reduced the blood lymphocytes by 88% and 90%, and gave relative BAL protein levels of 0.99 and 0.96, respectively, which indicated no increase in pulmonary side effects. In contrast, in similar tests, Compound 6 and Comparative Compound 11 reduced blood lymphocytes by 78% and 52%, and gave relative BAL protein levels of 1.96 and 1.33, respectively, indicating increased risk of pulmonary side effects. Compound 8 reduced blood lymphocytes by 59% and gave relative BAL protein levels of 1.03, which indicated no or slight increase in pulmonary side effects.

TABLE 6

Mouse Blood Lymphocyte Reduction and Mouse BAL Protein Levels from Tables 4b and 5

| Example or Compound No | Mouse Blood Lymphocyte Reduction Assay at 24 hr post-dose (Percent reduction vs. control) at 1 mg/kg | Mouse BAL protein level (24 hr post-dose) Relative BAL protein vs. control at 30 mg/kg |
|---|---|---|
| 1 | 88% | 0.99 |
| 2 | 90% | 0.96 |
| 6 | 78% | 1.96 |
| 8 | 59% | 1.03 |
| 11 | 52% | 1.33 |

The compounds of the present invention possess activity as agonists of the $S1P_1$ receptor, leading to the reduction of circulating blood lymphocytes, and thus may be used in treating, preventing, or curing various $S1P_1$ receptor-related conditions while reducing or minimizing pulmonary side effects, such as pulmonary edema. The surprising selectivity of the compounds of the present invention indicate their potential use in treating, preventing, or curing autoimmune and inflammatory diseases such as multiple sclerosis, rheumatoid arthritis, inflammatory bowel diseases, lupus, or psoriasis, while reducing or minimizing possible pulmonary side effects. Other potential uses of the compounds of the present invention include minimizing or reducing rejection of transplanted organs, while reducing or minimizing possible pulmonary side effects.

Rat Adjuvant Induced Arthritis Assay (AA)

The rat adjuvant-induced arthritis model is an animal model for human rheumatoid arthritis.

Male Lewis rats (150-175 g; Harlan, n=8 treatment group) were immunized at the base of the tail with 100 µl of 10 mg/ml freshly ground *Mycobacterium butyricum* (Difco Laboratories) in incomplete Freund's adjuvant (sigma). Animals were dosed once daily with the test article (as a solution or suspension in the vehicle) or vehicle alone (polyethylene glycol 300, "PEG300") starting from the day of immunization. The volumes of their hind paws were measured in a water displacement plethysmometer (Ugo Basile, Italy). The baseline paw measurements were taken before onset of the disease (between day 7 to day 10). The paw measurements were then taken three times a week until the end of the study on day 20 to 21. All procedures involving animals were reviewed and approved by the Institutional Animal Care Use Committee.

Example 2 of the present invention was tested in the Rat Adjuvant Induced Arthritis assay described hereinabove and the results are shown in Table 7. The compound of this invention, as exemplified by Example 2, in the reported test, showed inhibition of disease progression as measured by reduced paw swelling in the Lewis rat using a prophylactic oral dosing regimen.

TABLE 7

| Group | | Paw Swelling (mL) on Day 20 |
|---|---|---|
| Vehicle | Mean | 1.78 |
| | SEM | 0.14 |
| Example 2 | Mean | 1.64 |
| (0.15 mg/kg) | SEM | 0.10 |
| Example 2 | Mean | 0.70 |
| (0.5 mg/kg) | SEM | 0.13 |
| Example 2 | Mean | 0.16 |
| (1.5 mg/kg) | SEM | 0.04 |

Mouse T Cell Transfer Induced Colitis Assay

The mouse T Cell transfer induced colitis assay is an animal model for human colitis.

Colitis was induced in CB-17 SCID mice by the adoptive transfer of FACS sorted $CD4^+CD45RB^{high}$ T cells from BALB/c mice ($3 \times 10^5$/mouse, i.p.). Disease activities were monitored once a week for the initial 3 weeks and 3×/week for the subsequent weeks on the basis of body weight, soft stool or diarrhea, and anorectal prolapse. Animals were dosed orally every other day (q.o.d.) with the test article or vehicle starting from the day of T cell transfer. Mice were sacrificed 6 wk after T cell reconstitution and analyzed for bowel inflammation based on histological examination of H&E stained colon tissues. All procedures involving animals were reviewed and approved by the Institutional Animal Care Use Committee.

Example 2 was tested in the mouse T cell transfer induced colitis model described hereinabove and the results are shown in Table 8. The compound of this invention, as exemplified by Example 2, in the reported test, showed inhibition of disease progression as measured by reduced body weight loss or increase body weight, and a reduction in inflammation and damage in the mouse T Cell transfer induced colitis assay.

TABLE 8

| Group | | Week 6 Percent Body Weight Changes | | Inflammation/ Damage (Histology) | |
|---|---|---|---|---|---|
| Vehicle | Mean | 100% → | 96.8% | Mean | 6.79 |
| | SD | | 2.4% | SEM | 0.36 |
| Example 2 | Mean | 100% → | 98.7% | Mean | 5.46 |
| (1 mg/kg; q.o.d.) | SD | | 1.5% | SEM | 0.32 |
| Example 2 | Mean | 100% → | 103.7% | Mean | 3.71 |
| (5 mg/kg; q.o.d.) | SD | | 1.3% | SEM | 0.50 |

MRL/lpr Mouse Model of Spontaneous Lupus Erythematosus Assay

MRL/lpr mouse model of spontaneous lupus erythematosus assay is an animal model for spontaneous lupus erythematosus.

Male MRL/lpr mice (14 weeks old; Jackson Laboratories; n=12-13) were orally dosed with Example 2 (as a solution in vehicle) or vehicle alone (polyethylene glycol 300) twice a week for 11 weeks starting on day 0. Urine protein levels (by Albustix) were measured on day 0 and throughout the study. Table 9 indicates the percentage of mice in each treatment groups that demonstrated high levels of proteinurea (greater than 100 mg/dL) at 25 weeks of age. Additional groups of mice received a daily oral dose of dexamethasone (Dex) either independently or in combination with twice weekly dosing with Example 2. Urine protein levels (by Albustix) were measured on day 0 and throughout the study. Table 9 indicates the percentage of mice in each treatment groups that demonstrated high levels of proteinurea (greater than 100 mg/dL) at 24 weeks of age. All procedures involving animals were reviewed and approved by the Institutional Animal Care Use Committee.

Example 2 was tested in the MRL/lpr mouse model of spontaneous lupus erythematosus assay described hereinabove and the results are shown in Table 9. The compound of this invention, as exemplified by Example 2, in the reported test, showed inhibition of disease progression as measured by a lower percentage of mice with a proteinurea level of greater than 100 mg/dL.

TABLE 9

Proteinurea at 25 Weeks of Age

| Group | % Mice with Proteinurea >100 mg/dL |
|---|---|
| Vehicle | 54 |
| Example 2 | 25 |
| (0.05 mg/kg; 2x week) | |
| Example 2 | 17 |
| (0.4 mg/kg; 2x week) | |
| Example 2 | 10 |
| (2 mg/kg; 2x week) | |

Example 2 and dexamethasone (Dex) either independently or in combination, were tested in the MRL/lpr mouse model of spontaneous lupus erythematosus assay described hereinabove and the results are shown in Table 10. Both the compound of this invention, as exemplified by Example 2, and dexamethasone in the reported test, showed inhibition of disease progression as measured by a lower percentage of mice with a proteinurea level of greater than 100 mg/mL. In this test, no mice administered the combination of Example 2 and dexamethasone had a proteinurea level of greater than 100 mg/mL.

TABLE 10

Proteinurea at 24 Weeks of Age

| Group | % Mice with Proteinurea >100 mg/dL |
|---|---|
| Vehicle | 64 |
| Dex (0.1 mg/kg q.d.) | 50 |
| Dex (0.5 mg/kg q.d.) | 10 |
| Example 2 (2 mg/kg; 2x week) | 20 |
| Example 2 (2 mg/kg; 2x week) + Dex (0.1 mg/kg q.d.) | 0 |

Single Crystal X-Ray Diffractometry

The single crystal data were collected on a Bruker-AXS APEX2 CCD system using Cu Kα radiation ($\lambda=1.5418$ Å). Indexing and processing of the measured intensity data were carried out with the APEX2 software program suite. When indicated, crystals were cooled in the cold stream of an Oxford cryo system during data collection. The structures were solved by the direct methods and refined on the basis of observed reflections using the SHELXTL program. The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Typically, all the non-H atoms were refined anisotropically and all H-atoms other than those attached to N and O atoms were calculated by geometrical methods and refined using a riding model.

X-Ray Powder Diffractometry

X-ray powder diffraction (PXRD) data were obtained using a Bruker GADDS (General Area Detector Diffraction System) manual chi platform goniometer. Powder samples were placed in thin walled glass capillaries of 0.7 mm in diameter; the capillaries were rotated during data collection. The sample-to-detector distance was kept at 17 cm. Data were collected with Cu Kα radiation ($\lambda$=1.5418 Å) in the range 2.5<2θ<35° with a sample exposure time of 600 seconds.

What is claimed is:
1. A compound of Formula (I):

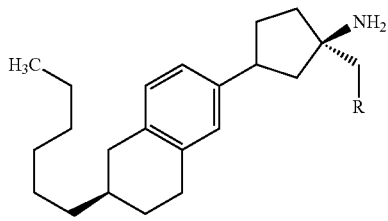

(I)

and/or a salt thereof; wherein R is —OH or —OP(O)(OH)$_2$.

2. The compound according to claim 1 or a salt thereof, wherein R is —OH.

3. The compound according to claim 1 or a salt thereof, wherein R is —OP(O)(OH)$_2$.

4. The compound according to claim 1 or a salt thereof, having the structure:

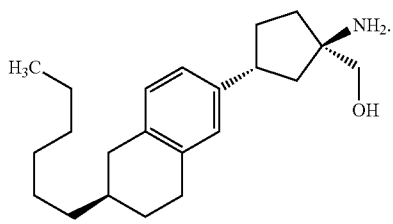 [SMILES: CCCCCC[C@@H]1CCc2cc([C@@H]3CC[C@](N)(CO)C3)ccc2C1]

5. A compound or a salt thereof, having the structure:

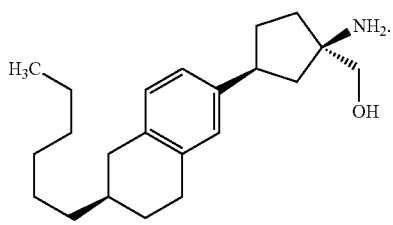 [SMILES: CCCCCC[C@@H]1CCc2cc([C@H]3CC[C@](N)(CO)C3)ccc2C1]

6. The compound according to claim 5 or a salt thereof, wherein said compound or said salt is a crystalline solid.

7. The compound according to claim 1 or a salt thereof, having the structure:

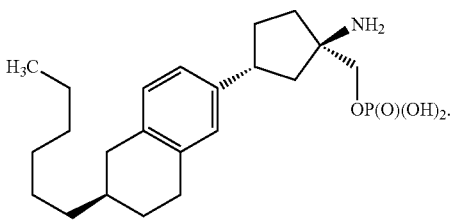

8. The compound according to claim 1 or a salt thereof, having the structure:

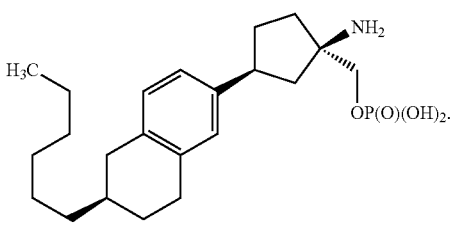

9. A pharmaceutical composition comprising a compound according to claim 2 or a pharmaceutically acceptable salt thereof; and a pharmaceutically acceptable carrier.

10. A method of inhibiting and/or relieving a disease or disorder associated with the activity of G protein-coupled receptor S1P$_1$, the method comprising administering to a mammalian patient in need of inhibiting and/or relieving of said disease or disorder associated with the activity of G protein-coupled receptor S1P$_1$ a compound according to claim 1 or a pharmaceutically acceptable salt thereof, wherein said disease or disorder is selected from lupus, multiple sclerosis, and rheumatoid arthritis.

11. The method according to claim 10 wherein said compound is

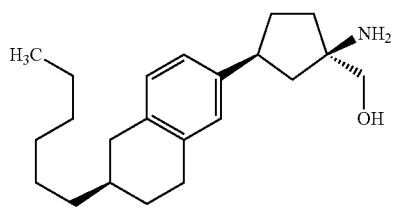 [SMILES: CCCCCC[C@@H]1CCc2cc([C@H]3CC[C@](N)(CO)C3)ccc2C1]

or a pharmaceutically-acceptable salt thereof.

12. A method of inhibiting and/or relieving an autoimmune disease or a chronic inflammatory disease, comprising administering to a mammalian patient in need of inhibiting and/or relieving of said autoimmune disease or chronic inflammatory disease a compound according to claim 1 or a pharmaceutically acceptable salt thereof, wherein said disease or disorder is selected from lupus, multiple sclerosis, inflammatory bowel disease, and rheumatoid arthritis.

13. The method according to claim 12 wherein said mammalian patient is a human.

14. The method according to claim 13 wherein said compound is

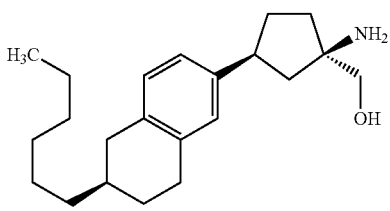 [SMILES: CCCCCC[C@@H]1CCc2cc([C@H]3CC[C@](N)(CO)C3)ccc2C1]

or a pharmaceutically-acceptable salt thereof.

15. The method according to claim 13 wherein said compound is

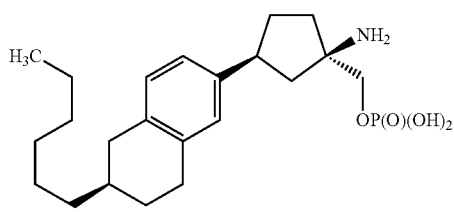

or a pharmaceutically-acceptable salt thereof.

16. The compound according to claim 5 or a salt thereof, wherein said salt is a selected from HCl salt, phosphoric acid salt, L-malic acid salt, malonic acid salt, and R-(+)-mandelic acid salt.

17. The compound according to claim 5 or a salt thereof, wherein said salt is a HCl salt.

18. The compound according to claim 5.

19. The pharmaceutical composition according to claim 9 wherein said compound is

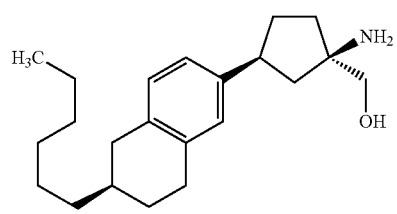 [SMILES: CCCCCC[C@@H]1CCc2cc([C@H]3CC[C@](N)(CO)C3)ccc2C1]

or a pharmaceutically-acceptable salt thereof.

20. The pharmaceutical composition according to claim 9 wherein said compound is

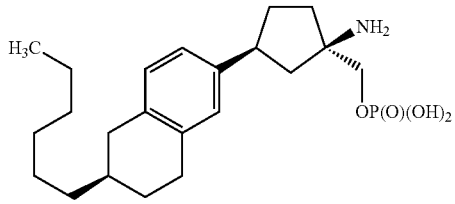

or a pharmaceutically-acceptable salt thereof.

* * * * *